US008981179B2

(12) United States Patent
Dressler et al.

(10) Patent No.: US 8,981,179 B2
(45) Date of Patent: Mar. 17, 2015

(54) TRANSGENIC NON-HUMAN ANIMAL AND USES THEREOF

(75) Inventors: Holly Dressler, Holliston, MA (US); Kyriakos D. Economides, North Grafton, MA (US); Zhen Pang, Stewartsville, NJ (US); Harry Gregory Polites, Ringoes, NJ (US)

(73) Assignee: Sanofi, Bridgewater, NJ (US)

( * ) Notice: Subject to any disclaimer, the term of this patent is extended or adjusted under 35 U.S.C. 154(b) by 0 days.

(21) Appl. No.: 13/516,077

(22) PCT Filed: Dec. 17, 2010

(86) PCT No.: PCT/US2010/060909
§ 371 (c)(1),
(2), (4) Date: Jun. 14, 2012

(87) PCT Pub. No.: WO2011/084659
PCT Pub. Date: Jul. 14, 2011

(65) Prior Publication Data
US 2012/0255041 A1  Oct. 4, 2012

Related U.S. Application Data

(60) Provisional application No. 61/288,480, filed on Dec. 21, 2009, provisional application No. 61/298,973, filed on Jan. 28, 2010, provisional application No. 61/318,919, filed on Mar. 30, 2010.

(30) Foreign Application Priority Data

Sep. 23, 2010 (FR) ...................................... 10 57663

(51) Int. Cl.
*A01K 67/00* (2006.01)
*G01N 33/74* (2006.01)
*A01K 67/027* (2006.01)
*C12N 9/02* (2006.01)
*C12N 15/85* (2006.01)

(52) U.S. Cl.
CPC ............ *G01N 33/74* (2013.01); *A01K 67/0275* (2013.01); *C12N 9/0069* (2013.01); *C12N 15/8509* (2013.01); *A01K 2217/052* (2013.01); *A01K 2217/203* (2013.01); *A01K 2227/105* (2013.01); *A01K 2267/0393* (2013.01); *C12N 2800/107* (2013.01); *C12N 2830/002* (2013.01); *C12N 2830/15* (2013.01); *C12N 2830/40* (2013.01); *C12N 2830/46* (2013.01); *C12N 2830/50* (2013.01); *C12N 2830/60* (2013.01); *C12N 2830/85* (2013.01); *G01N 2333/726* (2013.01)
USPC ............................................... 800/8; 800/18

(58) Field of Classification Search
CPC .................... A01K 2217/072; A01K 2217/05; A01K 2227/105; A01K 2267/0393; A01K 67/0275
See application file for complete search history.

(56) References Cited

U.S. PATENT DOCUMENTS

| 6,020,143 | A  | * | 2/2000  | St. George-Hyslop |
|           |    |   |         | et al. ............................... 435/7.1 |
| 2005/0283854 | A1 | * | 12/2005 | Krumm et al. ................. 800/288 |
| 2006/0206950 | A1 | * | 9/2006  | Kaelin, Jr. ........................ 800/18 |
| 2007/0015149 | A1 | * | 1/2007  | Wang et al. ........................ 435/6 |
| 2010/0261227 | A1 | * | 10/2010 | Cooper et al. ................. 435/69.4 |

OTHER PUBLICATIONS

Palmiter et al. Heterologous Introns Can Enhance Expression of Transgenes in Mice. PNAS, 1991. 88:478-482.*
Böer Ulrike et al: "CRE/CREB-driven up-regulation of gene expression by chronic social stress in CRE-luciferase transgenic mice: reversal by antidepressant treatment." PLOS ONE, vol. 2, No. 5, E431, May 2007, pp. 1-11.
Ciana Paolo et al: "Engineering of a mouse for the in vivo profiling of estrogen receptor activity", Molecular Endocrinology, vol. 15, No. 7, Jul. 2001, pp. 1104-1113.
Hill S J et al: "Reporter-gene systems for the study of G-protein-coupled receptors" Current Opinion in Pharmacology, vol. 1, No. 5, Oct. 1, 2001, pp. 526-532.
Kenakin Terry P: "Cellular assays as portals to seven-transmembrane receptor-based drug discovery." Nature Reuiews Drug Discovery, vol. 8, No. 8, Aug. 2009, pp. 617-626.
McFarland T J et al: "Evaluation of a novel short polyadenylation signal as an alternative to the SU40 polyadenylation signal", PLASMID, vol. 56, No. 1, Jul. 1, 2006, pp. 62-67.
Montoliu Lluis et al: "Analysis of perinatal gene expression: Hormone response elements mediate activation of a lacZ reporter gene in liver of transgenic mice", Proceedings of the National Academy of Sciences of the United States of America, vol. 92, No. 10, 1995, pp. 4244-4248.
Ottobrini L et al: "Molecular imaging: A new way to study molecular processes in vivo", Molecular and Cellular Endocrinology, vol. 246, No. 1-2, Feb. 26, 2006, pp. 69-75.
Thome J et al: "cAMP response element-mediated gene transcription is upregulated by chronic antidepressant treatment" Journal of Neuroscience, New York, NY, US, vol. 20, No. 11, Jun. 1, 2000, pp. 4030-4036.
International Search Report & Written Opinion from PCT/US2010/060909, dated Apr. 6, 2011.

* cited by examiner

*Primary Examiner* — Maria Leavitt
*Assistant Examiner* — Kimberly A Aron
(74) *Attorney, Agent, or Firm* — Lathrop & Gage LLP; James H. Velema, Esq.

(57) ABSTRACT

The present invention relates generally to transgene constructs, transgenic non-human animals comprising transgene constructs, methods of making and methods of using the transgenic non-human animals comprising transgene constructs. An embodiment of the invention relates to methods of assaying the activation of GPCR ligands non-invasively in whole animals, tissue slices, or in native cells using a transgenic model containing a bioluminescent transgene reporter system that is responsive to pathway modulation following ligand binding of GPCR receptors.

17 Claims, 41 Drawing Sheets

|  | Line 11 | | Line 16 | | Line 28 | | Line 91 | | Line 93 | | Line 44 | |
|---|---|---|---|---|---|---|---|---|---|---|---|---|
|  | X | Induced | X | Induced | X | Induced | X | Induced | X | Induced | X | Induced |
| Adipose | 16.8 | 68.5 | 6.1 | 8.5 | 5.9 | 39.2 | 23.3 | 383.3 | 3.3 | 11.6 | 12.9 | 37.5 |
| Intestine | 3.6 | 1.8 | 0.2 | 0.1 | 0.7 | 3.3 | 13.3 | 7.8 | 5.6 | 2.2 | -0.3 | 0.0 |
| Pancreas | 1.8 | 0.3 | 0.9 | 0.2 | 19.7 | 0.1 | 7.5 | 1.5 | 0.3 | 0.1 | 0.3 | 0.1 |
| Spleen | 1.0 | 2.9 | 0.1 | 0.1 | 3.2 | 0.6 | 10.4 | 0.5 | 187.5 | 0.7 | 2.0 | 42.7 |
| Lung | 12.4 | 30.8 | 25.0 | 18.5 | 86.0 | 17.3 | 35.9 | 20.8 | 16.0 | 12.4 | 2.4 | 3.3 |
| Brain | 0.4 | 2.9 | 2.1 | 1.8 | 1.3 | 0.8 | 0.7 | 100.5 | 2.2 | 1.8 | 0.2 | 0.4 |

|  | Line 64 | | Line 90 | | Line 63 | | Line 116 | | Line 175 | | Line 184 | |
|---|---|---|---|---|---|---|---|---|---|---|---|---|
|  | X | Induced | X | Induced | X | Induced | X | Induced | X | Induced | X | Induced |
| Adipose | 19.9 | 24.3 | 12.1 | 21.3 | 51.8 | 121.7 | 19.7 | 333.2 | 20.0 | 10.3 | 0.9 | 28.6 |
| Intestine | 0.3 | 0.7 | 2.3 | 0.3 | 5.3 | 2.0 | 4.7 | 2.0 | 2.7 | 2.3 | 1.5 | 0.9 |
| Pancreas | 0.5 | 0.8 | 1.4 | 0.2 | 1.7 | 0.4 | 1.3 | 0.5 | 0.9 | 0.5 | 0.6 | 0.2 |
| Spleen | 2.5 | 1.7 | -0.3 | 0.1 | 2.4 | 2.0 | 0.8 | 2.6 | 1.6 | 0.8 | 0.9 | 0.8 |
| Lung | 2.6 | 17.1 | 26.1 | 12.3 | 77.7 | 79.1 | 94.4 | 315.6 | 49.5 | 1102.5 | 18.7 | 19.4 |
| Brain | 1.3 | 7.2 | 1.7 | 0.4 | 0.6 | 3.0 | 1.7 | 43.2 | 1.0 | 89.3 | 2.3 | 1.7 |

Figure 26

SEQUENCE LISTING

<160> NUMBER OF SEQ ID NOS: 21

<210> SEQ ID NO 1
<211> LENGTH: 29
<212> TYPE: DNA
<213> ORGANISM: Artificial
<220> FEATURE:
<223> OTHER INFORMATION: IFN forward primer

<400> SEQUENCE: 1
gggggatatc agtcaatatg ttcacccca                                     29

<210> SEQ ID NO 2
<211> LENGTH: 28
<212> TYPE: DNA
<213> ORGANISM: Artificial
<220> FEATURE:
<223> OTHER INFORMATION: IFN reverse primer

<400> SEQUENCE: 2
gggggatatc ctactgtttt aattaagc                                      28

```
<210> SEQ ID NO 3
<211> LENGTH: 31
<212> TYPE: DNA
<213> ORGANISM: Artificial
<220> FEATURE:
<223> OTHER INFORMATION: beta-globin forward primer

<400> SEQUENCE: 3
aaggatcctt aattaaaatt atctctaagg c                                     31

<210> SEQ ID NO 4
<211> LENGTH: 26
<212> TYPE: DNA
<213> ORGANISM: Artificial
<220> FEATURE:
<223> OTHER INFORMATION: beta-globin reverse primer

<400> SEQUENCE: 4
ggatccctgc aggaattcct tttaat                                           26

<210> SEQ ID NO 5
<211> LENGTH: 5689
<212> TYPE: DNA
<213> ORGANISM: Artificial
<220> FEATURE:
<223> OTHER INFORMATION: vector used for transgene

<400> SEQUENCE: 5
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg     120 ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgagctcggt acccggggc     420 gcgccgggat ccttaattaa aattatctct aaggcatgtg aactggctgt cttggttttc     480
atctgtactt catctgctac ctctgtgacc tgaaacatat ttataattcc attaagctgt     540
gcatatgata gatttatcat atgtatttc cttaaaggat ttttgtaaga actaattgaa     600
ttgatacctg taaagtcttt atcacactac ccaataaata ataaatctct tgttcagct     660 ctctgtttct ataaatatgt accagttta ttgtttttag tggtagtgat tttattctct     720
ttctatatat atacacacac atgtgtgcat tcataaaat atacaatttt tatgaataaa     780
aaattattag caatcaatat tgaaaccac tgattttgt ttatgtgagc aaacagcaga     840 ttaaaggaa ttcctgcagg atccttaatt aagttctaga tcacaagttt gtacaaaaaa     900
gctgaacgag aaacgtaaaa tgatataaat atcaatatat taaattagat tttgcataaa     960
aaacagacta cataatactg taaaacacaa catatccagt cactatggcg gccgcattag    1020
gcaccccagg ctttacactt tatgcttccg gctcgtataa tgtgtggatt ttgagttagg    1080
atccgtcgag attttcagga gctaaggaag ctaaaatgga gaaaaaaatc actggatata    1140
ccaccgttga tatatcccaa tggcatcgta agaacatttt tgaggcattt cagtcagttg    1200
ctcaatgtac ctataaccag accgttcagc tggatattac ggcctttta aagaccgtaa    1260 agaaaaataa gcacaagttt tatccggcct tattcacat tcttgcccgc ctgatgaatg    1320
ctcatccgga attccgtatg gcaatgaaag acggtgagct ggtgatatgg gatagtgttc    1380
```

```
accettgtta caccgttttc catgagcaaa ctgaaacgtt ttcatcgctc tggagtgaat   1440
accacgacga tttccggcag tttctacaca tatattcgca agatgtggcg tgttacggtg   1500
aaaacctggc ctatttccct aaagggttta ttgagaatat gtttttcgtc tcagccaatc   1560
cctgggtgag tttcaccagt tttgatttaa acgtggccaa tatggacaac ttcttcgccc   1620
ccgttttcac catgggcaaa tattatacgc aaggcgacaa ggtgctgatg ccgctggcga   1680
ttcaggttca tcatgccgtt tgtgatggct tccatgtcgg cagaatgctt aatgaattac   1740
aacagtactg cgatgagtgg cagggcgggg cgtaaacgcg tggatccggc ttactaaaag   1800
ccagataaca gtatgcgtat ttgcgcgctg atttttgcgg tataagaata tatactgata   1860
tgtatacccg aagtatgtca aaagaggta tgctatgaag cagcgtatta cagtgacagt    1920
tgacagcgac agctatcagt tgctcaaggc atatatgatg tcaatatctc cggtctggta   1980
agcacaacca tgcagaatga agcccgtcgt ctgcgtgccg aacgctggaa agcggaaaat   2040
caggaaggga tggctgaggt cgcccggttt attgaaatga acggctcttt tgctgacgag   2100
aacagggct ggtgaaatgc agtttaaggt ttacacctat aaaagagaga gccgttatcg    2160
tctgtttgtg gatgtacaga gtgatattat tgacacgccc gggcgacgga tggtgatccc   2220
cctggccagt gcacgtctgc tgtcagataa agtctcccgt gaactttacc cggtggtgca   2280
tatcggggat gaaagctggc gcatgatgac caccgatatg ccagtgtgc cggtctccgt    2340
tatcggggaa gaagtggctg atctcagcca ccgcgaaaat gacatcaaaa acgccattaa   2400
cctgatgttc tggggaatat aaatgtcagg ctcccttata cacagccagt ctgcaggtcg   2460
accatagtga ctggatatgt tgtgttttac agtattatgt agtctgtttt ttatgcaaaa   2520
tctaatttaa tatattgata tttatatcat tttacgtttc tcgttcagct ttcttgtaca   2580
aagtggtgat ctagactaga gtcatcagtc aatatgttca ccccaaaaaa gctgtttgtt   2640
aacttgtcaa cctcattcta aaatgtatat agaagcccaa aagacaataa caaaaatatt   2700
cttgtagaac aaaatgggaa agaatgttcc actaaatatc aagatttaga gcaaagcatg   2760
agatgtgtgg ggatagacag tgaggctgat aaaatagagt agagctcaga aacagaccca   2820
ttgatatatg taagtgacct atgaaaaaaa tatggcattt tacaatggga aaatgatgat   2880
ctttttcttt tttagaaaaa cagggaaata tatttatatg taaaaaataa aagggaaccc   2940
atatgtcata ccatacacac aaaaaaaattc cagtgaatta aagtctaaa tggagaaggc    3000
aaaactttaa atcttttaga aaataatata gaagcatgcc atcaagactt cagtgtagag   3060
aaaaatttct tatgactcaa agtcctaacc acaaagaaaa gattgttaat tagattgcat   3120
gaatattaag acttattttt aaaattaaaa aaccattaag aaaagtcagg ccatagaatg   3180
acagaaaata tttgcaacac cccagtaaag agaattgtaa tatgcagatt ataaaaagaa   3240
gtcttacaaa tcagtaaaaa ataaaactag acaaaaattt gaacagatga agagaaact    3300
ctaaataatc attacacatg agaaactcaa tctcagaaat cagagaacta tcattgcata   3360
tacactaaat tagagaaata ttaaaaggct aagtaacatc tgtggcttaa ttaaaacagt   3420
aggatgactg tttaaacctg caggcatgca agcttggcgt aatcatggtc atagctgttt   3480
cctgtgtgaa attgttatcc gctcacaatt ccacacaaca tacgagccgg aagcataaag   3540
tgtaaagcct ggggtgccta atgagtgagc taactcacat taattgcgtt gcgctcactg   3600
cccgctttcc agtcgggaaa cctgtcgtgc cagctgcatt aatgaatcgg ccaacgcgcg   3660
gggagaggcg gtttgcgtat tgggcgctct tccgcttcct cgctcactga ctcgctgcgc   3720
tcggtcgttc ggctgcggcg agcggtatca gctcactcaa aggcggtaat acggttatcc   3780
```

-continued

```
acagaatcag gggataacgc aggaaagaac atgtgagcaa aaggccagca aaaggccagg      3840
aaccgtaaaa aggccgcgtt gctggcgttt ttccataggc tccgcccccc tgacgagcat      3900
cacaaaaatc gacgctcaag tcagaggtgg cgaaacccga caggactata aagataccag      3960
gcgtttcccc ctggaagctc cctcgtgcgc tctcctgttc cgaccctgcc gcttaccgga      4020
tacctgtccg cctttctccc ttcgggaagc gtggcgcttt ctcatagctc acgctgtagg      4080
tatctcagtt cggtgtaggt cgttcgctcc aagctgggct gtgtgcacga accccccgtt      4140
cagcccgacc gctgcgcctt atccggtaac tatcgtcttg agtccaaccc ggtaagacac      4200
gacttatcgc cactggcagc agccactggt aacaggatta gcagagcgag gtatgtaggc      4260
ggtgctacag agttcttgaa gtggtggcct aactacggct acactagaag aacagtattt      4320
ggtatctgcg ctctgctgaa gccagttacc ttcggaaaaa gagttggtag ctcttgatcc      4380
ggcaaacaaa ccaccgctgg tagcggtggt ttttttgttt gcaagcagca gattacgcgc      4440
agaaaaaaag gatctcaaga agatcctttg atcttttcta cggggtctga cgctcagtgg      4500
aacgaaaact cacgttaagg gattttggtc atgagattat caaaaaggat cttcacctag      4560
atccttttaa attaaaaatg aagttttaaa tcaatctaaa gtatatatga gtaaacttgg      4620
tctgacagtt accaatgctt aatcagtgag gcacctatct cagcgatctg tctatttcgt      4680
tcatccatag ttgcctgact ccccgtcgtg tagataacta cgatacggga gggcttacca      4740
tctggcccca gtgctgcaat gataccgcga gacccacgct caccggctcc agatttatca      4800
gcaataaacc agccagccgg aagggccgag cgcagaagtg gtcctgcaac tttatccgcc      4860
tccatccagt ctattaattg ttgccgggaa gctagagtaa gtagttcgcc agttaatagt      4920
ttgcgcaacg ttgttgccat tgctacaggc atcgtggtgt cacgctcgtc gtttggtatg      4980
gcttcattca gctccggttc ccaacgatca aggcgagtta catgatcccc catgttgtgc      5040
aaaaaagcgg ttagctcctt cggtcctccg atcgttgtca gaagtaagtt ggccgcagtg      5100
ttatcactca tggttatggc agcactgcat aattctctta ctgtcatgcc atccgtaaga      5160
tgcttttctg tgactggtga gtactcaacc aagtcattct gagaatagtg tatgcggcga      5220
ccgagttgct cttgcccggc gtcaatacgg gataataccg cgccacatag cagaacttta      5280
aaagtgctca tcattggaaa acgttcttcg gggcgaaaac tctcaaggat cttaccgctg      5340
ttgagatcca gttcgatgta acccactcgt gcacccaact gatcttcagc atcttttact      5400
ttcaccagcg tttctgggtg agcaaaaaca ggaaggcaaa atgccgcaaa aaagggaata      5460
agggcgacac ggaaatgttg aatactcata ctcttccttt ttcaatatta ttgaagcatt      5520
tatcagggtt attgtctcat gagcggatac atatttgaat gtatttagaa aaataaacaa      5580
ataggggttc cgcgcacatt tccccgaaaa gtgccacctg acgtctaaga aaccattatt      5640
atcatgacat aacctataaa aataggcgt atcacgaggc cctttcgtc                  5689
```

<210> SEQ ID NO 6
<211> LENGTH: 394
<212> TYPE: DNA
<213> ORGANISM: Artificial
<220> FEATURE:
<223> OTHER INFORMATION: Synthetic CRE element

<400> SEQUENCE: 6

```
aaataatgat tttattttga ctgatagtga acctgttcgtt gcaacaaatt gatgagcaat      60
gcttttttat aatgccaact ttgtacaaaa aagcaggctt actgtcgaca attgcgtcat      120
```

-continued

| | |
|---|---|
| actgtgacgt ctttcagaca ccccattgac gtcaatggga ttgacgtcaa tggggtgtct | 180 |
| gaaagacgtc acagtatgac ccgggctcga gcctccttgg ctgacgtcag agagagaggc | 240 |
| cggcccctta cgtcagaggc gagaattcga caactttgta tacaaaagtt gaacgagaaa | 300 |
| cgtaaaatga tataaatatc aatatattaa attagatttt gcataaaaaa cagactacat | 360 |
| aatactgtaa aacacaacat atccagtcac tatg | 394 |

```
<210> SEQ ID NO 7
<211> LENGTH: 45
<212> TYPE: DNA
<213> ORGANISM: Artificial
<220> FEATURE:
<223> OTHER INFORMATION: CRE forward primer A

<400> SEQUENCE: 7
```

| | |
|---|---|
| ggggacaagt ttgtacaaaa aagcaggctt agcaccagac agtga | 45 |

```
<210> SEQ ID NO 8
<211> LENGTH: 26
<212> TYPE: DNA
<213> ORGANISM: Artificial
<220> FEATURE:
<223> OTHER INFORMATION: CRE reverse primer B

<400> SEQUENCE: 8
```

| | |
|---|---|
| gggaattcgt tctcccattg acgtca | 26 |

```
<210> SEQ ID NO 9
<211> LENGTH: 26
<212> TYPE: DNA
<213> ORGANISM: Artificial
<220> FEATURE:
<223> OTHER INFORMATION: CRE forward primer C

<400> SEQUENCE: 9
```

| | |
|---|---|
| gggaattcgc accagacagt gacgtc | 26 |

```
<210> SEQ ID NO 10
<211> LENGTH: 45
<212> TYPE: DNA
<213> ORGANISM: Artificial
<220> FEATURE:
<223> OTHER INFORMATION: CRE reverse primer D

<400> SEQUENCE: 10
```

| | |
|---|---|
| ggggacaact tttgtataca aagttgtgtt ctcccattga cgtca | 45 |

```
<210> SEQ ID NO 11
<211> LENGTH: 186
<212> TYPE: DNA
<213> ORGANISM: Artificial
<220> FEATURE:
<223> OTHER INFORMATION: Hybrid CRE sequence

<400> SEQUENCE: 11
```

| | |
|---|---|
| gcttagcacc agacagtgac gtcagctgcc agatcccatg gccgtcatac tgtgacgtct | 60 |
| ttcagacacc ccattgacgt caatgggaga acgaattcgc accagacagt gacgtcagct | 120 |
| gccagatccc atggccgtca tactgtgacg tctttcagac accccattga cgtcaatggg | 180 |
| agaaca | 186 |

```
<210> SEQ ID NO 12
<211> LENGTH: 45
```

```
<212> TYPE: DNA
<213> ORGANISM: Artificial
<220> FEATURE:
<223> OTHER INFORMATION: hGH forward primer

<400> SEQUENCE: 12
ggggacaact ttgtataata aagttggatc ccaaggccca actcc          45

<210> SEQ ID NO 13
<211> LENGTH: 45
<212> TYPE: DNA
<213> ORGANISM: Artificial
<220> FEATURE:
<223> OTHER INFORMATION: hGH reverse primer

<400> SEQUENCE: 13
ggggaccact ttgtacaaga aagctgggta caacaggcat ctact          45

<210> SEQ ID NO 14
<211> LENGTH: 45
<212> TYPE: DNA
<213> ORGANISM: Artificial
<220> FEATURE:
<223> OTHER INFORMATION: TK forward primer

<400> SEQUENCE: 14
ggggacaact ttgtatacaa aagttgtgga acacgcagat gcagt          45

<210> SEQ ID NO 15
<211> LENGTH: 45
<212> TYPE: DNA
<213> ORGANISM: Artificial
<220> FEATURE:
<223> OTHER INFORMATION: TK reverse primer

<400> SEQUENCE: 15
ggggacaact ttgtatagaa aagttgggtg gatctgcggc acgct          45

<210> SEQ ID NO 16
<211> LENGTH: 45
<212> TYPE: DNA
<213> ORGANISM: Artificial
<220> FEATURE:
<223> OTHER INFORMATION: luci forward primer

<400> SEQUENCE: 16
ggggacaact tttctataca aagttgatgg aagatgccaa aaaca          45

<210> SEQ ID NO 17
<211> LENGTH: 45
<212> TYPE: DNA
<213> ORGANISM: Artificial
<220> FEATURE:
<223> OTHER INFORMATION: luci reverse primer

<400> SEQUENCE: 17
ggggacaact ttattataca aagttgttta cacggcgatc ttgcc          45

<210> SEQ ID NO 18
<211> LENGTH: 5550
<212> TYPE: DNA
<213> ORGANISM: Artificial
<220> FEATURE:
<223> OTHER INFORMATION: CreLuc synthetic transgene (Acc65I/PmeI digest)

<400> SEQUENCE: 18
```

-continued

```
gtacccgggg gcgcgccggg atccttaatt aaaattatct ctaaggcatg tgaactggct    60
gtcttggttt tcatctgtac ttcatctgct acctctgtga cctgaaacat atttataatt   120
ccattaagct gtgcatatga tagatttatc atatgtattt tccttaaagg attttttgtaa  180
gaactaattg aattgatacc tgtaaagtct ttatcacact acccaataaa taataaatct   240
ctttgttcag ctctctgttt ctataaatat gtaccagttt tattgttttt agtggtagtg   300
attttattct ctttctatat atatacacac acatgtgtgc attcataaat atatacaatt   360
tttatgaata aaaaattatt agcaatcaat attgaaaacc actgattttt gtttatgtga   420
gcaaacagca gattaaaagg aattcctgca ggatccttaa ttaagttcta gatccaagtt   480
tgtacaaaaa agcaggctta ctgtcgacaa ttgcgtcata ctgtgacgtc tttcagacac   540
cccattgacg tcaatgggat tgacgtcaat ggggtgtctg aaagacgtca cagtatgacc   600
cgggctcgag cctccttggc tgacgtcaga gagagaggcc ggccccttac gtcagaggcg   660
agaattcgac aactttgtat acaaaagttg tggaacacgc agatgcagtc ggggcggcgc   720
ggtcccaggt ccacttcgca tattaaggtg acgcgtgtgg cctcgaacac cgagcgaccc   780
tgcagcgacc cgcttaacag cgtcaacagc gtgccgcaga tccacccaac tttctatac   840
aaagttgcta tggaagatgc caaaaacatt aagaagggcc cagcgccatt ctacccactc   900
gaagacggga ccgccggcga gcagctgcac aaagccatga gcgctacgc cctggtgccc    960
ggcaccatcg cctttaccga cgcacatatc gaggtggaca ttacctacgc cgagtacttc  1020
gagatgagcg ttcggctggc agaagctatg aagcgctatg gctgaatac aaaccatcgg  1080
atcgtggtgt gcagcgagaa tagcttgcag ttcttcatgc ccgtgttggg tgccctgttc  1140
atcggtgtgg ctgtggcccc agctaacgac atctacaacg agcgcgagct gctgaacagc  1200
atgggcatca gccagcccac cgtcgtattc gtgagcaaga aagggctgca aaagatcctc  1260
aacgtgcaaa agaagctacc gatcatacaa aagatcatca tcatggatag caagaccgac  1320
taccagggct tccaaagcat gtacaccttc gtgacttccc atttgccacc cggcttcaac  1380
gagtacgact tcgtgcccga gagcttcgac cgggacaaaa ccatcgccct gatcatgaac  1440
agtagtggca gtaccggatt gcccaagggc gtagccctac cgcaccgcac cgcttgtgtc  1500
cgattcagtc atgcccgcga ccccatcttc ggcaaccaga tcatccccga caccgctatc  1560
ctcagcgtgg tgccatttca ccacggcttc ggcatgttca ccacgctggg ctacttgatc  1620
tgcggctttc gggtcgtgct catgtaccgc ttcgaggagg agctattctt gcgcagcttg  1680
caagactata agattcaatc tgccctgctg gtgcccacac tatttagctt cttcgctaag  1740
agcactctca tcgacaagta cgacctaagc aacttgcacg agatcgccag cggcggggcg  1800
ccgctcagca aggaggtagg tgaggccgtg gccaaacgct tccacctacc aggcatccgc  1860
cagggctacg gcctgacaga aacaaccagc gccattctga tcacccccga aggggacgac  1920
aagcctggcg cagtaggcaa ggtggtgccc ttcttcgagg ctaaggtggt ggacttggac  1980
accggtaaga cactgggtgt gaaccagcgc ggcgagctgt gcgtccgtgg ccccatgatc  2040
atgagcggct acgttaacaa ccccgaggct acaaacgctc tcatcgacaa ggacggctgg  2100
ctgcacagcg gcgacatcgc ctactgggac gaggacgagc acttcttcat cgtggaccgg  2160
ctgaagagcc tgatcaaata caagggctac caggtagccc cagccgaact ggagagcatc  2220
ctgctgcaac accccaacat cttcgacgcc ggggtcgccg gcctgccga cgacgatgcc  2280
ggcgagctgc ccgccgcagt cgtcgtgctg gaacacggta aaaccatgac cgagaaggag  2340
atcgtggact atgtggccag ccaggttaca accgccaaga agctgcgcgg tggtgttgtg  2400
```

-continued

```
ttcgtggacg aggtgcctaa aggactgacc ggcaagttgg acgcccgcaa gatccgcgag    2460
attctcatta aggccaagaa gggcggcaag atcgccgtgt aaacaacttt gtataataaa    2520
gttgctgatc ccaaggccca actccccgaa ccactcaggg tcctgtggac agctcaccta    2580
gctgcaatgg ctacaggtaa gcgcccctaa atcccctttg gcacaatgt gtcctgaggg     2640 gagaggcagc gacctgtaga tgggacgggg gcactaaccc tcaggtttgg ggcttctgaa    2700
tgtgagtatc gccatgtaag cccagtattt ggccaatctc agaaagctcc tggtccctgg    2760
agggatggag agagaaaaac aaacagctcc tggagcaggg agagtgctgg cctcttgctc    2820
tccggctccc tctgttgccc tctggtttct ccccaggctc ccggacgtcc ctgctcctgg    2880
cttttggcct gctctgcctg ccctggcttc aagagggcag tgccttccca accattccct    2940
tatccaggct ttttgacaac gctatgctcc gcgcccatcg tctgcaccag ctggcctttg    3000
acacctacca ggagtttgta agctcttggg gaatgggtgc gcatcagggg tggcaggaag    3060
gggtgacttt cccccgctgg gaaataagag gaggagacta aggagctcag gttttttccc    3120
gaagcgaaaa tgcaggcaga tgagcacacg ctgagtgagg ttcccagaaa agtaacaatg    3180
ggagctggtc tccagcgtag accttggtgg gcggtccttc tcctaggaag aagcctatat    3240
cccaaaggaa cagaagtatt cattcctgca gaaccccag acctccctct gtttctcaga     3300
gtctattccg acaccctcca acagggagga aacacaacag aaatccgtga gtggatgcct    3360
tctccccagg cggggatggg ggagacctgt agtcagagcc cccgggcagc acagccaatg    3420
cccgtccttc ccctgcagaa cctagagctg ctccgcatct ccctgctgct catccagtcg    3480
tggctggagc ccgtgcagtt cctcaggagt gtcttcgcca acagctggt gtacggcgcc     3540 tctgacagca acgtctatga cctcctaaag gacctagagg aaggcatcca aacgctgatg    3600
ggggtgaggg tggcgccagg ggtccccaat cctggagccc cactgacttt gagagctgtg    3660
ttagagaaac actgctgccc tcttttttagc agtcaggccc tgacccaaga gaactcacct    3720
tattcttcat ttcccctcgt gaatcctcca ggcctttctc tacaccctga aggggaggga    3780
ggaaaatgaa tgaatgagaa agggagggaa cagtacccaa gcgcttggcc tctccttctc    3840
ttccttcact ttgcagaggc tggaagatgg cagccccgg actgggcaga tcttcaagca     3900
gacctacagc aagttcgaca caaactcaca caacgatgac gcactactca agaactacgg    3960
gctgctctac tgcttcagga aggacatgga caaggtcgag acattcctgc gcatcgtgca    4020
gtgccgctct gtggagggca gctgtggctt ctagctgccc gggtggcatc cctgtgaccc    4080
ctccccagtg cctctcctgg ccctggaagt tgccactcca gtgcccacca gccttgtcct    4140
aataaaatta agttgcatca ttttgtctga ctaggcgtcc ttctataata ttatggggtg    4200 gagggggggtg gtatgagca aggggcaagt tgggaagaca acctgtaggg cctgcggggt    4260
ctattgggaa ccaagctgga gtgcagtggc acaatcttgg ctcactgcaa tctccgcctc    4320
ctgggttcaa gcgattctcc tgcctcagcc tcccgagttg ttgggattcc aggcatgcat    4380
gaccaggctc agctaatttt tgtttttttg gtagagacgg ggtttcacca tattggccag    4440
gctggtctcc aactcctaat ctcaggtgat ctacccacct tggcctccca aattgctggg    4500
attacaggcg tgaaccactg ctcccttccc tgtccttctg attttaaaat aactatacca    4560
gcaggaggac gtccagacac agcataggct acctggccat gcccaaccgg tgggacattt    4620
gagttgtttg cttggcactg tcctctcatg cgttgggtcc actcagtaga tgcctgttgt    4680
acccagcttt cttgtacaaa gtgggatcta gactagagtc atcagtcaat atgttcaccc    4740
```

-continued

```
caaaaaagct gtttgttaac ttgtcaacct cattctaaaa tgtatataga agcccaaaag    4800
acaataacaa aaatattctt gtagaacaaa atgggaaaga atgttccact aaatatcaag    4860
atttagagca aagcatgaga tgtgtgggga tagacagtga ggctgataaa atagagtaga    4920
gctcagaaac agaccccattg atatatgtaa gtgacctatg aaaaaaatat ggcattttac    4980
aatgggaaaa tgatgatctt tttcttttt agaaaaacag ggaaatatat ttatatgtaa    5040
aaaataaaag ggaacccata tgtcatacca tacacacaaa aaaattccag tgaattataa    5100
gtctaaatgg agaaggcaaa actttaaatc ttttagaaaa taatatagaa gcatgccatc    5160
aagacttcag tgtagagaaa aatttcttat gactcaaagt cctaaccaca agaaaaagat    5220
tgttaattag attgcatgaa tattaagact tattttaaa attaaaaaac cattaagaaa    5280
agtcaggcca tagaatgaca gaaaatattt gcaacacccc agtaaagaga attgtaatat    5340
gcagattata aaagaagtc ttacaaatca gtaaaaaata aaactagaca aaaatttgaa    5400
cagatgaaag agaaactcta aataatcatt acacatgaga aactcaatct cagaaatcag    5460
agaactatca ttgcatatac actaaattag agaaatatta aaaggctaag taacatctgt    5520
ggcttaatta aaacagtagg atgactgttt                                   5550
```

<210> SEQ ID NO 19
<211> LENGTH: 5562
<212> TYPE: DNA
<213> ORGANISM: Artificial
<220> FEATURE:
<223> OTHER INFORMATION: CreLuc hybrid transgene sequence (Acc65I/PmeI digest)

<400> SEQUENCE: 19

```
gtacccgggg gcgcgccggg atccttaatt aaaattatct ctaaggcatg tgaactggct      60
gtcttggttt tcatctgtac ttcatctgct acctctgtga cctgaaacat atttataatt     120
ccattaagct gtgcatatga tagatttatc atatgtattt tccttaaagg atttttgtaa     180
gaactaattg aattgatacc tgtaaagtct ttatcacact acccaataaa taataaatct     240
ctttgttcag ctctctgttt ctataaatat gtaccagttt tattgttttt agtggtagtg     300 atttttattct ctttctatat atatacacac acatgtgtgc attcataaat atatacaatt     360
tttatgaata aaaaattatt agcaatcaat attgaaaacc actgattttt gtttatgtga     420
gcaaacagca gattaaaagg aattcctgca ggatccttaa ttaagttcta gatccaagtt     480
tgtacaaaaa agcaggctta gcaccagaca gtgacgtcag ctgccagatc ccatggccgt     540
catactgtga cgtctttcag acaccccatt gacgtcaatg ggagaacgaa ttcgcaccag     600
acagtgacgt cagctgccag atcccatggc cgtcatactg tgacgtcttt cagacacccc     660
attgacgtca atgggagaac acaactttgt atacaaaagt tgtggaacac gcagatgcag     720
tcggggcggc gcggtcccag gtccacttcg catattaagg tgacgcgtgt ggcctcgaac     780
accgagcgac cctgcagcga cccgcttaac agcgtcaaca gcgtgccgca gatccaccca     840
acttttctat acaaagttgc tatggaagat gccaaaaaca ttaagaaggg cccagcgcca     900
ttctacccac tcgaagacgg gaccgccggc gagcagctgc acaaagccat gaagcgctac     960
gccctggtgc ccggcaccat cgcctttacc gacgcacata tcgaggtgga cattacctac    1020
gccgagtact cgagatgag cgttcggctg gcagaagcta tgaagcgcta tgggctgaat    1080
acaaaccatc ggatcgtggt gtgcagcgag aatagcttgc agttcttcat gcccgtgttg    1140
ggtgccctgt tcatcggtgt ggctgtggcc ccagctaacg acatctacaa cgagcgcgag    1200
```

```
ctgctgaaca gcatgggcat cagccagccc accgtcgtat tcgtgagcaa gaaagggctg    1260
caaaagatcc tcaacgtgca aaagaagcta ccgatcatac aaaagatcat catcatggat    1320
agcaagaccg actaccaggg cttccaaagc atgtacacct tcgtgacttc ccatttgcca    1380
cccggcttca acgagtacga cttcgtgccc gagagcttcg accgggacaa aaccatcgcc    1440
ctgatcatga acagtagtgg cagtaccgga ttgcccaagg gcgtagccct accgcaccgc    1500
accgcttgtg tccgattcag tcatgcccgc gaccccatct tcggcaacca gatcatcccc    1560
gacaccgcta tcctcagcgt ggtgccattt caccacggct tcggcatgtt caccacgctg    1620
ggctacttga tctgcggctt tcgggtcgtg ctcatgtacc gcttcgagga ggagctattc    1680
ttgcgcagct tgcaagacta taagattcaa tctgccctgc tggtgcccac actatttagc    1740
ttcttcgcta agagcactct catcgacaag tacgacctaa gcaacttgca cgagatcgcc    1800
agcggcgggg cgccgctcag caaggaggta ggtgaggccg tggccaaacg cttccaccta    1860
ccaggcatcc gccagggcta cggcctgaca gaaacaacca gcgccattct gatcacccCC    1920
gaaggggacg acaagcctgg cgcagtaggc aaggtggtgc ccttcttcga ggctaaggtg    1980
gtggacttgg acaccggtaa gacactgggt gtgaaccagc gcggcgagct gtgcgtccgt    2040
ggccccatga tcatgagcgg ctacgttaac aaccccgagg ctacaaacgc tctcatcgac    2100
aaggacggct ggctgcacag cggcgacatc gcctactggg acgaggacga gcacttcttc    2160
atcgtggacc ggctgaagag cctgatcaaa tacaagggct accaggtagc cccagccgaa    2220
ctggagagca tcctgctgca acaccccaac atcttcgacg ccggggtcgc cggcctgccc    2280
gacgacgatg ccgcgagct gcccgccgca gtcgtcgtgc tggaacacgg taaaaccatg    2340
accgagaagg agatcgtgga ctatgtggcc agccaggtta caaccgccaa gaagctgcgc    2400
ggtggtgttg tgttcgtgga cgaggtgcct aaaggactga ccggcaagtt ggacgcccgc    2460
aagatccgcg agattctcat taaggccaag aagggcggca agatcgccgt gtaaacaact    2520
ttgtataata aagttgctga tcccaaggcc caactcccCG aaccactcag ggtcctgtgg    2580
acagctcacc tagctgcaat ggctacaggt aagcgcccct aaaatcccTT tgggcacaat    2640
gtgtcctgag gggagaggca gcgacctgta gatgggacgg gggcactaac cctcaggttt    2700
ggggcttctg aatgtgagta tcgccatgta agcccagtat ttggccaatc tcagaaagct    2760
cctggtccct ggagggatgg agagagaaaa acaaacagct cctggagcag ggagagtgct    2820
ggcctcttgc tctccggctc cctctgttgc cctctggttt ctccccaggc tcccggacgt    2880
ccctgctcct ggcttttggc ctgctctgcc tgccctggct tcaagagggc agtgccttcc    2940
caaccattcc cttatccagg cttttgaca acgctatgct ccgcgcccat cgtctgcacc    3000
agctggcctt tgacacctac caggagtttg taagctcttg gggaatgggt gcgcatcagg    3060
ggtggcagga agggtgact ttccccgct gggaaataag aggaggagac taaggagctc    3120
agggtttttc ccgaagcgaa aatgcaggca gatgagcaca cgctgagtga ggttcccaga    3180
aaagtaacaa tgggagctgg tctccagcgt agaccttggt gggcggtcct tctcctagga    3240
agaagcctat atcccaaagg aacagaagta ttcattcctg cagaaccccc agacctccct    3300
ctgtttctca gagtctattc cgacaccctc aacagggag gaaacacaac agaaatccgt    3360
gagtggatgc cttctcccca ggcggggatg ggggagacct gtagtcagag ccccgggca    3420 gcacagccaa tgcccgtcct tcccctgcag aacctagagc tgctccgcat ctccctgctg    3480
ctcatccagt cgtggctgga gcccgtgcag ttcctcagga gtgtcttcgc caacagcctg    3540
gtgtacggcg cctctgacag caacgtctat gacctcctaa aggacctaga ggaaggcatc    3600
```

-continued

```
caaacgctga tgggggtgag ggtggcgcca ggggtcccca atcctggagc cccactgact   3660
ttgagagctg tgttagagaa acactgctgc cctcttttta gcagtcaggc cctgacccaa   3720
gagaactcac cttattcttc atttcccctc gtgaatcctc caggcctttc tctacaccct   3780 gaagggagg gaggaaaatg aatgaatgag aaagggaggg aacagtaccc aagcgcttgg    3840
cctctccttc tcttccttca ctttgcagag gctggaagat ggcagccccc ggactgggca   3900
gatcttcaag cagacctaca gcaagttcga cacaaactca cacaacgatg acgcactact   3960
caagaactac gggctgctct actgcttcag gaaggacatg gacaaggtcg agacattcct   4020
gcgcatcgtg cagtgccgct ctgtggaggg cagctgtggc ttctagctgc ccgggtggca   4080
tccctgtgac ccctccccag tgcctctcct ggccctggaa gttgccactc cagtgcccac   4140
cagccttgtc ctaataaaat taagttgcat cattttgtct gactaggcgt ccttctataa   4200
tattatgggg tggagggggg tggtatggag caaggggcaa gttgggaaga caacctgtag   4260
ggcctgcggg gtctattggg aaccaagctg gagtgcagtg gcacaatctt ggctcactgc   4320
aatctccgcc tcctgggttc aagcgattct cctgcctcag cctcccgagt tgttgggatt   4380
ccaggcatgc atgaccaggc tcagctaatt tttgtttttt tggtagagac ggggtttcac   4440
catattggcc aggctggtct ccaactccta atctcaggtg atctacccac cttggcctcc   4500
caaattgctg ggattacagg cgtgaaccac tgctcccttc cctgtccttc tgattttaaa   4560
ataactatac cagcaggagg acgtccagac acagcatagg ctacctggcc atgcccaacc   4620
ggtgggacat ttgagttgtt tgcttggcac tgtcctctca tgcgttgggt ccactcagta   4680
gatgcctgtt gtacccagct ttcttgtaca aagtgggatc tagactagag tcatcagtca   4740
atatgttcac cccaaaaaag ctgtttgtta acttgtcaac ctcattctaa aatgtatata   4800
gaagcccaaa agacaataac aaaaatattc ttgtagaaca aaatgggaaa gaatgttcca   4860
ctaaatatca agatttagag caaagcatga gatgtgtggg gatagacagt gaggctgata   4920
aaatagagta gagctcagaa acagacccat tgatatatgt aagtgaccta tgaaaaaaat   4980
atggcatttt acaatgggaa aatgatgatc ttttctttt ttagaaaaac agggaaatat    5040
atttatatgt aaaaaataaa agggaaccca tatgtcatac catacacaca aaaaaattcc   5100
agtgaattat aagtctaaat ggagaaggca aaactttaaa tcttttagaa aataatatag   5160
aagcatgcca tcaagacttc agtgtagaga aaaatttctt atgactcaaa gtcctaacca   5220
caaagaaaag attgttaatt agattgcatg aatattaaga cttattttta aaattaaaaa   5280
accattaaga aaagtcaggc catagaatga cagaaaatat ttgcaacacc ccagtaaaga   5340
gaattgtaat atgcagatta taaaagaag tcttacaaat cagtaaaaaa taaaactaga    5400 caaaatttg aacagatgaa agagaaactc taaataatca ttacacatga gaaactcaat   5460
ctcagaaatc agagaactat cattgcatat acactaaatt agagaaatat taaaaggcta   5520
agtaacatct gtggcttaat taaaacagta ggatgactgt tt                     5562
```

<210> SEQ ID NO 20
<211> LENGTH: 24
<212> TYPE: DNA
<213> ORGANISM: Artificial
<220> FEATURE:
<223> OTHER INFORMATION: Luc2-forward primer

<400> SEQUENCE: 20

```
gaagatgcca aaaacattaa gaag                                          24
```

```
<210> SEQ ID NO 21
<211> LENGTH: 20
<212> TYPE: DNA
<213> ORGANISM: Artificial
<220> FEATURE:
<223> OTHER INFORMATION: Luc2-reverse primer

<400> SEQUENCE: 21
gatcttttgc agccctttct                                                    20
```

TRANSGENIC NON-HUMAN ANIMAL AND USES THEREOF

FIELD OF THE INVENTION

The present invention relates generally to transgene constructs, transgenic non-human animals comprising transgene constructs, methods of making and methods of using the transgenic non-human animals comprising transgene constructs. An embodiment of the invention relates to methods of assaying for GPCR ligands non-invasively in whole animals, tissue slices, or in native cells using a transgenic model containing a bioluminescent transgene reporter system that is responsive to pathway modulation following ligand binding to GPCR receptors.

BACKGROUND OF THE INVENTION

In drug development, attrition rates are high with only one in five compounds making it through development to Food and Drug Administration approval (FDA) (DiMasi, J A, et al, J Health Econ 22,151-185, 2003). Moreover, despite dramatically increased investment, the rate of introduction of novel drugs has remained relatively constant over the past 30 years, with only two to three advances in new drug classes per year eventually making it to market (Lindsay M A, Nature Rev Drug Discovery, 2, 831-838, 2003).

Molecular and functional imaging applied to the initial stages of drug development can provide evidence of biological activity and confirm the putative drug having an effect on its intended target. Thus, there is considerable expectation that investment in molecular imaging technology will enhance drug development (Rudin M, Progress in Drug Res vol 62). The advantage of molecular imaging techniques over more conventional readouts is that they can be performed in the intact organism with sufficient spatial and temporal resolution for studying biological processes in vivo. Furthermore, it allows a repetitive, non-invasive, uniform and relatively automated study of the same biological model at different time points, thus increasing the statistical power of longitudinal studies plus reducing the number of animals required and thereby reducing cost of drug development.

Molecular Imaging

Molecular imaging refers to the convergence of approaches from various disciplines (cell and molecular biology, chemistry, medicine, pharmacology, physics, bioinformatics and engineering) to exploit and integrate imaging techniques in the evaluation of specific molecular processes at the cellular and sub-cellular levels in living organism. (Massoud T. F., Genes Dev. 17:545-580, 2003)

The advent of genetic engineering has brought about major changes to applied science, including for example the drug discovery pipeline. In the same way, the development and exploitation of animal imaging procedures is providing new means for pre-clinical studies (Maggie A. and Ciana P., Nat. Rev. Drug Discov. 4, 249-255, 2005). Animal models traditionally have been cumbersome because of the difficulty in quantifying physiological events in real-time. Over the years new imaging methods have been developed to overcome this difficulty, such as magnetic resonance imaging (MRI) and positron emission tomography (PET). More recently bioluminescence imaging based on in vivo expression of luciferase, the light-emitting enzyme of the firefly, has been used for non-invasive detection.

Molecular Imaging: Bioluminescence

In vivo bioluminescent imaging (BLI) is a sensitive tool that is based on detection of light emission from cells or tissues. The utility of reporter gene technology makes it possible to analyze specific cellular and biological processes in a living animal through in vivo imaging methods. Bioluminescence, the enzymatic generation of visible light by a living organism, is a naturally occurring phenomenon in many non-mammalian species (Contag, C. H., et al, Mol. Microbiol. 18:593-603, 1995). Luciferases are enzymes that catalyze the oxidation of a substrate to release photons of light (Greer L. F., Ill, Luminescence 17:43-74, 2002). Bioluminescence from the North American firefly is the most widely studied. The firefly luciferase gene (luc) expression produces the enzyme luciferase which converts the substrate D-luciferin to non-reactive oxyluciferin, resulting in green light emission at 562 nm. Because mammalian tissues do not naturally emit bioluminescence, in vivo BLI has considerable appeal because images can be generated with very little background signal.

BLI requires genetic engineering of cells or tissues with an expression cassette consisting of the bioluminescent reporter gene under the control of a selected gene promoter constitutively driving the light reporter (FIG. 3). In order to induce light production, the substrates such as luciferin are administered by intracerebroventricular (icv), intravenous (iv), intraperitoneal (ip) or subcutaneous (sq) injection.

The light emitted by luciferase is able to penetrate tissue depths of several millimeters to centimeters; however photon intensity decreases 10 fold for each centimeter of tissue depth (Contag, C. H., et al, Mol. Microbiol. 18:593-603, 1995). Sensitive light-detecting instruments must be used to detect bioluminescence in vivo. The detectors measure the number of photons emitted per unit area. Low levels of light at wavelengths between 400 and 1000 nm can be detected with charge coupled device cameras that convert the light photons that strike silicon wafers into electrons (Spibey C P et al electrophoresis 22:829-836, 2001). The software is able to convert electron signals into a two-dimensional image. The software is also able to quantify the intensity of the emitted light (number of emitted photons striking the detectors) and convert these numerical values into a pseudocolor graphic or grayscale image (FIGS. 2A and 2B). The actual data is measured in photons, but the pseudocolor graphic enables rapid visual interpretation. Quantitative measurements within a region of interest may be necessary for more subtle differences. The use of cooled charge coupled device (CCD) cameras reduces the thermal noise and a light-tight box allows luciferase-produced light to be optimally visualized and quantified (Contag C. H. and Bachmann, M. H., Annu. Rev. Biomed. Eng. 4:235-260, 2002). It is useful to have the luciferase image superimposed on another type of image such as an autograph or radiograph for anatomical location of the emission signal (FIG. 2B). The software superimposes images for visualization and interpretation.

By combining animal engineering with molecular imaging techniques, it has become possible to conduct dynamic studies on specific molecular processes in living animals. This approach could potentially impact on pre-clinical protocols thus widely changing all aspects of medicine (Maggie A. Trends Pharmacolo. Sci 25, 337-342, 2004)

G-Protein Coupled Receptors (GPCRs)—GPCRs as Drug Targets

GPCRs constitute a large super family of cell surface receptors that are classified into more than 100 subfamilies on the basis of their shared topological structure; GPCRs are also referred to as seven transmembrane (7TM) receptors. GPCRs are the most frequently addressed drug targets in the pharmaceutical industry. Approximately 30% of all marketed prescription drugs target GPCRs, which makes this protein family pharmaceutically the most successful target class (Jacoby, E; Chem. Med. Chem., 1: 761-782, 2006).

The interaction between GPCRs and their extracellular ligands has proven to be an attractive point of interference for therapeutic agents. For this reason, the pharmaceutical industry has developed biochemical drug discovery assays to investigate these ligand-GPCR interactions. Interaction of an activated GPCR with a heterotrimeric G-protein catalyzes the exchange of guanosine diphosphate (GDP) by guanosine triphosphate (GTP) enabling the interaction with several downstream effectors (Cabrera-Vera T. M., Endocr. Rev. 24:765-781, 2003). Signaling downstream is dependent on the G-alpha isoform that is preferred by the GPCR of interest. Proteins of the G-alpha$_{q/11}$ family stimulate phospholipase C (PLC), while representatives of the G-alpha$_{i/o}$ and G-alpha$_s$ families mostly modulate adenylate cyclase (AC) activity. If the GPCR of interest signals via PLC, then the most broadly applied reporter based technique to measure GPCR activation is a calcium ($Ca^{+2}$) release assay, either measured in a fluorescent format using $Ca^{+2}$-sensitive fluorophores (Sullivan E, Methods Mol. Biol. 114:125-133, 1999) or in a luminescent format using aequorin and a chemiluminescent substrate (Dupriez V. J., Receptors Channels 8: 319-330, 2002). If the GPCR of interest signals via AC, then cytosolic cyclic adenosine monophosphate (cAMP) content may be determined using various detection technologies (Gabriel D. Assay Drug Dev. Technol. 1:291-303, 2003)

GPCR reporter based assays have been extensively used in current drug discovery programs. Typically, GPCR reporters have been introduced into cell based systems to support in vitro high-throughput screening (HTS) of large pharmaceutical libraries to identify ligands or compounds that activate or module the specific GPCR. Secondary and follow-up cell based assays confirm and refine any "hits" identified in HTS against a specific GPCR; but again, these assays rely on recombinant DNA methods to introduce a cloned GPCR into a transformed cell type. While transformed cell types have excellent proliferative capacity to support large screening programs, they often display aberrant genetic and functional characteristics and consequently significant attrition of putative "hits" from HTS is encountered using this paradigm.

For several years, bioluminescence-based reporter gene assays have been employed to measure functional activity of GPCRs (Hill, S. J. Curr. Opin. Pharmacol 1: 526-532, 2001). This assay format is very sensitive owing to the low signal background of the bioluminescent readout and the signal amplifications steps between GPCR activation and the cumulative reporter gene expression.

A cAMP response element (CRE) in the promoter of the reporter gene enables the specific monitoring of G protein dependent signaling. When a ligand binds to the GPCR it causes a conformational change in the GPCR which allows it to activate an associated G-protein. The enzyme adenylate cyclase is a cellular protein that can be regulated by G-proteins. Adenylate cyclase activity is either activated or inhibited when it binds to a subunit of the activated G protein. Signal transduction depends on the type of G protein. Adenylate cyclase acts to either increase or decrease cAMP production in the cell. The cAMP produced is a second messenger in cellular metabolism and is an allosteric activator to protein kinase A (PKA). When there is no cAMP, the PKA complex is inactive. When cAMP binds to the regulatory subunits of PKA, their conformation is altered, causing the dissociation of the regulatory subunits, which activates protein kinase A and allows further biological effects. PKA then phosphorylates and activates the transcription factor CREB. CREB binds to certain DNA sequences called cAMP response elements (CRE) and thereby increases or decreases transcription, and thus the expression, of certain genes, such as the luciferase reporter gene.

The CreLuc transgene is designed to assay activation of all three major GPCRs either directly through the cAMP intracellular signaling pathway or indirectly through signaling via PLC. Because any one cell type contains many different types of GPCRs on their cell surface, (thus any cell would have GPCRs signaling via G-alpha$_{q/11}$, G-alpha$_{i/o}$ and G-alpha$_s$ occurring simultaneously within a cell) conventional wisdom would suggest that it would be improbable that a transgene such as CreLuc would be specific enough to discriminate any one specific GPCR ligand. However, we demonstrate here the CreLuc transgene is able to discriminate GPCR ligands. We predict that the bioluminescent signal for the luciferase reporter in cells, tissues slices, or the whole animal will be increased with forskolin and be modulated by ligands for Gs, Gq or Gi receptors. Table 1 shows the anticipated effect that GPCR activation/inhibition will have on the CreLuc reporter system upon binding to a GPCR ligand. Further, we show data that our novel CreLuc reporter system can discriminate different classes of GPCR ligands and that such a reporter system is applicable for identifying novel GPCR ligands when used in cells, tissue slices and the whole animal.

TABLE 1

Predicted change in bioluminescent signal from the CreLuc reporter upon ligand binding to specific GPCRs

| Receptor Type | Agonist | Antagonist; Inverse Agonist |
|---|---|---|
| Gs; Gq | Increase | Decrease |
| Gi | Decrease | Increase |

A GPCR Bioimaging Reporter Transgenic Model

Significant attrition of potential drug candidates in the current drug discovery paradigm is encountered in the phase transition from cell-based reporter assays to in vivo models. Numerous in vivo models are available that recapitulate either all or part of a particular human disease. Demonstrating lead compound activity in these models is a significant milestone for progression of new chemical GPCR drugs. Animal disease models typically require a large number of animals and time to allow for the development of their phenotype and an accurate assay of the candidate compound's impact on altering the disease outcome. Following in vitro testing, the next level of testing a drug candidate in a complex system is using in vivo testing or in vivo models of disease states which are mechanistic based. Failures to alter the induced disease outcomes are poorly understood but yet result in the large attrition rates of candidate compounds in the drug development pipeline.

A transgenic model containing a GPCR ligand binding and activation reporter assay would be a significant improvement in the current drug discovery paradigm for GPCRs. For instance, an embodiment of this invention describes a transgene containing the cAMP reporter assay based on a luciferase reporter (CreLuc) that is combined with molecular imaging in whole animals, tissues, or cells which would significantly accelerate GPCR ligand drug discovery (Bhaumik, S. and Gambhir, S. S., Proc. Natl. Acad. Sci. USA, 99:377-382 2002; Hasan M. T., et al., Genesis 29:116-122, 2001). As described herein, embodiments of the transgenic non-human animal of the instant invention offer the following non-limiting advantages:

1. Tissues or cell based assays have the same reporter system as in the transgenic in vivo model assay thus reducing the number of unknowns in complex intact biological systems.
2. Non-invasive imaging allows quantitative analysis of ligand or compound activity in a time-course assay in the same animal.
3. Non-invasive imaging reduces the number of animals per study and leads to greater statistical power by each animal being its own control wherein the control would be the animal assayed at time zero.
4. The transgenic animal would be a source of cells and tissues to support parallel assays done in vitro or ex vivo.
5. The assay of the transgenic animal would support the assay of ligand activity in native cell types which leads to a more realistic profile of ligand: receptor interaction.
6. The transgenic animal allows for simultaneous assessment of pharmacodynamics and pharmacokinetics of GPCR ligands.
7. The transgenic animal allows for simultaneously identification of tissue and cell-type specificity at either the organ or whole animal level.
8. The transgenic animal allows for cross breeding with other genetically altered models to reveal novel signaling pathways and their response to specific ligands.

Many transgenic animals engineered with different reporters are being employed in the study of molecular processes such as drug metabolism (Zhang W., et al. Drug Metab. Dispos. 31:1054-1064, 2003), genotoxicity (Gossen J. A., et al., Proc. Natl. Acad. Sci. USA 86:7971-7975, 1989) and the effects of toxic compounds (Sacco M. G. et al., Nat. Biotechnol 15:1392-1397, 1997). To achieve their design goals, a GPCR reporter animal suitable for molecular imagining studies has to incorporate several elements arranged to allow both high levels of reporter expression to support a large window of bioluminescent detection as well as expression in every cell type to support broad acute in vivo assays on biodistribution of the ligand or compound under study.

The complexity and diversity of the mechanisms involved in gene expression will never allow researchers to construct genes capable in all cases of being expressed in transgenic animals in a fully predictable manner (Pinkert, C. A. (ed.) 1994. Transgenic animal technology: A laboratory handbook. Academic Press, Inc., San Diedo, Calif.; Monastersky G. M. and Robl, J. M. (ed.) (1995) Strategies in Transgenic Animal Science. ASM Press. Washington D.C). Only through extensive trial and error can unique combinations of transgene structures be arrived at to deliver model design goals as required for bioimaging of GPCR reporters.

Utility of a Transgenic GPCR Reporter over Recombinant Cell Assays

As screening technology advances to the point of understanding the behaviors of individual GPCRs, it is clear that rather than being on-off switches, these receptors are acting more as microprocessors of information. This has introduced the phenomenon of functional selectivity, whereby certain ligands initiate only portions of the signaling mechanism mediated by a given receptor, which has opened new horizons for drug discovery. The need to discover new GPCR ligand relationships and quantify the effect of the drug on these complex systems to guide medicinal chemistry puts significantly higher demands on any pharmacological reporter assay. This concept drives the return to whole-system assays from the reductionist recombinant cell based screening systems. Profiling a ligand's activity with a specific GPCR or set of GPCRs in a native cellular environment is expected to improve the success rate of identifying new drugs against a key class of pharmaceutically important receptors (Kenakin T P, Nat. Rev. Drug Discov. 8,617-625, 2009) An animal model containing a bioluminescent GPCR reporter transgene is a highly desirable molecular imaging strategy to define GPCR ligand activity in an intact biologically complex system with the goal of improving drug discovery to fight human diseases.

Because activation of CRE/CREB is involved many varied biological processes, there has been considerable interest in studying the activation of CRE by using a CRE/CREB reporter expression system. Cyclic adenosine monophosphate (cAMP) is a second messenger in intracellular signal transduction following receptor activation and subsequent activation of protein kinase, thereby being involved in the regulation of many biological processes. CREB (cAMP responsive element binding protein), phosphorylated by kinase activated by cAMP, binds to the cAMP responsive element (CRE) in the promoter region of many genes and activates transcription (Shaywitz and Greenberg, Annul. Rev. Biochem., 68:821-861, 1999). Transgenic mice carrying six tandem CREs with a minimal herpes simplex virus (HSV) promoter driving beta-galactosidase expression were used to study CRE-mediated gene expression in brain slices in response to chronic antidepressant treatment (Thome J., et al., J. Neurosci. 20:4030-4036, 2000). Similarly, transgenic mice carrying four copies of rat somatostatin gene promoter CRE fused to a thymidine kinase promoter and the luciferase gene have been used to study CRE activation in histological brain slices or homogenates (Boer et al, PloS One, May 9; 2(5): e431, 2007). However, studies to date have been hampered by the need to screen large numbers of transgenic lines to find a suitable animal model. Further, after the appropriate line has been identified, relatively low reporter expression levels require the transgenic animal be euthanized in order to measure the reporter gene, thus requiring large number of animals be used to in a single experimental paradigm.

An embodiment of the invention is the development of a transgene comprising insulator elements, response elements, promoter elements, reporter genes, and functional elements. The transgene can be quickly introduced into non-human animals because of its high rate of integration and high level of reporter gene expression, thus transgenic animals can be easily developed as models to study regulatory element activation in vivo (i.e., in the living animal), in situ (e.g., brain slices, intact whole organ) or in vitro (e.g., primary cells cultured from the transgenic animal, tissue homogenates).

An embodiment of the invention is a transgene comprising a CRE Luc reporter system used in transgenic non-human animals as models to quantify GPCR ligand activities through the regulation of intracellular cAMP levels in vivo. As a non-limiting example, we have demonstrated changes in the luciferase reporter via bioluminescence in isolated primary cells and in whole animals using general cAMP regulators. In another embodiment, activation of the reporter has been assayed and confirmed in tissue extracts using luciferase assays ex vivo. The response of the CRE Luc transgene has been documented in multiple mouse lines and exhibits either single or multiple tissue activation profiles. Furthermore, as non-limiting examples, we demonstrate that specific GPCR ligands activated the CRE Luc transgene in whole animals, tissue slices, and primary cells.

BRIEF SUMMARY OF THE INVENTION

In general, the invention provides transgene constructs, transgenic non-human animals comprising transgene constructs, methods of making and methods of using the transgenic non-human animals comprising transgene constructs.

An embodiment of the invention provides a transgene construct comprising the CRE Luc reporter system. An embodiment of the invention is the introduction of the transgene construct comprising the CRE Luc reporter system into a non-human animal.

Since cAMP modulation is a key activation pathway for GPCRs, the invention serves as a platform for quantifying in whole animals, tissue slices, or cells the activation of a GPCR by a ligand or compound through the activation of a reporter gene wherein the reporter gene provides for a measurable bioluminescent signal, for example, metabolism of luciferin by luciferase. This invention supplies tools to improve the transition of new drug discovery entities such as ligands or compounds from cell based assays to whole animals. An embodiment of the invention uses the same reporter system in native cells which will reduce the attrition rate for new GPCR ligands while simultaneously supplying bioavailability data.

An embodiment of the invention is a transgenic non-human animal having a genome comprising a transgene comprising a first insulator element, a response element, a promoter, a bioluminescent reporter, a functional element and a second insular element.

An embodiment of the invention is a transgenic non-human animal wherein the first insulator element is selected from the group consisting of matrix attachment regions (MAR), DNase I-hypersensitive site (HS4) and inverted terminal repeats (ITR). A further embodiment of the invention is a transgenic non-human animal wherein the second insulator element is selected from the group consisting of matrix attachment element (MAR), HS4 and ITR. A further embodiment of the invention is a transgenic non-human animal wherein the first insulator element is the same as the second insulator element.

An embodiment of the invention encompasses a transgenic non-human animal wherein the response element is selected from the group consisting of cAMP response element (CRE), activator protein 1 (ASP1), glucocorticoid response element (GRE), heat shock response element (HSE), serum response element (SRE), thyroid response element (TRE) and estrogen response element (ERE). A further embodiment of the invention is a transgenic non-human animal wherein the response element is repeated in tandem two to twenty-four times. A further embodiment of the invention is a transgenic non-human animal wherein the response element is repeated in tandem six times. A further embodiment of the invention is a transgenic non-human animal wherein the response element is CRE, further wherein the CRE response element may be a single element or repeated two to twenty-four times.

An embodiment of the invention is a transgenic non-human animal wherein the promoter is herpes simplex virus thymidine kinase minimal (HSV TK min).

An embodiment of the invention is a transgenic non-human animal wherein the bioluminescent reporter is selected from the group consisting of luciferase, chloramphenicol acetyltransferase (CAT), beta-galactosidase, secreted alkaline phosphatase (SEAP), human growth hormone (HGH) and green fluorescent protein (GFP).

An embodiment of the invention is a transgenic non-human wherein the functional element is human growth hormone (hGH) gene.

An embodiment of the invention is a transgenic non-human wherein the transgene comprises SEQ ID NO: 18.

An embodiment of the invention is a transgenic non-human wherein the transgene comprises SEQ ID NO: 19.

An embodiment of the invention is a cell isolated from the transgenic non-human animal or a tissue slice isolated from the transgenic non-human animal of claim 1.

An embodiment of the invention is a method of identifying a G protein-coupled receptor (GPCR) ligand, the method comprising (a) measuring an amount of bioluminescence in the transgenic non-human animal disclosed herein; (b) administering a test agent to the transgenic non-human animal; (c) measuring an amount of bioluminescence of the transgenic non-human animal at one or more time points following administration of the test agent; and (d) comparing the amount of bioluminescence measured in (a) to the amount of bioluminescence measured in (c) wherein a difference in the amount of bioluminescence in (a) compared to (c) identifies the test agent as a GPCR ligand.

An embodiment of the invention is a method of identifying a G protein-coupled receptor (GPCR) ligand, the method comprising (a) preparing a tissue slice from the transgenic non-human animal disclosed herein; (b) measuring an amount of bioluminescence in the tissue slice; (c) administering a test agent to the tissue slice; (d) measuring an amount of bioluminescence of the tissue slice at one or more time points following administration of the test agent; and (e) comparing the amount of bioluminescence measured in (b) to the amount of bioluminescence measured in (d) wherein a difference in the amount of bioluminescence in (b) compared to (d) identifies the test agent as a GPCR ligand.

An embodiment of the invention is a method of identifying a G protein-coupled receptor (GPCR) ligand, the method comprising (a) preparing a cell isolated from the transgenic non-human animal disclosed herein; (b) measuring an amount of bioluminescence in the cell; (c) administering a test agent to the cell; (d) measuring an amount of bioluminescence in the cell at one or more time points following administration of the test agent; and (e) comparing the amount of bioluminescence measured in (b) to the amount of bioluminescence measured in (d) wherein a difference in the amount of bioluminescence in (b) compared to (d) identifies the test agent as a GPCR ligand.

An embodiment of the invention is a method of monitoring GPCR function in a non-human animal, the method comprising (a) transgenically modifying a non-human animal to express a transgene comprising a first insulator element, a response element, a promoter, a bioluminescent reporter, a functional element and a second insular element; (b) monitoring bioluminescence from the non-human animal; and (c) correlating said bioluminescence to GPCR function.

An embodiment of the invention is a method of monitoring GPCR function in a non-human animal, the method comprising (a) transgenically modifying a non-human animal to express a transgene comprising a first insulator element, a response element, a promoter, a bioluminescent reporter, a functional element and a second insular element; (b) monitoring luciferase from the non-human animal; and (c) correlating said bioluminescence to GPCR function.

An embodiment of the invention is a method of monitoring GPCR function in a non-human animal, the method comprising (a) transgenically modifying a non-human animal to express a transgene comprising a first insulator element, a response element, a promoter, a bioluminescent reporter, a functional element and a second insular element; (b) manipulating the non-human animal to mimic an aspect of a disease state; (c) monitoring bioluminescence from the non-human animal; and (d) correlating said bioluminescence to GPCR function.

An embodiment of the invention is a method of monitoring GPCR function in a non-human animal, the method comprising (a) transgenically modifying a non-human animal to express a transgene comprising a first insulator element, a response element, a promoter, a bioluminescent reporter, a functional element and a second insular element; (b) manipulating the non-human animal to mimic an aspect of a disease state; (c) monitoring luciferase from the non-human animal; and (d) correlating said bioluminescence to GPCR function.

An embodiment of the invention is a method of making a non-human transgenic animal for use in monitoring GPCR function, the method comprising (a) transgenically modifying a non-human animal to express a transgene comprising a first insulator element, a response element, a promoter, a bioluminescent reporter, a functional element and a second insular element; (b) measuring an amount of bioluminescence in the transgenic non-human animal of (a); (c) administering a GPCR ligand to the transgenic non-human animal; (d) measuring an amount of bioluminescence of the transgenic non-human animal at one or more time points following administration of the GPCR ligand; and (e) comparing the amount of bioluminescence measured in (b) to the amount of bioluminescence measured in (d) wherein a difference in the amount of bioluminescence in (b) compared to (d) identifies the non-human transgenic animal for use in monitoring GPCR function.

An embodiment of the invention is a method of identifying a compound that modulates a G protein-coupled receptor (GPCR), the method comprising (a) preparing a cell isolated from the transgenic non-human animal disclosed herein; (b) measuring an amount of bioluminescence in the cell; (c) administering a test agent to the cell; (d) measuring an amount of bioluminescence in the cell at one or more time points following administration of the test agent; and (e) comparing the amount of bioluminescence measured in (b) to the amount of bioluminescence measured in (d) wherein a difference in the amount of bioluminescence in (b) compared to (d) identifies the test agent as a GPCR ligand.

An embodiment of the invention is a method of identifying a compound that modulates a G protein-coupled receptor (GPCR), the method comprising (a) providing cells isolated from the transgenic non-human animal disclosed herein into one or more receptacles; (b) administering a control to one or more receptacles; (c) administering a test agent to one or more receptacles; and (d) measuring an amount of luciferase in the receptacles, wherein a difference in the amount of luciferase measured in the receptacle(s) comprising control compared to the amount of luciferase in the receptacle(s) comprising test agent indicates the compound as modulating a GPCR.

An embodiment of the invention is a method of identifying a compound that modulates a G protein-coupled receptor (GPCR), the method comprising (a) providing cells isolated from the transgenic non-human animal disclosed herein into one or more receptacles; (b) administering a general cAMP modulator to one or more receptacles; (c) administering a test agent to one or more receptacles; and (d) measuring an amount of luciferase in the receptacles, wherein a difference in the amount of luciferase measured in the receptacle(s) comprising only the general cAMP modulator is compared to the amount of luciferase in the receptacle(s) comprising the general cAMP modulator and the test agent indicates the compound as modulating a GPCR.

An embodiment of the invention is a method of identifying a compound that modulates a G protein-coupled receptor (GPCR), the method comprising (a) providing tissue slices isolated from the transgenic non-human animal disclosed herein into one or more receptacles; (b) administering a control to one or more receptacles; (c) administering a test agent to one or more receptacles; and (d) measuring an amount of luciferase in the receptacles, wherein a difference in the amount of luciferase measured in the receptacle(s) comprising control compared to the amount of luciferase in the receptacle(s) comprising test agent indicates the compound as modulating a GPCR.

An embodiment of the invention is a method of identifying a compound that modulates a G protein-coupled receptor (GPCR), the method comprising (a) providing tissue slices isolated from the transgenic non-human animal disclosed herein into one or more receptacles; (b) administering a general cAMP modulator to one or more receptacles; (c) administering a test agent to one or more receptacles; and (d) measuring an amount of luciferase in the receptacles, wherein a difference in the amount of luciferase measured in the receptacle(s) comprising only the general cAMP modulator is compared to the amount of luciferase in the receptacle(s) comprising the general cAMP modulator and the test agent indicates the compound as modulating a GPCR.

An embodiment of the invention is a method of identifying a compound that modulates a G protein-coupled receptor (GPCR), the method comprising (a) providing cells isolated from the transgenic non-human animal disclosed herein into one or more receptacles; (b) administering a cell stimulator to one or more receptacles; (c) administering a test agent to one or more receptacles; and (e) measuring an amount of luciferase in the receptacles, wherein a difference in the amount of luciferase measured in the receptacle(s) comprising cell stimulator compared to the amount of luciferase in the receptacle(s) comprising test agent and cell stimulator indicates the compound as modulating a GPCR.

An embodiment of the invention is a method of identifying a compound that modulates a G protein-coupled receptor (GPCR), the method comprising (a) providing cells isolated from the transgenic non-human animal disclosed herein into one or more receptacles; (b) administering a cell stimulator to one or more receptacles; (c) administering a general cAMP modulator to one or more receptacles; (d) administering a test agent to one or more receptacles; and (e) measuring an amount of luciferase in the receptacles, wherein a difference in the amount of luciferase measured in the receptacle comprising the cell stimulator and general cAMP modulator is compared to the amount of luciferase in the receptacle(s) comprising the cell stimulator and general cAMP modulator and the test agent indicates the compound as modulating a GPCR.

An embodiment of the invention is a method of identifying a compound that modulates a G protein-coupled receptor (GPCR), the method comprising (a) providing tissue slices isolated from the transgenic non-human animal disclosed herein into one or more receptacles; (b) administering a cell stimulator to one or more receptacles; (c) administering a test agent to one or more receptacles; and (d) measuring an amount of luciferase in the receptacles, wherein a difference in the amount of luciferase measured in the receptacle(s) comprising cell stimulator compared to the amount of luciferase in the receptacle(s) comprising test agent and cell stimulator indicates the compound as modulating a GPCR.

An embodiment of the invention is a method of identifying a compound that modulates a G protein-coupled receptor (GPCR), the method comprising (a) providing tissue slices isolated from the transgenic non-human animal disclosed herein into one or more receptacles; (b) administering a cell stimulator to one or more receptacles; (c) administering a general cAMP modulator to one or more receptacles; (d) administering a test agent to one or more receptacles; and (e) measuring an amount of luciferase in the receptacles, wherein a difference in the amount of luciferase measured in the receptacle comprising the cell stimulator and general cAMP modulator is compared to the amount of luciferase in the receptacle(s) comprising the cell stimulator and general cAMP modulator and the test agent indicates the compound as modulating a GPCR.

BRIEF DESCRIPTION OF THE DRAWINGS

FIG. 26 shows induction of luciferase in different tissues by the adrenoceptor beta3 (Adrb3) agonist, CL316,243 (1 mg/kg, ip) in CRE-Luc mice. The luciferase assay was performed in tissue homogenates.

DETAILED DESCRIPTION OF THE INVENTION

Figure 1:
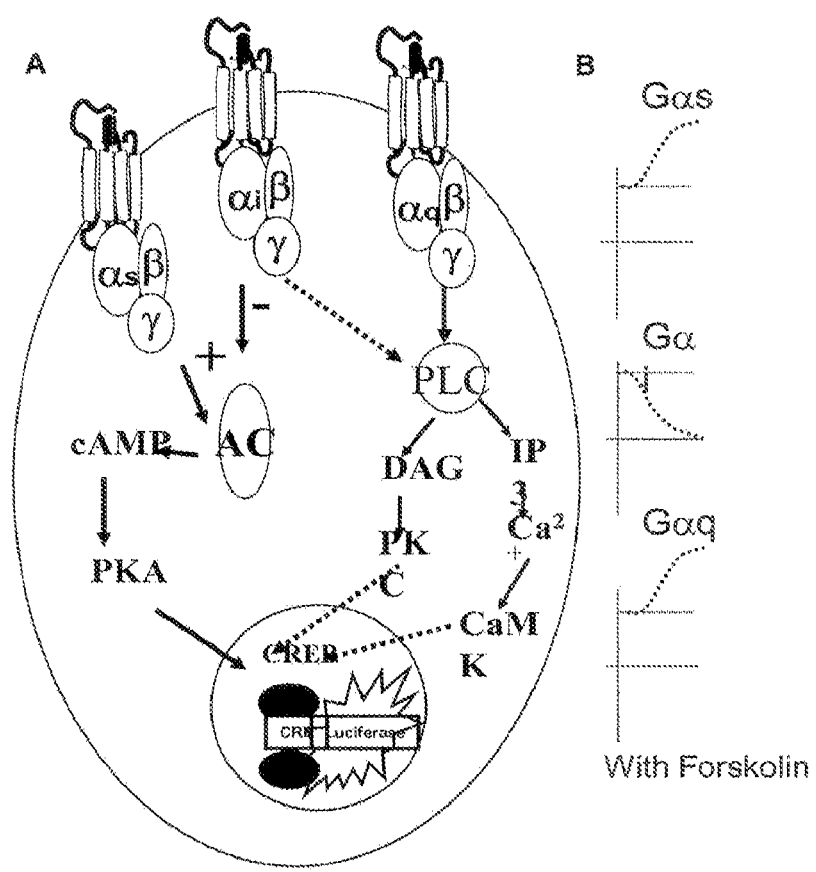
FIG. 1 shows the CreLuc bioimaging mouse model. This figure illustrates the intracellular activation of the CRE Luc reporter transgene by all three types of GPCRs (Gi, Gs, and Gq) either directly through the cAMP pathway or indirectly through the PLC pathway (panel A). The change in the bioluminescence of the luciferase reporter in response to forskolin induction is illustrated for the three types of GPCRs (panel B). Forskolin will increase Gs and Gq signaling and thus CreLuc bioluminescence will increase, while Gi induction will decrease the signal from the reporter. Gαs activates the cAMP dependent pathway by direct stimulation of AC, Gαs inhibits the production of cAMP and Gαq stimulates PLC resulting in the generation of the two second messengers IP3 and DAG. Abbreviations: α,α-subunit of the G protein; β,β-subunit of the G protein; γ,γ-subunit of the G-protein; AC, adenylate cyclase; PLC, phospholipase C; PKA, protein kinase A; PKC, protein kinase C; DAG, diacylglycerol; IP3, inositol triphosphate; $Ca^{+2}$, calcium; CaMK, calcium/calmodulin protein kinase; cAMP, cyclic adenosine monophosphate CRE, cAMP response element; CREB, cAMP responsive element binding protein.
Figure 2A:
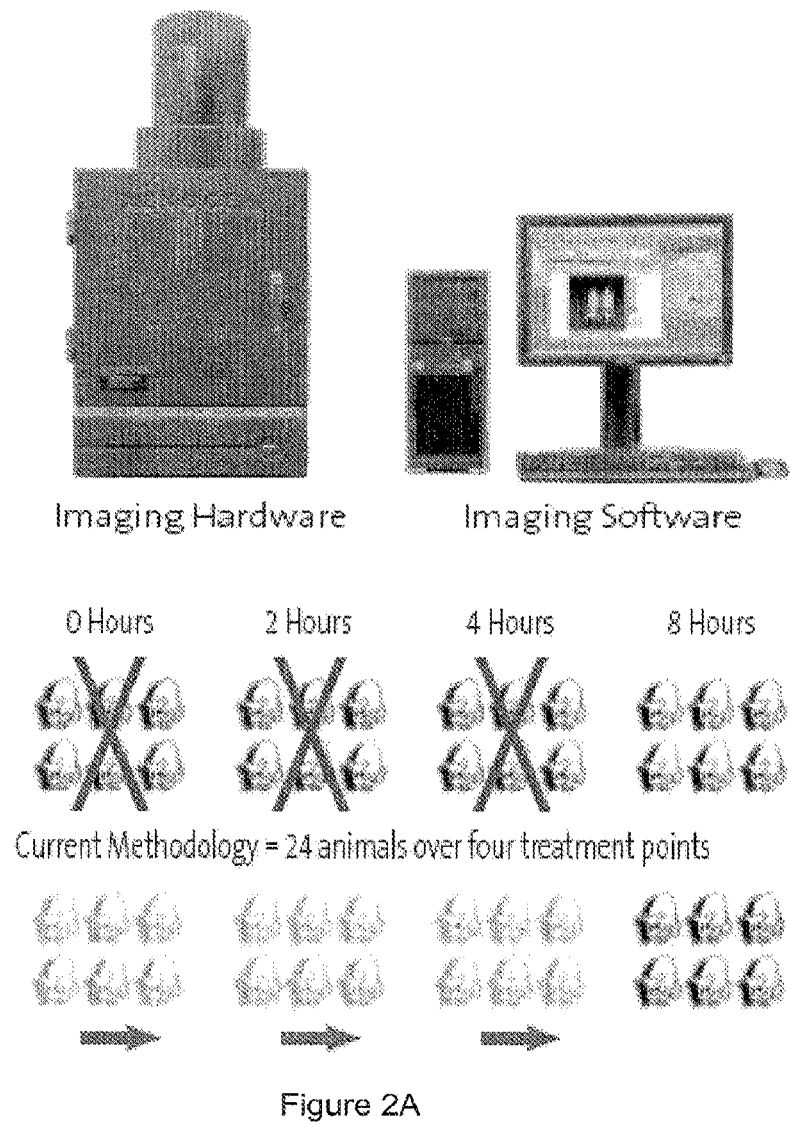
FIG. 2A shows real-time in vivo bioluminescence imaging and describes the benefits of using the system. The IVIS100 (Xenogen) bioimaging instrument with a computer analyzer system allows real-time in vivo imaging utilizing the light emitted by a bioluminescent reporter gene, for instance luciferase, expressed in vivo. The software supports quantification of the signal non-invasively and longitudinally. Real-time in vivo imaging has many advantages over traditional in vivo compound testing. Traditional animal studies require individual mice at multiple treatment points while studies utilizing bioimaging models allow the same animals to be sampled at multiple time points and reused for multiple treatments. As shown in this figure, a time course of 0 hours, 2 hours, 4 hours and 8 hours would require 24 animals (n=6 per time point) using current methodology whereas only 6 animals would be required using bioimaging technology. This results in several benefits which include: higher throughput because fewer test animals are required allowing more compounds to be tested for efficacy; greater data content and quality since temporal and spatial data can be collected from the same animal; and decreases in statistical error which improves the quality of decisions made about individual compounds.
Figure 2B:
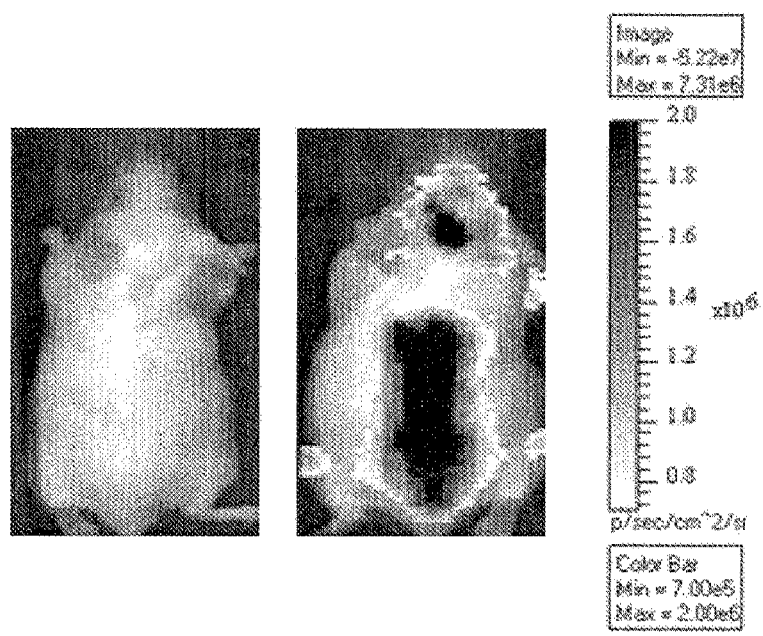
FIG. 2B shows a typical visual image of compound induction in a CreLuc transgenic mouse. Administration of isoproterenol (right panel) increases spinal cord expression of the CRE Luc reporter compared to basal levels (left panel). The bioluminescent detection is represented visually on a white-light image of the animal as a pseudocolor representation in grayscale.

Unless otherwise defined, all technical and scientific terms used herein have the same meaning as commonly understood by one of ordinary skill in the art to which this invention belongs.

Each publication, patent application, patent, and other reference cited herein is incorporated by reference in its entirety to the extent that it is not inconsistent with this present disclosure.

It is noted here that, as used in this specification and the appended claims, the singular forms "a," "an," and "the" include plural reference unless the context clearly dictates otherwise.

Furthermore, in accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

A "test agent" is interpreted broadly to include any material such as a compound or chemical compounds, e.g., organic chemical entities, inorganic chemical entities, biologic compounds or biological materials, e.g., antibodies and antigen recognizing fragments and constructs, nucleic acids, e.g., RNAi, etc. A test agent encompasses a single agent or multiple agents applied together.

As used herein, a "transgenic animal" is a non-human animal, a non-limiting example being a mammal, in that one or more of the cells of the animal includes a genetic modification as defined herein. Further non-limiting examples includes rodents such as a rat or mouse. Other examples of transgenic animals include non-human primates, sheep, dogs, cows, goats, chickens, amphibians etc. The choice of transgenic animal is only limited by the ability of light generated from the reporter to cross tissues and reach the surface where detection can occur.

As used herein, a "genetic modification" is one or more alterations in the non-human animal's gene sequences. A non-limiting example is insertion of a transgene into the genome of the transgenic animal.

As used herein, the term "transgene" refers to exogenous DNA containing a promoter, reporter gene, poly adenlyation signal and other elements to enhance expression (insulators, introns). This exogenous DNA integrates into the genome of a 1-cell embryo from which a transgenic animal develops and the transgene remains in the genome of the mature animal. The integrated transgene DNA can occur at single or multiple places in the genome of the egg or mouse and also single to multiple (several hundred) tandem copies of the transgene can integrate at each genomic location.

The term "general cAMP modulator" refers to chemical compounds, e.g., organic chemical entities, inorganic chemical entities, biologic compounds or biological materials, e.g., antibodies and antigen recognizing fragments and constructs, nucleic acids, e.g., RNAi, etc capable of increasing or maintaining cAMP levels. Non-limiting examples include forskolin and rolipram. A general cAMP modulator encompasses a single cAMP modulator or multiple cAMP modulators applied together.

The term "cell stimulator" refers to chemical compounds, e.g., organic chemical entities, inorganic chemical entities, biologic compounds or biological materials, e.g., antibodies and antigen recognizing fragments and constructs, nucleic acids, e.g., RNAi, etc capable of activating the cell or causing the cell to be in a more activated state. Non-limiting examples include lipopolysaccharide and anti CD3.

An embodiment of the invention uses a control. A control is a term of art well understood by skilled artisans. An appropriate control may be dependent on the assay parameters utilized or the experimental question under investigation. Typically, a control is a vehicle control in which the control is the same buffer or solvent used to dissolve test agent or compounds. A non-limiting example is if phosphate-buffered saline is used to dissolve compound then the vehicle control would be phosphate buffered saline. Similarly, if DMSO is used to dissolve test agents, then the control is DMSO. Often, more than one control must be used per experiment or assay because more than one diluent is used for the compounds tested.

As used herein, "luciferase" refers not only to luciferase enzyme activity but also to actual amounts of luciferase protein.

In accordance with the present invention there may be employed conventional techniques known to those skilled in the art to generate transgenic non-human animals. For instance, Pinkert, C. A. (ed.) 1994. Transgenic animal technology: A laboratory handbook. Academic Press, Inc., San Diedo, Calif.; Monastersky G. M. and Robl, J. M. (ed.) (1995) Strategies in transgenic animal science. ASM Press. Washington D.C. and Nagy A, Gertsenstein, M, Vintersten, K, Behringer R 2003. Manipulating the Mouse Embryo; A laboratory Manual $3^{rd}$ edition. Cold Spring Harbor Laboratory Press, Cold Spring Harbor, N.Y.

Transgene Elements

An embodiment of the invention relates to a transgene. The transgene may comprise insulator elements, response elements, promoter elements, reporter elements, and functional elements.

Response elements are palindromic DNA sequences that respond to cellular signals such as hormones, enzymes, or other key signaling proteins within a cell. Non-limiting examples of response elements include CRE (cAMP response element), estrogen response elements and others listed in Table 2. Response elements may be incorporated into the transgene as a single DNA sequence or in tandem repeats. For instance, CRE response elements repeated four times or six times have been used in transgene construction and validated in vitro (Deutsch P. J., et al., J. Biol. Chem., 263; 18466-18472, 1988; Oetjen E JBC 269; 27036-27044, 1994). Cre response elements have also been compared in vivo and the increase in multimers has correlated with an increase transcriptional response to cAMP pathway activators (Montoliu, L. et al., Proc. Natl. Acad. Sci. USA 92; 4244, 1995; Boer et al, PLoS One, May 9; 2(5):e431, 2007). An embodiment of the invention may utilize any known response element, either as a single sequence or in multiple tandem repeats, for instance, tandem six repeat of CRE (6×CRE).

TABLE 2

Cis acting response elements

| Cis acting enhancer element | Transcription Factor(s) | Signal transduction pathway |
|---|---|---|
| Activator protein 1 (ASP1) | c-jun/c-fos | JNK |
| cAMP response element (CRE) | ATF2/CREB | JNK/p38, PKA |
| Estrogen response element (ERE) | Estrogen receptor | Estrogen receptor |
| Glucocorticoid response element (GRE) | GR | Glucocorticoid/HSP90 |

TABLE 2-continued

Cis acting response elements

| Cis acting enhancer element | Transcription Factor(s) | Signal transduction pathway |
|---|---|---|
| Heat shock response element (HSE) | HSF | Heat shock response |
| Serum response element (SRE) | Lek-1/SRF | MAPK/JNK |
| Thyroid response element (TRE) | Thyroid receptor | Thyroid hormone receptor |

DNA promoter elements are regions of DNA that facilitate the transcription of a particular gene. Promoters are typically located near the genes they regulate, on the same strand and upstream (towards the 5' region of the sense strand). Promoters contain specific DNA sequences and response elements which provide a binding site for RNA polymerase and for proteins called transcription factors that recruit RNA polymerase. DNA promoters are highly variable in their size and internal substructures that contribute to the regulation of a particular gene's expression in time and space. In a non-limiting example of promoter elements, the herpes simplex virus thymidine kinase minimal promoter (HSV TK min) is designed to allow expression of the reporter gene in every cell type. Only its core expression elements are retained to impart ubiquitous expression either in vitro or in vivo (Park, J., et al., DNA Cell Bio., 12:1147-1149, 1994). An embodiment of the invention may utilize any known promoter element. As a non-limiting example, any known promoter element may be used such that the promoter element when combined with the CRE cis-activating response element allows gene expression of the reporter to be responsive to cAMP pathway modulation.

Since the response elements such as CRE and the promoter element HSV TK min are small in size, a transgene promoter containing these elements regulating the transcription of a reporter element will be very sensitive to position effects and lead to poor expression responses to ligands especially at low ligand concentrations in vivo. Thus, an embodiment of the invention is to include to additional elements to be added to the transgene to achieve high levels of expression and wide distribution of a functioning transgene throughout all the cellular compartments. These elements include insulator elements and functional elements (Sun F. L and Elgin S. C, Cell 99:459-462, 1999).

An embodiment of the invention utilizes functional elements or functional enhancer elements within the transgene. A nonlimiting example of a functional element is the human growth hormone (hGH) gene. The hGH sequence used in the CreLuc transgene contains several design elements that contribute and interact with the insulator element to achieve the bioimaging model design goals. The hGH sequence contains all the hGH genomic structure and thus supplies several important elements, but is not transcribed or translated into a protein. The critical influence of the hGH sequence to improve the production of a functioning transgene has been demonstrated since 1990 for several transgenic models Erickson L A, Nature 346: 74-76, 1990. While there is not a comparative analysis of its importance, the hGH structure does contain several important and critical DNA elements:

a. Intron splicing: Initially transcribed mRNA contains both intronic and exon sequences which then are exported from the nucleus and further processed to remove intronic sequence resulting in a mature mRNA containing only exon sequences. This transport and trimming process connect the maturing mRNA strand to additional translational machinery for the final production of a protein. Including introns in transgene cDNA structure has been shown to improve the expression level of the transgene cDNA (Palmiter, R. D., et al., Proc. Natl. Acad. Sci. USA 88:478-482, 1988)

b. Genomic structure with intact 3'UTR: In an embodiment of the invention, the hGH sequence in the transgene contains an intact 3'UTR which imparts a high degree of mRNA stability and thus higher levels of transgene expression c. Genomic structure with poly A (PA+) structures The hGH sequence contains its native PA+ structure imbedded in the nature 3' UTR. Typically PA+ signals are from viral sequences (SV40, RSV etc.) and are minimal structures added to the end of unrelated 3'UTRs. In an embodiment of the invention, the entire 3'UTR structure with the nature PA+ signal is preserved in the even wider genomic context of the full hGH gene.

Insulator elements are sequences of DNA that generate position independent expression (Giraldo et al, Transgenic Research 12: 751-755, 2003). Insulator sequences were described in the 1980s for the globulin locus (Sun F. L. and Elgin, S. C., Cell 99; 459-462, 1999) and were reported to increase the chance of obtaining correct and responsive transgenic expression in selected tissues to support the model design goals for bioimaging. (Pinkert, C. A. (ed.) 1994. Transgenic animal technology: A laboratory handbook. Academic Press, Inc., San Diego, Calif.; Monastersky G. M. and Robl, J. M. (ed.) (1995) Strategies in transgenic animal science. ASM Press. Washington D.C) Insulators are DNA elements that create open chromatin domains permissive to gene expression and constitute a barrier against the influence of distal silencer/enhancer sequences and against acetylation and methylation events. They should significantly increase the number of independent transgenic founder lines that have the reporter gene expressed at detectable levels for bioimaging. Insulator elements have been shown to increase the number of luciferase expressing clones in a transient transfection assay from 40 to 70% thus enhancing the inducibility of luciferase expression in an ERE-luci transgene. (Ottobrini L., Mol Cell Endo 246, 69-75). However a full review of the application of insulators to transgene reporter expression leads to the conclusion that in practical terms, it remains difficult to utilize insulators. Their mechanism of action is only partly known and their effect is not fully predictable. Non-limiting examples of insulator elements are included in Table 3.

TABLE 3

Examples of known insulator elements to improve transgene DNA expression

| Insulator | Gene or origin | References |
|---|---|---|
| DNase I-hypersensitive site (HS4) | Human beta-globin | Chung et al 1993 |
| Matrix attachment regions (MAR) | Chicken lysozyme | Stief et al 1989 |
| Inverted terminal repeats (ITR) | Adeno-associated virus | Fu et al, 1998 |

In an embodiment of the Cre-Luc transgene, the inclusion of insulator elements significantly increased the frequency of generating lines with a functional reporter as detected by bioimaging. For an analysis of the contribution of insulator elements to luciferase expression in our CreLuc transgenic mouse lines, see section VI of "Examples" below.

An embodiment of the invention relates to a transgene comprising a reporter element or gene. A reporter gene includes any gene that expresses a detectable gene product, which may be an RNA or a protein. Many reporter genes are known in the art, including, but not limited to beta-galactosidase and alkaline phosphatase. In another embodiment, the transgene comprises a bioluminescent reporter gene. Many bioluminescent reporter genes are known in the art, including, but not limited to luciferase. There are many sources of luciferase, nonlimiting examples include firefly luciferase and bacterial luciferase. An embodiment of the invention may utilize any known bioluminescent reporter, for instance, luciferase. Other non-limiting examples of reporter elements are shown in Table 5.

TABLE 4

Genetic reporter systems

| Reporter Gene | In vitro assay | In vivo assay |
|---|---|---|
| Chloramphenicol acetyltransferase (CAT) | Chromatography, differential extraction, fluorescence or immunoassay | RNA or enzyme assay of tissue extracts |
| Luciferase - firefly | Bioluminescence with luminometer or scintillation counter | Assay in live cells with luciferin esters as substrate |
| Luciferase - renilla | Bioluminescence with luminometer or scintillation counter | Assay in live cells with luciferin esters as substrate |
| Beta-galactosidase | Colorimetric, fluorescence, chemiluinescence | Histochemical staining with X-gal substrate: bioluminescence assay in live cells with fluorescein di-beta-D-galactopyransodie (FDG) |
| Secreted alkaline phosphatase (SEAP) | Colorimetric bioluminescence, or chemiluminescence | RNA or enzyme assay from tissue extracts |
| Human growth hormone (hGH) | Radioimmunoassay | RNA or protein assay from tissue extracts |
| Green fluorescent protein (GFP) | Fluorescence (UV light box or fluorescence imaging device) | Fluorescence (UV light box, fluorescence microscopy or FACS |

Other embodiments of the invention can incorporate modified versions of the luciferase enzyme, luciferase enzyme from different species or any other protein that can produce light able to cross animal tissues or any enzyme that can emit light able to cross animal tissues when provided with a suitable substrate. The reporter protein of the present invention is only limited by the fact that signal attenuation depends on the wavelength of the light being emitted and the tissue properties surrounding the emitting cells. Generally, blue-green light (400 590 nm) is strongly attenuated while red to near-infrared light (590 800 nm) suffers much less attenuation. Most types of luciferase have peak emission at blue to yellow-green wavelengths, the emission spectrum is broad such that there is significant emission at red wavelengths (>600 nm) that penetrate quite deeply into tissue. For small rodents such as mice, this allows detection of signals throughout the entire animal.

The limits of light detection in vivo depend on the type of bioluminescent reporter, the surrounding physiology of the animal and on the source depth. Typically, bioluminescent cells in animals can be observed from 1 3 cm deep with sensitive CCD cameras, depending on the number and location of the cells. Scattering of photons as they propagate through tissue limits the spatial resolution of images detected on the animal surface. In general, spot size or resolution on the surface is approximately equal to the depth of the source below the surface. Using physics based diffusion models, improvements in spatial resolution approaching the millimeter level can be achieved. Using cooled scientific grade CCD arrays, the limit in signal detection is determined by the read noise associated with reading CCD pixels after an image is taken, which is on the order of a few photons per pixel (Honigman et al., Mol. Ther. 4:239-249, 2001). There may be additional background light coming from the animal due to phosphorescence of the fur, skin, or perhaps contaminants on the animal. Typically, background light is at a low level and only has a deleterious effect on images of deep low-level bioluminescent sources. However, background light can be eliminated by using use of an appropriate optical filter.

An embodiment of the invention utilizes CCD cameras such as the IVIS (Xenogen Corporation, 860 Atlantic Avenue, Alameda, Calif. 94501, USA). The IVIS™ Imaging System includes a sensitive CCD camera, a dark imaging chamber to minimize incident light, and specialized software to quantify and analyze the results. IVIS is a registered trademark of Xenogen Corporation. However, any such bioluminescence imaging system can be applied to the instant invention.

Real-time in vivo imaging allows the quantification of the bioluminescent reporter gene non-invasively, i.e., the animal does not need to be euthanized, and longitudinally, i.e., the measurements can continuous or repeated over a prolonged time course. Real-time in vivo imaging requires fewer test animals (e.g., because the same animal can be used over a specified time period) and less time (e.g., because fewer animals need to be handled) than conventional protocols allowing more test compounds to be tested for efficacy. real-time in vivo imaging provides for a higher data content and higher data quality for many reasons. For instance, temporal and spatial data can be collected from the same animal and data can be collected without need for time-consuming histological assessment. Higher data quality decreases statistical error and improves the quality of test compound assessment and decision making.

An embodiment of the invention is use in high throughput screening (HTS) methods. HTS is the automated, simultaneous testing of thousands of distinct chemical compounds in assays designed to model biological mechanisms or aspects of disease pathologies. More than one compound, e.g., a plurality of compounds, can be tested simultaneously, e.g., in one batch. In one embodiment, the term HTS screening method refers to assays which test the ability of one compound or a plurality of compounds to influence the readout of choice.

Liquid handling systems, analytical equipment such as fluorescence readers or scintillation counters and robotics for cell culture and sample manipulation are well known in the art. Mechanical systems such as robotic arms or "cherry-picking" devices are available to the skilled artisan. Commercial plate readers are available to analyze conventional 96-well or 384-well plates. Single sample, multiple sample or plate sample readers are available that analyze predetermined wells and generate raw data reports. The raw data can be transformed and presented in a variety of ways.

An embodiment of the invention comprises an array of receptacles that can receive cells, tissue slices and other materials such as culture media. An array of receptacles can be any number of receptacles from at least one or more than one receptacle suitable for holding cells or tissue slices within the scope of the invention. Examples include but are not limited to flasks, culture dishes, tubes such as 1.5 ml tubes, 12 well plates, 96 well plates, 384 well plates and miniaturized microtiter plates with perhaps 4000 receptacles (U.S. Patent Application 20050255580). The array of receptacles may be amendable to the addition of a protective covering thus preventing against entry of contaminants or evaporation of contents.

A further characteristic of the receptacles is that the receptacle may allow for analysis, non-limiting examples include, spectrophotometric analysis, scintillation counting and fluorescence measurements. However, this is not a limitation to receptacles that can be used within the scope of the invention given that samples can be transferred to a suitable container amendable for further analysis. A non limiting example is to modify the method such that the method further comprises providing a second array of receptacles wherein the step of lysing the cells further comprises separating supernatant from cell debris and the next step further comprises adding a detectable compound capable of intercalating into DNA fragments to at least one receptacle of said second array of receptacles containing a sample of said separated supernatant.

Additional aspects and details of the invention will be apparent from the following examples, which are intended to be illustrative and are not meant to limit the scope of the invention in any way.

All experimental work involving animals was performed in accordance with federal guidelines and protocols were prior reviewed and approved by the sanofi-aventis site Institutional Animal Care and Use Committee (IACUC).

EXAMPLES

Figure 3:
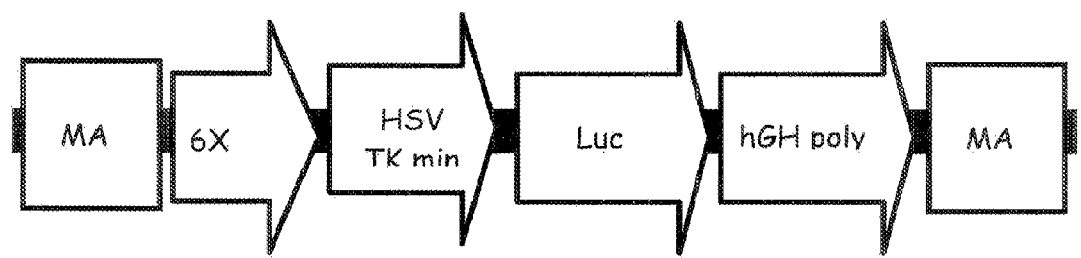
FIG. 3 shows a schematic representation of a transgene structure comprising multiple DNA elements to enhance expression. The schematic transgene structure comprises the following elements: an insulator element shown in this figure as matrix attachment regions (MAR) to generate position independent expression; a response element represented by CRE-cAMP repeated six times (6×CRE); a promoter element shown as a herpes simplex virus thymidine kinase minimal promoter (HSV TK min); a reporter element which is represented by a luciferase gene optimized for mammalian expression (LUC2); and a functional element depicted by human growth hormone gene with poly A tail (hGH poly A) to enhance transgene expression.
Figure 4:
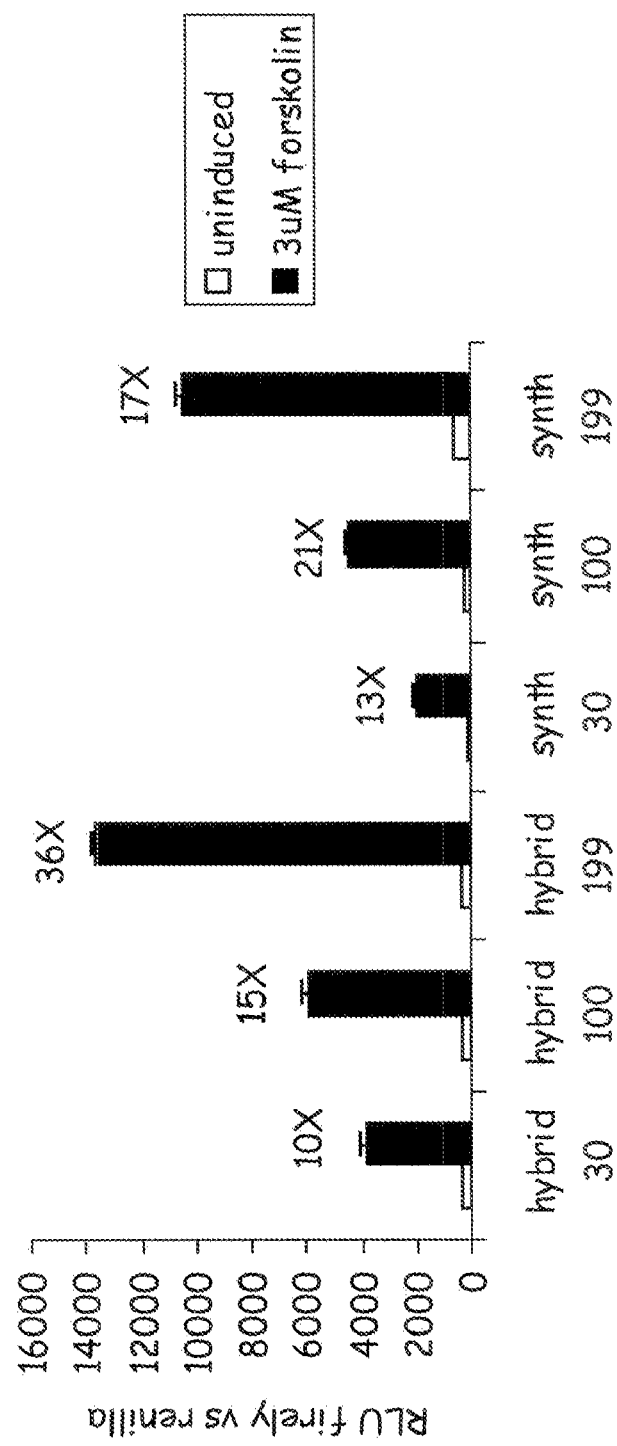
FIG. 4: In vitro validation of CreLuc transgene vectors. Hybrid or synthetic (synth) vectors at 30, 100 or 199 ng DNA were transfected into CHO cells (along with a renilla luciferase positive control vector) with Lipofectamine 2000 (Invitrogen, Carlsbad, Calif., cat #11668-019). Two days later, the cells were stimulated with 3 μM forskolin (Sigma, St Louis, Mo., cat #F6886) for 4 hours and then luciferase activity was measured with Dual Glo Luciferase Assay System (Promega, Madison, Wis., cat#E2920). Results show a dose dependant increase in the luciferase signal with both vectors. Higher levels of induction were achieved with the hybrid vector.

I. Vector Backbone for the MultiSite Gateway Pro Plus Cloning System (FIG. 3)

A destination vector, pDest2XMARS was designed and cloned specifically for use with the MultiSite Gateway Pro Plus Cloning System (Invitrogen Carlsbad, Calif., cat #12537-100). All elements inserted into the vector were either PCR (polymerase chain reaction) cloned or synthetically generated. For all PCR cloning steps, the fragments were amplified from the specified vector through the use of PCR SuperMIx Hi Fidelity (Invitrogen, Carlsbad, Calif., cat #10790-020) and fragment specific primers. The PCR products were then subcloned into pCR2.1 vectors by TOPO cloning. TOPO Cloning is a molecular biology technique in which DNA fragments amplified by either Taq or Pfu polymerases are cloned into specific vectors without the requirement for DNA ligases.

First, insulator elements were cloned by polymerases chain reaction (PCR) from the vector pCpG-LacZ (InvivoGen San Diego, Calif., cat # pcpg-lacz), sequence verified and then subcloned into restriction sites of pNEB193 (New England Biolabs Ipswich, Mass., cat#N3051S). The insulator elements were used to reduce variability in expression of the transgene due to integration site dependant position effects.

The PCR primers used to clone the fragments are the following:
a. Human IFN-β MAR primer sequences (primers have EcoRV sites for subcloning)

```
                                           SEQ ID NO: 1
IFN forward primer:
5'-GGGGGATATCAGTCAATATGTTCACCCCA-3', SEQ ID NO: 2
IFN reverse primer:
5'-GGGGGATATCCTACTGTTTTAATTAAGC-3',
``` b. Human β-globin MAR primer sequences

```
                                           SEQ ID NO: 3
β-globin forward primer:
5'-AAGGATCCTTAATTAAAATTATCTCTAAGGC-3', SEQ ID NO: 4
β-globin reverse primer:
5'-GGATCCCTGCAGGAATTCCTTTTAAT-3',
```

The β-globin PCR fragment was topo cloned using pCR2.1 (Invitrogen, Carlsbad, Calif., cat#K2030-01). After sequence confirmation, the fragment was cut out with BamHI and then subcloned into the BamH1 site of pNEB193 (βgloMAR-pNEB193). The IFN-β PCR fragment was also topo cloned with pCR2.1, sequenced, and then cut out with EcoRv and subcloned into the HincII site of βgloMAR-pNEB193 (2XMARS-pNEB193).

For the final Gateway destination vector, a linker containing XbaI ends and an internal EcoRV site was subcloned into XbaI site of 2XMARs-pNEB193. The blunt ended Gateway conversion cassette, RfA was then inserted into the EcoRV site of 2XMARs-pNEB193 (2XMARSpDest). The final vector, 2XMARSpDest was the final destination vector used to generate the transgenes.

```
                                           SEQ ID NO: 5
TCGCGCGTTTCGGTGATGACGGTGAAAACCTCTGACACATGCAGCTCCCG
GAGACGGTCACAGCTTGTCTGTAAGCGGATGCCGGGAGCAGACAAGCCCG
TCAGGGCGCGTCAGCGGGTGTTGGCGGGTGTCGGGGCTGGCTTAACTATG
CGGCATCAGAGCAGATTGTACTGAGAGTGCACCATATGCGGTGTGAAATA
CCGCACAGATGCGTAAGGAGAAAATACCGCATCAGGCGCCATTCGCCATT
CAGGCTGCGCAACTGTTGGGAAGGGCGATCGGTGCGGGCCTCTTCGCTAT
TACGCCAGCTGGCGAAAGGGGGATGTGCTGCAAGGCGATTAAGTTGGGTA
ACGCCAGGGTTTTCCCAGTCACGACGTTGTAAAACGACGGCCAGTGAATT
CGAGCTCGGTACCCGGGGCGCGCCGGGATCCTTAATTAAAATTATCTCT
AAGGCATGTGAACTGGCTGTCTTGGTTTTCATCTGTACTTCATCTGCTAC
CTCTGTGACCTGAAACATATTTATAATTCCATTAAGCTGTGCATATGATA
GATTTATCATATGTATTTTCCTTAAAGGATTTTTGTAAGAACTAATTGAA
TTGATACCTGTAAAGTCTTTATCACACTACCCAATAAATAATAAATCTCT
TTGTTCAGCTCTCTGTTTCTATAAATATGTACCAGTTTTATTGTTTTTAG
TGGTAGTGATTTTATTCTCTTTCTATATATATACACACACATGTGTGCAT
TCATAAATATATACAATTTTTATGAATAAAAAATTATTAGCAATCAATAT
TGAAAACCACTGATTTTTGTTTATGTGAGCAAACAGCAGATTAAAAGGAA
TTCCTGCAGGATCCTTAATTAAGTTCTAGATCACAAGTTTGTACAAAAAA
GCTGAACGAGAAACGTAAAATGATATAAATATCAATATATTAAATTAGAT
TTTGCATAAAAAACAGACTACATAATACTGTAAAACACAACATATCCAGT
CACTATGGCGGCCGCATTAGGCACCCCAGGCTTTACACTTTATGCTTCCG
GCTCGTATAATGTGTGGATTTTGAGTTAGGATCCGTCGAGATTTTCAGGA
GCTAAGGAAGCTAAAATGGAGAAAAAAATCACTGGATATACCACCGTTGA
TATATCCCAATGGCATCGTAAAGAACATTTTGAGGCATTTCAGTCAGTTG
```

-continued

```
CTCAATGTACCTATAACCAGACCGTTCAGCTGGATATTACGGCCTTTTTA
AAGACCGTAAAGAAAAATAAGCACAAGTTTTATCCGGCCTTTATTCACAT
TCTTGCCCGCCTGATGAATGCTCATCCGGAATTCCGTATGGCAATGAAAG
ACGGTGAGCTGGTGATATGGGATAGTGTTCACCCTTGTTACACCGTTTTC
CATGAGCAAACTGAAACGTTTTCATCGCTCTGGAGTGAATACCACGACGA
TTTCCGGCAGTTTCTACACATATATTCGCAAGATGTGGCGTGTTACGGTG
AAAACCTGGCCTATTTCCCTAAAGGGTTTATTGAGAATATGTTTTTCGTC
TCAGCCAATCCCTGGGTGAGTTTCACCAGTTTTGATTTAAACGTGGCCAA
TATGGACAACTTCTTCGCCCCCGTTTTCACCATGGGCAAATATTATACGC
AAGGCGACAAGGTGCTGATGCCGCTGGCGATTCAGGTTCATCATGCCGTT
TGTGATGGCTTCCATGTCGGCAGAATGCTTAATGAATTACAACAGTACTG
CGATGAGTGGCAGGGCGGGGCGTAAACGCGTGGATCCGGCTTACTAAAAG
CCAGATAACAGTATGCGTATTTGCGCGCTGATTTTTGCGGTATAAGAATA
TATACTGATATGTATACCCGAAGTATGTCAAAAAGAGGTATGCTATGAAG
CAGCGTATTACAGTGACAGTTGACAGCGACAGCTATCAGTTGCTCAAGGC
ATATATGATGTCAATATCTCCGGTCTGGTAAGCACAACCATGCAGAATGA
AGCCCGTCGTCTGCGTGCCGAACGCTGGAAAGCGGAAAATCAGGAAGGGA
TGGCTGAGGTCGCCCGGTTTATTGAAATGAACGGCTCTTTTGCTGACGAG
AACAGGGGCTGGTGAAATGCAGTTTAAGGTTTACACCTATAAAGAGAGA
GCCGTTATCGTCTGTTTGTGGATGTACAGAGTGATATTATTGACACGCCC
GGGCGACGGATGGTGATCCCCCTGGCCAGTGCACGTCTGCTGTCAGATAA
AGTCTCCCGTGAACTTTACCCGGTGGTGCATATCGGGGATGAAAGCTGGC
GCATGATGACCACCGATATGGCCAGTGTGCCGGTCTCCGTTATCGGGGAA
GAAGTGGCTGATCTCAGCCACCGCGAAAATGACATCAAAAACGCCATTAA
CCTGATGTTCTGGGGAATATAAATGTCAGGCTCCCTTATACACAGCCAGT
CTGCAGGTCGACCATAGTGACTGGATATGTTGTGTTTTACAGTATTATGT
AGTCTGTTTTTTATGCAAAATCTAATTTAATATATTGATATTTATATCAT
TTTACGTTTCTCGTTCAGCTTTCTTGTACAAAGTGGTGATCTAGACTAGA
GTCATCAGTCAATATGTTCACCCCAAAAAAGCTGTTTGTTAACTTGTCAA
CCTCATTCTAAAATGTATATAGAAGCCCAAAAGACAATAACAAAAATATT
CTTGTAGAACAAAATGGGAAAGAATGTTCCACTAAATATCAAGATTTAGA
GCAAAGCATGAGATGTGTGGGGATAGACAGTGAGGCTGATAAAATAGAGT
AGAGCTCAGAAACAGACCCATTGATATATGTAAGTGACCTATGAAAAAAA
TATGGCATTTTACAATGGGAAAATGATGATCTTTTTCTTTTTTAGAAAAA
CAGGGAAATATATTTATATGTAAAAAATAAAAGGGAACCCATATGTCATA
CCATACACACAAAAAAATTCCAGTGAATTATAAGTCTAAATGGAGAAGGC
AAAACTTTAAATCTTTTAGAAAATAATATAGAAGCATGCCATCAAGACTT
CAGTGTAGAGAAAAATTTCTTATGACTCAAAGTCCTAACCACAAAGAAAA
GATTGTTAATTAGATTGCATGAATATTAAGACTTATTTTTAAAATTAAA
AACCATTAAGAAAAGTCAGGCCATAGAATGACAGAAAATATTTGCAACAC
CCCAGTAAAGAGAATTGTAATATGCAGATTATAAAAAGAAGTCTTACAAA
```

-continued

```
TCAGTAAAAAATAAAACTAGACAAAAATTTGAACAGATGAAAGAGAAACT
CTAAATAATCATTACACATGAGAAACTCAATCTCAGAAATCAGAGAACTA
TCATTGCATATACACTAAATTAGAGAAATATTAAAAGGCTAAGTAACATC
TGTGGCTTAATTAAAACAGTAGGATGACTGTTTAAACCTGCAGGCATGCA
AGCTTGGCGTAATCATGGTCATAGCTGTTTCCTGTGTGAAATTGTTATCC
GCTCACAATTCCACACAACATACGAGCCGGAAGCATAAAGTGTAAAGCCT
GGGGTGCCTAATGAGTGAGCTAACTCACATTAATTGCGTTGCGCTCACTG
CCCGCTTTCCAGTCGGGAAACCTGTCGTGCCAGCTGCATTAATGAATCGG
CCAACGCGCGGGGAGAGGCGGTTTGCGTATTGGGCGCTCTTCCGCTTCCT
CGCTCACTGACTCGCTGCGCTCGGTCGTTCGGCTGCGGCGAGCGGTATCA
GCTCACTCAAAGGCGGTAATACGGTTATCCACAGAATCAGGGGATAACGC
AGGAAAGAACATGTGAGCAAAAGGCCAGCAAAAGGCCAGGAACCGTAAAA
AGGCCGCGTTGCTGGCGTTTTTCCATAGGCTCCGCCCCCCTGACGAGCAT
CACAAAAATCGACGCTCAAGTCAGAGGTGGCGAAACCCGACAGGACTATA
AAGATACCAGGCGTTTCCCCCTGGAAGCTCCCTCGTGCGCTCTCCTGTTC
CGACCCTGCCGCTTACCGGATACCTGTCCGCCTTTCTCCCTTCGGGAAGC
GTGGCGCTTTCTCATAGCTCACGCTGTAGGTATCTCAGTTCGGTGTAGGT
CGTTCGCTCCAAGCTGGGCTGTGTGCACGAACCCCCCGTTCAGCCCGACC
GCTGCGCCTTATCCGGTAACTATCGTCTTGAGTCCAACCCGGTAAGACAC
GACTTATCGCCACTGGCAGCAGCCACTGGTAACAGGATTAGCAGAGCGAG
GTATGTAGGCGGTGCTACAGAGTTCTTGAAGTGGTGGCCTAACTACGGCT
ACACTAGAAGAACAGTATTTGGTATCTGCGCTCTGCTGAAGCCAGTTACC
TTCGGAAAAAGAGTTGGTAGCTCTTGATCCGGCAAACAAACCACCGCTGG
TAGCGGTGGTTTTTTTGTTTGCAAGCAGCAGATTACGCGCAGAAAAAAAG
GATCTCAAGAAGATCCTTTGATCTTTTCTACGGGGTCTGACGCTCAGTGG
AACGAAAACTCACGTTAAGGGATTTTGGTCATGAGATTATCAAAAAGGAT
CTTCACCTAGATCCTTTTAAATTAAAAATGAAGTTTTAAATCAATCTAAA
GTATATATGAGTAAACTTGGTCTGACAGTTACCAATGCTTAATCAGTGAG
GCACCTATCTCAGCGATCTGTCTATTTCGTTCATCCATAGTTGCCTGACT
CCCCGTCGTGTAGATAACTACGATACGGGAGGGCTTACCATCTGGCCCCA
GTGCTGCAATGATACCGCGAGACCCACGCTCACCGGCTCCAGATTTATCA
GCAATAAACCAGCCAGCCGGAAGGGCCGAGCGCAGAAGTGGTCCTGCAAC
TTTATCCGCCTCCATCCAGTCTATTAATTGTTGCCGGGAAGCTAGAGTAA
GTAGTTCGCCAGTTAATAGTTTGCGCAACGTTGTTGCCATTGCTACAGGC
ATCGTGGTGTCACGCTCGTCGTTTGGTATGGCTTCATTCAGCTCCGGTTC
CCAACGATCAAGGCGAGTTACATGATCCCCCATGTTGTGCAAAAAAGCGG
TTAGCTCCTTCGGTCCTCCGATCGTTGTCAGAAGTAAGTTGGCCGCAGTG
TTATCACTCATGGTTATGGCAGCACTGCATAATTCTCTTACTGTCATGCC
ATCCGTAAGATGCTTTTCTGTGACTGGTGAGTACTCAACCAAGTCATTCT
GAGAATAGTGTATGCGGCGACCGAGTTGCTCTTGCCCGGCGTCAATACGG
```

-continued
GATAATACCGCGCCACATAGCAGAACTTTAAAAGTGCTCATCATTGGAAA

ACGTTCTTCGGGGCGAAAACTCTCAAGGATCTTACCGCTGTTGAGATCCA

GTTCGATGTAACCCACTCGTGCACCCAACTGATCTTCAGCATCTTTTACT

TTCACCAGCGTTTCTGGGTGAGCAAAAACAGGAAGGCAAAATGCCGCAAA

AAAGGGAATAAGGGCGACACGGAAATGTTGAATACTCATACTCTTCCTTT

TTCAATATTATTGAAGCATTTATCAGGGTTATTGTCTCATGAGCGGATAC

ATATTTGAATGTATTTAGAAAAATAAACAAATAGGGGTTCCGCGCACATT

TCCCCGAAAAGTGCCACCTGACGTCTAAGAAACCATTATTATCATGACAT

TAACCTATAAAAATAGGCGTATCACGAGGCCCTTTCGTC

II. Transgene Components

A. CREs:

Two different 6XCRE elements were used in the generation of the transgenes. The first is a synthetic CRE element (noted as "synthetic") which was synthetically generated at DNA2.0, Menlo Park, Calif. The synthetic sequence has attL1 and attR5 sites for 4-fragment Gateway cloning.

Multiple attempts were made to PCR clone out the 6×CRE from different vectors; however this was not possible due to a hairpin structure in the middle of the CREs. This fragment was then cloned synthetically. The second 6×CRE element used is a hybrid version generated by PCR cloning the CRE elements from a Clontech vector (Mountainview, Calif., cat#PT3336-5). Clontech claims that there are 2× CREs in the vector but sequence analysis indicated that there were actually three present. Two different PCR reactions were used to clone the fragment. Att sites for Gateway cloning as well as an EcoR1 site were introduced in the primers to enable the two fragments to be "glued" together and then recombined into the Invitrogen Gateway pDONR P1-P5r vector (Carlsbad, Calif., cat #12537-100).

1. Synthetic CRE element

SEQ ID NO: 6:
5'AAATAATGATTTTATTTTGACTGATAGTGACCTGTTCGTTGCAACAAA

TTGATGAGCAATGCTTTTTTATAATGCCAACTTTGTACAAAAAAGCAGGC

TTACTGTCGACAATTGCGTCATACTGTGACGTCTTTCAGACACCCCATTG

ACGTCAATGGGATTGACGTCAATGGGGTGTCTGAAAGACGTCACAGTATG

ACCCGGGCTCGAGCCTCCTTGGCTGACGTCAGAGAGAGAGGCCGGCCCCT

TACGTCAGAGGCGAGAATTCGACAACTTTGTATACAAAAGTTGAACGAGA

AACGTAAAATGATATAAATATCAATATATTAAATTAGATTTTGCATAAAA

AACAGACTACATAATACTGTAAAACACAACATATCCAGTCACTATG3'

2. Hybrid CRE: Standard cloning, PCR amplified the CRE element from the Clontech pCreLuc vector which contains 3XCREs, PCR primers have an EcoR1 restriction site at one end (CRE3X-B, CRE3X-C), and an att site, either attB1 or attB5r for Gateway cloning at the other end (CRE3X-A, CRE3X-D). The two fragments were then combined to create one fragment with 6XCREs. The fragment gets recombined into the Gateway pDONR P1-P5r vector.

SEQ ID NO: 7: CRE forward primer A
5'-GGGGACAAGTTTGTACAAAAAAGCAGGCTTAGCACCAGACAGTGA-3'

SEQ ID NO: 8: CRE reverse primer B
5'-GGGAATTCGTTCTCCCATTGACGTCA-3'

SEQ ID NO: 9: CRE forward primer C
5'-GGGAATTCGCACCAGACAGTGACGTC-3'

SEQ ID NO: 10: CRE reverse primer D
5'-GGGGACAACTTTTGTATACAAAGTTGTGTTCTCCCATTGACGTCA-3'

SEQ ID NO: 11: Hybrid CRE sequence:
GCTTAGCACCAGACAGTGACGTCAGCTGCCAGATCCCATGGCCGTCATA

CTGTGACGTCTTTCAGACACCCCATTGACGTCAATGGGAGAACGAATTCG

CACCAGACAGTGACGTCAGCTGCCAGATCCCATGGCCGTCATACTGTGA

CGTCTTTCAGACACCCCATTGACGTCAATGGGAGAACA

B. Human Growth Hormone Poly A Tail:

Human growth hormone poly A tail was PCR cloned from the vector pOGH (Nichols Institute Diagnostics (San Juan Capistrano, Calif., Cat #40-2205). Primer sequences have an attB3 site on the forward primer and an attB2 site on the reverse primer for recombination into the Gateway pDONR P3-P2 vector.

SEQ ID NO: 12: hGH forward primer:
5'-GGGGACAACTTTGTATAATAAAGTTGGATCCCAAGGCCCAACTCC-3'

SEQ ID NO: 13: hGH reverse primer
5'-GGGGACCACTTTGTACAAGAAAGCTGGGTACAACAGGCATCTACT-3'

C. HSV TK Minimal Promoter:

HSV TK Minimal Promoter was PCR cloned from an in house vector called "661 CreLuc". Primer sequences have an attB5 site on the forward primer and an attB4 site on the reverse primer for recombination into the Gateway pDONR P5-P4 vector.

SEQ ID NO: 14: TK forward primer
5'-GGGGACAACTTTGTATACAAAAGTTGTGGAACACGCAGATGCAGT-3'

SEQ ID NO: 15: TK reverse primer
5'-GGGGACAACTTTGTATAGAAAAGTTGGGTGGATCTGCGGCACGCT-3'

D. Luciferase cDNA:

Luciferase cDNA was PCR cloned from the vector pGL4.10 (Promega Madison, Wis. Cat #E6651). Luc primer sequences have an attB4r site on the forward primer and an attB3r site on the reverse primer for recombination into the Gateway pDONR P4r-P3r vector.

SEQ ID NO: 16: luci forward primer
5'GGGGACAACTTTTCTATACAAAGTTGATGGAAGATGCCAAAAACA3'

SEQ ID NO: 17: luci reverse primer
5'GGGGACAACTTTATTATACAAAGTTGTTTACACGGCGATCTTGCC3'

III. Final Vector Construction

The four components of the transgene, CRE (either synthetic or hybrid version), HSVTK min, luciferase cDNA, and the hGH poly A tail in the pDONR vectors were recombined with the pDest2XMARs destination vector according to the standard Invitrogen protocol. The two transgenes were then sequenced, and transfected into CHOK1 to test for function. Both transgenes are functional in vitro as shown in FIG. 5. FIG. 5 shows the in vitro analysis of CreLuc vectors by forskolin induction.

IV. Transgenic Mouse Generation

A. Transgene Preparation:

The quality of the transgene constructs were verified and confirmed by running aliquots on an agarose gel. No trace of degradation was observed. Finally, restriction analysis using diagnostic XhoI and PvuII and PstI restriction enzymes yielded the expected restriction profiles. The transgene plasmids were then digested by Acc65I and PmeI and the fragments containing the transgenes, were isolated from the vector backbones by running the digests on an agarose gel. The transgene fragments were then cut out of the gel, purified with a Qiaquick gel extraction kit (Qiagen, Valencia, Calif. cat#28706) and diluted before injection into fertilized oocytes. The purity and concentration of the isolated transgene were verified by agarose gel electrophoresis

```
SEQ ID NO: 18: CreLuc synthetic transgene
(Acc65I/PmeI digest, 5550 bp)
5'GTACCCGGGGGCGCGCCGGGATCCTTAATTAAAATTATCTCTAAGGCA

TGTGAACTGGCTGTCTTGGTTTTCATCTGTACTTCATCTGCTACCTCTGT

GACCTGAAACATATTTATAATTCCATTAAGCTGTGCATATGATAGATTTA

TCATATGTATTTTCCTTAAAGGATTTTTGTAAGAACTAATTGAATTGATA

CCTGTAAAGTCTTTATCACACTACCCAATAAATAATAAATCTCTTTGTTC

AGCTCTCTGTTTCTATAAATATGTACCAGTTTTATTGTTTTTAGTGGTAG

TGATTTTATTCTCTTTCTATATATATACACACATGTGTGCATTCATAA

ATATATACAATTTTTATGAATAAAAAATTATTAGCAATCAATATTGAAAA

CCACTGATTTTTGTTTATGTGAGCAAACAGCAGATTAAAAGGAATTCCTG

CAGGATCCTTAATTAAGTTCTAGATCCAAGTTTGTACAAAAAAGCAGGCT

TACTGTCGACAATTGCGTCATACTGTGACGTCTTTCAGACACCCCATTGA

CGTCAATGGATTGACGTCAATGGGGTGTCTGAAAGACGTCACAGTATGA

CCCGGGCTCGAGCCTCCTTGGCTGACGTCAGAGAGAGAGGCCGGCCCCTT

ACGTCAGAGGCGAGAATTCGACAACTTTGTATACAAAAGTTGTGGAACAC

GCAGATGCAGTCGGGGCGGCGCGGTCCCAGGTCCACTTCGCATATTAAGG

TGACGCGTGTGGCCTCGAACACCGAGCGACCCTGCAGCGACCCGCTTAAC

AGCGTCAACAGCGTGCCGCAGATCCACCCAACTTTTCTATACAAAGTTGC

TATGGAAGATGCCAAAAACATTAAGAAGGGCCCAGCGCCATTCTACCCAC

TCGAAGACGGGACCGCCGGCGAGCAGCTGCACAAAGCCATGAAGCGCTAC

GCCCTGGTGCCCGGCACCATCGCCTTTACCGACGCACATATCGAGGTGGA

CATTACCTACGCCGAGTACTTCGAGATGAGCGTTCGGCTGGCAGAAGCTA

TGAAGCGCTATGGGCTGAATACAAACCATCGGATCGTGGTGTGCAGCGAG

AATAGCTTGCAGTTCTTCATGCCCCGTGTTGGGTGCCCTGTTCATCGGTGT

GGCTGTGGCCCCAGCTAACGACATCTACAACGAGCGCGAGCTGCTGAACA

GCATGGGCATCAGCCAGCCCACCGTCGTATTCGTGAGCAAGAAAGGGCTG

CAAAAGATCCTCAACGTGCAAAAGAAGCTACCGATCATACAAAAGATCAT

CATCATGGATAGCAAGACCGACTACCAGGGCTTCCAAAGCATGTACACCT

TCGTGACTTCCCATTTGCCCACCCGGCTTCAACGAGTACGACTTCGTGCCC

GAGAGCTTCGACCGGGACAAAACCATCGCCCTGATCATGAACAGTAGTGG

CAGTACCGGATTGCCCAAGGGCGTAGCCCTACCGCACCGCACCGCTTGTG

TCCGATTCAGTCATGCCCGCGACCCCATCTTCGGCAACCAGATCATCCCC

GACACCGCTATCCTCAGCGTGGTGCCATTTCACCACGGCTTCGGCATGTT

CACCACGCTGGGCTACTTGATCTGCGGCTTTCGGGTCGTGCTCATGTACC

GCTTCGAGGAGGAGCTATTCTTGCGCAGCTTGCAAGACTATAAGATTCAA

TCTGCCCTGCTGGTGCCCACACTATTTAGCTTCTTCGCTAAGAGCACTCT

CATCGACAAGTACGACCTAAGCAACTTGCACGAGATCGCCAGCGGCGGGG

CGCCGCTCAGCAAGGAGGTAGGTGAGGCCGTGGCCAAACGCTTCCACCTA

CCAGGCATCCGCCAGGGCTACGGCCTGACAGAAACAACCAGCGCCATTCT

GATCACCCCCGAAGGGGACGACAAGCCTGGCGCAGTAGGCAAGGTGGTGC

CCTTCTTCGAGGCTAAGGTGGTGGACTTGGACACCGGTAAGACACTGGGT

GTGAACCAGCGCGGCGAGCTGTGCGTCCGTGGCCCCATGATCATGAGCGG

CTACGTTAACAACCCCGAGGCTACAAACGCTCTCATCGACAAGGACGGCT

GGCTGCACAGCGGCGACATCGCCTACTGGGACGAGGACGAGCACTTCTTC

ATCGTGGACCGGCTGAAGAGCCTGATCAAATACAAGGGCTACCAGGTAGC

CCCAGCCGAACTGGAGAGCATCCTGCTGCAACACCCCAACATCTTCGACG

CCGGGGTCGCCGGCCTGCCCGACGACGATGCCGGCGAGCTGCCCGCCGCA

GTCGTCGTGCTGGAACACGGTAAAACCATGACCGAGAAGGAGATCGTGGA

CTATGTGGCCAGCCAGGTTACAACCGCCAAGAAGCTGCGCGGTGGTGTTG

TGTTCGTGGACGAGGTGCCTAAAGGACTGACCGGCAAGTTGGACGCCCGC

AAGATCCGCGAGATTCTCATTAAGGCCAAGAAGGGCGGCAAGATCGCCGT

GTAAACAACTTTGTATAATAAAGTTGCTGATCCCAAGGCCCAACTCCCCG

AACCACTCAGGGTCCTGTGGACAGCTCACCTAGCTGCAATGGCTACAGGT

AAGCGCCCCTAAAATCCCTTTGGGCACAATGTGTCCTGAGGGGAGAGGCA

GCGACCTGTAGATGGGACGGGGGCACTAACCCTCAGGTTTGGGGCTTCTG

AATGTGAGTATCGCCATGTAAGCCCAGTATTTGGCCAATCTCAGAAAGCT

CCTGGTCCCTGGAGGGATGGAGAGAGAAAAACAAACAGCTCCTGGAGCAG

GGAGAGTGCTGGCCTCTTGCTCTCCGGCTCCCTCTGTTGCCCTCTGGTTT

CTCCCCAGGCTCCCGGACGTCCCTGCTCCTGGCTTTTGGCCTGCTCTGCC

TGCCCTGGCTTCAAGAGGGCAGTGCCTTCCCAACCATTCCCTTATCCAGG

CTTTTTGACAACGCTATGCTCCGCGCCCATCGTCTGCACCAGCTGGCCTT

TGACACCTACCAGGAGTTTGTAAGCTCTTGGGGAATGGGTGCGCATCAGG

GGTGGCAGGAAGGGGTGACTTTCCCCCGCTGGGAAATAAGAGGAGGAGAC
```

```
TAAGGAGCTCAGGGTTTTTCCCGAAGCGAAAATGCAGGCAGATGAGCACA
CGCTGAGTGAGGTTCCCAGAAAAGTAACAATGGGAGCTGGTCTCCAGCGT
AGACCTTGGTGGGCGGTCCTTCTCCTAGGAAGAAGCCTATATCCCAAGG
AACAGAAGTATTCATTCCTGCAGAACCCCCAGACCTCCCTCTGTTTCTCA
GAGTCTATTCCGACACCCTCCAACAGGGAGGAAACACAACAGAAATCCGT
GAGTGGATGCCTTCTCCCCAGGCGGGGATGGGGGAGACCTGTAGTCAGAG
CCCCCGGGCAGCACAGCCAATGCCCGTCCTTCCCTGCAGAACCTAGAGC
TGCTCCGCATCTCCCTGCTGCTCATCCAGTCGTGGCTGGAGCCCGTGCAG
TTCCTCAGGAGTGTCTTCGCCAACAGCCTGGTGTACGGCGCCTCTGACAG
CAACGTCTATGACCTCCTAAAGGACCTAGAGGAAGGCATCCAAACGCTGA
TGGGGGTGAGGGTGGCGCCAGGGGTCCCCAATCCTGGAGCCCCACTGACT
TTGAGAGCTGTGTTAGAGAAACACTGCTGCCCTCTTTTTAGCAGTCAGGC
CCTGACCCAAGAGAACTCACCTTATTCTTCATTTCCCCTCGTGAATCCTC
CAGGCCTTTCTCTACACCCTGAAGGGGAGGGAGGAAAATGAATGAATGAG
AAAGGGAGGGAACAGTACCCAAGCGCTTGGCCTCTCCTTCTCTTCCTTCA
CTTTGCAGAGGCTGGAAGATGGCAGCCCCCGGACTGGGCAGATCTTCAAG
CAGACCTACAGCAAGTTCGACACAAACTCACACAACGATGACGCACTACT
CAAGAACTACGGGCTGCTCTACTGCTTCAGGAAGGACATGGACAAGGTCG
AGACATTCTGCGCATCGTGCAGTGCCGCTCTGTGGAGGGCAGCTGTGGC
TTCTAGCTGCCCGGGTGGCATCCCTGTGACCCCTCCCCAGTGCCTCTCCT
GGCCCTGGAAGTTGCCACTCCAGTGCCCACCAGCCTTGTCCTAATAAAAT
TAAGTTGCATCATTTTGTCTGACTAGGCGTCCTTCTATAATATTATGGGG
TGGAGGGGGTGGTATGGAGCAAGGGGCAAGTTGGGAAGACAACCTGTAG
GGCCTGCGGGGTCTATTGGGAACCAAGCTGGAGTGCAGTGGCACAATCTT
GGCTCACTGCAATCTCCGCCTCCTGGGTTCAAGCGATTCTCCTGCCTCAG
CCTCCCGAGTTGTTGGGATTCCAGGCATGCATGACCAGGCTCAGCTAATT
TTTGTTTTTTTGGTAGAGACGGGGTTTCACCATATTGGCCAGGCTGGTCT
CCAACTCCTAATCTCAGGTGATCTACCCACCTTGGCCTCCCAAATTGCTG
GGATTACAGGCGTGAACCACTGCTCCCTTCCCTGTCCTTCTGATTTTAAA
ATAACTATACCAGCAGGAGGACGTCCAGACACAGCATAGGCTACCTGGCC
ATGCCCAACCGGTGGGACATTTGAGTTGTTTGCTTGGCACTGTCCTCTCA
TGCGTTGGGTCCACTCAGTAGATGCCTGTTGTACCCAGCTTTCTTGTACA
AAGTGGGATCTAGACTAGAGTCATCAGTCAATATGTTCACCCCAAAAAG
CTGTTTGTTAACTTGTCAACCTCATTCTAAAATGTATATAGAAGCCCAAA
AGACAATAACAAAAATATTCTTGTAGAACAAAATGGGAAAGAATGTTCCA
CTAAATATCAAGATTTAGAGCAAAGCATGAGATGTGTGGGGATAGACAGT
GAGGCTGATAAAATAGAGTAGAGCTCAGAAACAGACCCATTGATATATGT
AAGTGACCTATGAAAAAAATATGGCATTTTACAATGGGAAAATGATGATC
TTTTTCTTTTTTAGAAAAACAGGGAAATATATTTATATGTAAAAAATAAA
AGGGAACCCATATGTCATACCATACACACAAAAAAATTCCAGTGAATTAT
AAGTCTAAATGGAGAAGGCAAAACTTTAAATCTTTTAGAAAATAATATAG
```
```
AAGCATGCCATCAAGACTTCAGTGTAGAGAAAAATTTCTTATGACTCAAA
GTCCTAACCACAAAGAAAAGATTGTTAATTAGATTGCATGAATATTAAGA
CTTATTTTTAAAATTAAAAAACCATTAAGAAAAGTCAGGCCATAGAATGA
CAGAAAATATTTGCAACACCCCAGTAAAGAGAATTGTAATATGCAGATTA
TAAAAGAAGTCTTACAAATCAGTAAAAAATAAAACTAGACAAAAATTTG
AACAGATGAAAGAGAAACTCTAAATAATCATTACACATGAGAAACTCAAT
CTCAGAAATCAGAGAACTATCATTGCATATACACTAAATTAGAGAAATAT
TAAAAGGCTAAGTAACATCTGTGGCTTAATTAAAACAGTAGGATGACTGT
TT 3'

SEQ ID NO: 19: CreLuc hybrid transgene sequence
(Acc65I/PmeI digest, 5562 bp)
5'GTACCCGGGGGCGCGCCGGGATCCTTAATTAAAATTATCTCTAAGGCA
TGTGAACTGGCTGTCTTGGTTTTCATCTGTACTTCATCTGCTACCTCTGT
GACCTGAAACATATTTATAATTCCATTAAGCTGTGCATATGATAGATTTA
TCATATGTATTTTCCTTAAAGGATTTTTGTAAGAACTAATTGAATTGATA
CCTGTAAAGTCTTTATCACACTACCCAATAAATAATAAATCTCTTTGTTC
AGCTCTCTGTTTCTATAAATATGTACCAGTTTTATTGTTTTTAGTGGTAG
TGATTTTATTCTCTTTCTATATATATACACACATGTGTGCATTCATAA
ATATATACAATTTTTATGAATAAAAAATTATTAGCAATCAATATTGAAAA
CCACTGATTTTTGTTTATGTGAGCAAACAGCAGATTAAAAGGAATTCCTG
CAGGATCCTTAATTAAGTTCTAGATCCAAGTTTGTACAAAAAAGCAGGCT
TAGCACCAGACAGTGACGTCAGCTGCCAGATCCCATGGCCGTCATACTGT
GACGTCTTTCAGACACCCCATTGACGTCAATGGGAGAACGAATTCGCACC
AGACAGTGACGTCAGCTGCCAGATCCCATGGCCGTCATACTGTGACGTCT
TTCAGACACCCCATTGACGTCAATGGGAGAACACAACTTTGTATACAAAA
GTTGTGGAACACGCAGATGCAGTCGGGGCGGCGCGGTCCCAGGTCCACTT
CGCATATTAAGGTGACGCGTGTGGCCTCGAACACCGAGCGACCCTGCAGC
GACCCGCTTAACAGCGTCAACAGCGTGCCGCAGATCCACCCAACTTTTCT
ATACAAAGTTGCTATGGAAGATGCCAAAAACATTAAGAAGGGCCCAGCGC
CATTCTACCCACTCGAAGACGGGACCGCCGGCGAGCAGCTGCACAAAGCC
ATGAAGCGCTACGCCCTGGTGCCCGGCACCATCGCCTTTACCGACGCACA
TATCGAGGTGGACATTACCTACGCCGAGTACTTCGAGATGAGCGTTCGGC
TGGCAGAAGCTATGAAGCGCTATGGGCTGAATACAAACCATCGGATCGTG
GTGTGCAGCGAGAATAGCTTGCAGTTCTTCATGCCCGTGTTGGGTGCCCT
GTTCATCGGTGTGGCTGTGGCCCCAGCTAACGACATCTACAACGAGCGCG
AGCTGCTGAACAGCATGGGCATCAGCCAGCCCACCGTCGTATTCGTGAGC
AAGAAAGGGCTGCAAAAGATCCTCAACGTGCAAAAGAAGCTACCGGATCAT
ACAAAAGATCATCATCATGGATAGCAAGACCGACTACCAGGGCTTCCAAA
GCATGTACACCTTCGTGACTTCCCATTTGCCACCCGGCTTCAACGAGTAC
GACTTCGTGCCCGAGAGCTTCGACCGGGACAAAACCATCGCCCTGATCAT
GAACAGTAGTGGCAGTACCGGATTGCCCAAGGGCGTAGCCCTACCGCACC
```

-continued

```
GCACCGCTTGTGTCCGATTCAGTCATGCCCGCGACCCCATCTTCGGCAAC
CAGATCATCCCCGACACCGCTATCCTCAGCGTGGTGCCATTTCACCACGG
CTTCGGCATGTTCACCACGCTGGGCTACTTGATCTGCGGCTTTCGGGTCG
TGCTCATGTACCGCTTCGAGGAGGAGCTATTCTTGCGCAGCTTGCAAGAC
TATAAGATTCAATCTGCCCTGCTGGTGCCCACACTATTTAGCTTCTTCGC
TAAGAGCACTCTCATCGACAAGTACGACCTAAGCAACTTGCACGAGATCG
CCAGCGGCGGGGCGCCGCTCAGCAAGGAGGTAGGTGAGGCCGTGGCCAAA
CGCTTCCACCTACCAGGCATCCGCCAGGGCTACGGCCTGACAGAAACAAC
CAGCGCCATTCTGATCACCCCCGAAGGGGACGACAAGCCTGGCGCAGTAG
GCAAGGTGGTGCCCTTCTTCGAGGCTAAGGTGGTGGACTTGGACACCGGT
AAGACACTGGGTGTGAACCAGCGCGGCGAGCTGTGCGTCCGTGGCCCCAT
GATCATGAGCGGCTACGTTAACAACCCCGAGGCTACAAACGCTCTCATCG
ACAAGGACGGCTGGCTGCACAGCGGCGACATCGCCTACTGGGACGAGGAC
GAGCACTTCTTCATCGTGGACCGGCTGAAGAGCCTGATCAAATACAAGGG
CTACCAGGTAGCCCCAGCCGAACTGGAGAGCATCCTGCTGCAACACCCCA
ACATCTTCGACGCCGGGGTCGCCGGCCTGCCCGACGACGATGCCGGCGAG
CTGCCCGCCGCAGTCGTCGTGCTGAACACGGTAAAACCATGACCGAGAA
GGAGATCGTGGACTATGTGGCCAGCCAGGTTACAACCGCCAAGAAGCTGC
GCGGTGGTGTTGTGTTCGTGGACGAGGTGCCTAAAGGACTGACCGGCAAG
TTGGACGCCCGCAAGATCCGCGAGATTCTCATTAAGGCCAAGAAGGGCGG
CAAGATCGCCGTGTAAACAACTTTGTATAATAAAGTTGCTGATCCCAAGG
CCCAACTCCCCGAACCACTCAGGGTCCTGTGGACAGCTCACCTAGCTGCA
ATGGCTACAGGTAAGCGCCCCTAAAATCCCTTTGGGCACAATGTGTCCTG
AGGGGAGAGGCAGCGACCTGTAGATGGGACGGGGGCACTAACCCTCAGGT
TTGGGGCTTCTGAATGTGAGTATCGCCATGTAAGCCCAGTATTTGGCCAA
TCTCAGAAAGCTCCTGGTCCCTGGAGGGATGGAGAGAGAAAAACAAACAG
CTCCTGGAGCAGGGAGAGTGCTGGCCTCTTGCTCTCCGGCTCCCTCTGTT
GCCCTCTGGTTTCTCCCCAGGCTCCCGGACGTCCCTGCTCCTGGCTTTTG
GCCTGCTCTGCCTGCCCTGGCTTCAAGAGGGCAGTGCCTTCCCAACCATT
CCCTTATCCAGGCTTTTTGACAACGCTATGCTCCGCGCCCATCGTCTGCA
CCAGCTGGCCTTTGACACCTACCAGGAGTTTGTAAGCTCTTGGGGAATGG
GTGCGCATCAGGGGTGGCAGGAAGGGGTGACTTTCCCCCGCTGGGAAATA
AGAGGAGGAGACTAAGGAGCTCAGGGTTTTTCCCGAAGCGAAATGCAGG
CAGATGAGCACACGCTGAGTGAGGTTCCCAGAAAAGTAACAATGGGAGCT
GGTCTCCAGCGTAGACCTTGGTGGGCGGTCCTTCTCCTAGGAAGAAGCCT
ATATCCCAAAGGAACAGAAGTATTCATTCCTGCAGAACCCCCAGACCTCC
CTCTGTTTCTCAGAGTCTATTCCGACACCCTCCAACAGGGAGGAAACACA
ACAGAAATCCGTGAGTGGATGCCTTCTCCCCAGGCGGGGATGGGGGAGAC
CTGTAGTCAGAGCCCCGGGCAGCACAGCCAATGCCCGTCCTTCCCCTGC
AGAACCTAGAGCTGCTCCGCATCTCCCTGCTGCTCATCCAGTCGTGGCTG
GAGCCCGTGCAGTTCCTCAGGAGTGTCTTCGCCAACAGCCTGGTGTACGG
```

-continued

```
CGCCTCTGACAGCAACGTCTATGACCTCCTAAAGGACCTAGAGGAAGGCA
TCCAAACGCTGATGGGGGTGAGGGTGGCGCCAGGGGTCCCCAATCCTGGA
GCCCCACTGACTTTGAGAGCTGTGTTAGAGAAACACTGCTGCCCTCTTTT
TAGCAGTCAGGCCCTGACCCAAGAGAACTCACCTTATTCTTCATTTCCCC
TCGTGAATCCTCCAGGCCTTTCTCTACACCCTGAAGGGGAGGGAGGAAAA
TGAATGAATGAGAAAGGGAGGGAACAGTACCCAAGCGCTTGGCCTCTCCT
TCTCTTCCTTCACTTTGCAGAGGCTGGAAGATGGCAGCCCCCGGACTGGG
CAGATCTTCAAGCAGACCTACAGCAAGTTCGACACAAACTCACACAACGA
TGACGCACTACTCAAGAACTACGGGCTGCTCTACTGCTTCAGGAAGGACA
TGGACAAGGTCGAGACATTCCTGCGCATCGTGCAGTGCCGCTCTGTGGAG
GGCAGCTGTGGCTTCTAGCTGCCCGGGTGGCATCCCTGTGACCCCTCCCC
AGTGCCTCTCCTGGCCCTGGAAGTTGCCACTCCAGTGCCCACCAGCCTTG
TCCTAATAAAATTAAGTTGCATCATTTTGTCTGACTAGGCGTCCTTCTAT
AATATTATGGGGTGGAGGGGGGTGGTATGGAGCAAGGGGCAAGTTGGGAA
GACAACCTGTAGGGCCTGCGGGGTCTATTGGGAACCAAGCTGGAGTGCAG
TGGCACAATCTTGGCTCACTGCAATCTCCGCCTCCTGGGTTCAAGCGATT
CTCCTGCCTCAGCCTCCCGAGTTGTTGGGATTCCAGGCATGCATGACCAG
GCTCAGCTAATTTTTGTTTTTTTGGTAGAGACGGGGTTTCACCATATTGG
CCAGGCTGGTCTCCAACTCCTAATCTCAGGTGATCTACCCACCTTGGCCT
CCCAAATTGCTGGGATTACAGGCGTGAACCACTGCTCCCTTCCCTGTCCT
TCTGATTTTAAAATAACTATACCAGCAGGAGGACGTCCAGACACAGCATA
GGCTACCTGGCCATGCCCAACCGGTGGGACATTTGAGTTGTTTGCTTGGC
ACTGTCCTCTCATGCGTTGGGTCCACTCAGTAGATGCCTGTTGTACCCAG
CTTTCTTGTACAAAGTGGGATCTAGACTAGAGTCATCAGTCAATATGTTC
ACCCCAAAAAAGCTGTTTGTTAACTTGTCAACCTCATTCTAAAATGTATA
TAGAAGCCCAAAAGACAATAACAAAAATATTCTTGTAGAACAAAATGGGA
AAGAATGTTCCACTAAATATCAAGATTTAGAGCAAAGCATGAGATGTGTG
GGGATAGACAGTGAGGCTGATAAAATAGAGTAGAGCTCAGAAACAGACCC
ATTGATATATGTAAGTGACCTATGAAAAAAATATGGCATTTTACAATGGG
AAAATGATGATCTTTTTCTTTTTTAGAAAAACAGGGAAATATATTTATAT
GTAAAAAATAAAAGGGAACCCATATGTCATACCATACACACAAAAAAATT
CCAGTGAATTATAAGTCTAAATGGAGAAGGCAAAACTTTAAATCTTTTAG
AAAATAATATAGAAGCATGCCATCAAGACTTCAGTGTAGAGAAAAATTTC
TTATGACTCAAAGTCCTAACCACAAAGAAAAGATTGTTAATTAGATTGCA
TGAATATTAAGACTTATTTTTAAAATTAAAAAACCATTAAGAAAAGTCAG
GCCATAGAATGACAGAAAATATTTGCAACACCCCAGTAAAGAGAATTGTA
ATATGCAGATTATAAAAAGAAGTCTTACAAATCAGTAAAAAATAAAACTA
GACAAAAATTTGAACAGATGAAAGAGAAACTCTAAATAATCATTACACAT
```

-continued

```
GAGAAACTCAATCTCAGAAATCAGAGAACTATCATTGCATATACACTAAA

TTAGAGAAATATTAAAAGGCTAAGTAACATCTGTGGCTTAATTAAAACAG

TAGGATGACTGTTT
```

B. Founder Generation:

The transgenes were separately microinjected into the pronuclei of FVB/Taconic one-celled embryos. General strategies for generating transgenic (Tg) animals has been well described and are known to the skilled artisan.

Using a PCR genotyping strategy, transgenic positive founder mice were identified shortly after birth through tail biopsies and a PCR for genotype. The selected primer pair allows the amplification of a short DNA sequence within the transgene sequence, yielding a specific 405-bp PCR product. PCR reaction mix is 1× Qiagen PCR buffer with MgCl2 (Qiagen, Valencia, Calif. cat #201205), 0.2 mM dNTPs, 0.4 uM primers, 0.5 units of Taq Polymerase. Cycling conditions are as follows: 1 cycle at 94° C.; 5 min, 35 cycles at 94° C.; 45 sec/57° C.; 45 sec/72° C.; 1 min, 1 cycle at 72° C.; 5 min The genotyping primers are as follows:

```
SEQ ID NO: 20: Luc2-forward primer:
5'-GAAGATGCCAAAAACATTAAGAAG-3'

SEQ ID NO: 21: Luc2-reverse primer:
5'-GATCTTTTGCAGCCCTTTCT-3'
```

For the synthetic CreLuc transgene, 39 transgene positive founders were produced (out of 181 born), and for the hybrid CreLuc transgene, 73 transgene positives (out of 244 born). The transgenic mouse lines are abbreviated as CreLuc.

V. Founder Expression Analysis

Figure 5A:
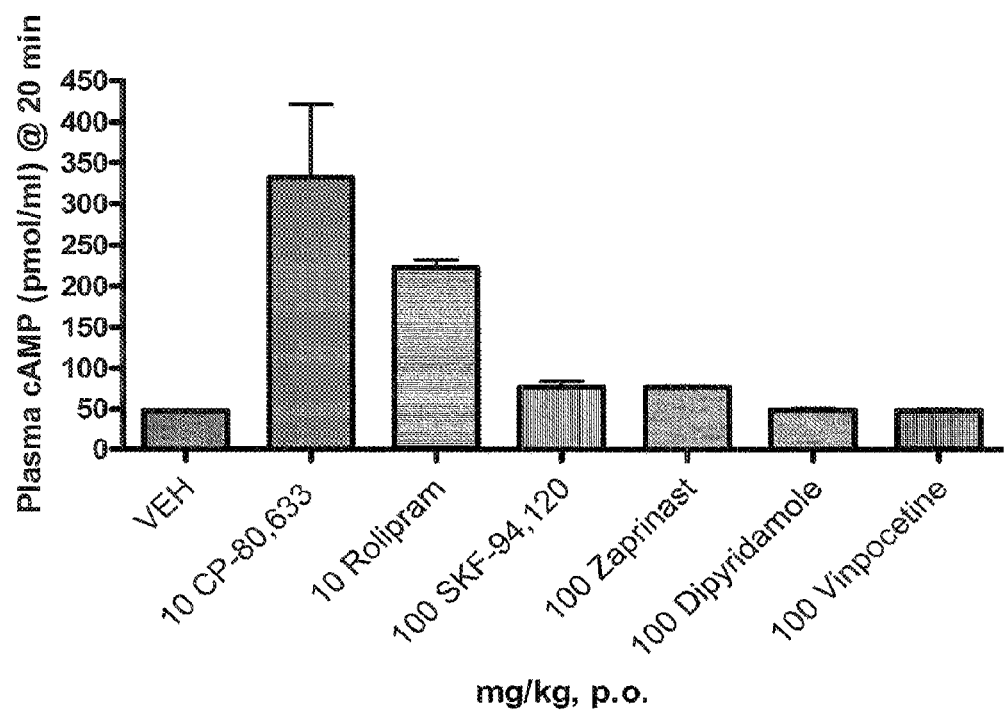
FIG. 5A shows the effects of PDE inhibitors on cAMP levels in normal mice. (reproduced from Cheng J B, JPET, 280, 621-626). Balb/c mice were dosed with either vehicle or drugs as listed on the x-axis, the blood was harvested after 20 minutes and assayed for cAMP by cAMP radioimmunoassay. Both CP-80,633 and rolipram significantly increase plasma cAMP levels at 10 mg/kg.

FIG. 5A is a comparison of the effects of different phosphodiesterase (PDE) inhibitors on plasma cAMP levels in normal mice (reproduced from Cheng et al, JPET, 280(2): 621-626, 1997). The mice were dosed p.o. with compound or vehicle (VEH) in groups of four animals. Twenty minutes later, blood was collected and processed for cAMP measurements. Based on this published experiment, rolipram was chosen as a general inducer along with forskolin for the CreLuc founder screen for its ability and its availability to increase cAMP levels. The additive effect of the two compounds when dosed together, provide a larger window of induction when examining luciferase levels in the animals.

Figure 5B:
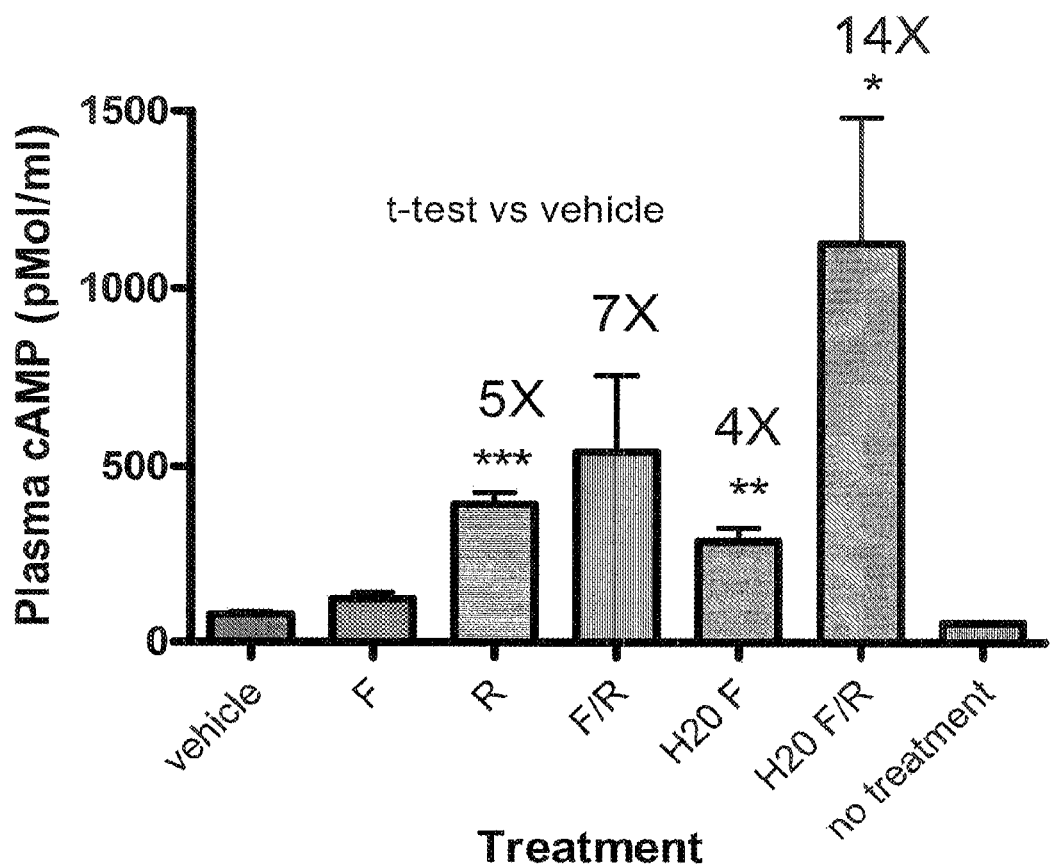
FIG. 5B shows in vivo stimulation of cAMP in plasma. FVB/Tac females were dosed with either vehicle (1% DMSO) or drugs i.p., then 30 minutes later, blood samples were collected and assayed for cAMP by ELISA (Assay Designs, Ann Arbor, Mich., cat#900-163). The drugs used are as follows: 5 mg/kg forskolin (F) (Sigma F6886), 5 mg/kg water soluble forskolin (H20F) (Calbiochem 344273), 10 mg/kg rolipram (R) (Sigma R6520) or combinations of either forskolin plus rolipram (F/R). Statistically significant increases, 14 fold, were observed with treatment of water soluble forskolin in combination with rolipram as determined by t-test. Forskolin increases cAMP levels by activating adenylate cyclase while inhibitors of PDE4, such as rolipram, raise plasma cAMP by preventing hydrolysis of cAMP. A combination of rolipram and water soluble forskolin increases cAMP levels in vivo 14 fold. This combination was used to provide a large window of induction for founder screening by bioimaging, a representative study is shown in FIG. 6.

FIG. 5B is a cAMP assay on plasma levels in wild-type mice following various treatment with forskolin (F), rolipram (R) or a combination of forskolin and rolipram (F/R). Two month old FVB/Tac females were dosed i.p. with one of the following: Group A: vehicle control, 1% dimethyl sulfoxide (DMSO) in phosphate buffered saline (PBS), Group B: 5 mg/kg forskolin (Sigma, St Louis Mo., cat#F6886), and Group C: 10 mg/kg rolipram (Sigma St Louis, Mo., cat#R6520), Group D: 5 mg/kg forskolin plus 10 mg/kg rolipram, Group E: 5 mg/kg water soluble forskolin (Calbiochem Gibbstown, N.J. cat#344273), and Group F: 5 mg/kg water soluble forskolin plus 10 mg/kg rolipram. Group G received no treatment. Compared to vehicle alone, rolipram and/or forskolin were statistically significance in their elevation of circulating cAMP levels. Forskolin alone did not significantly increase circulating cAMP over the vehicle control. The combination of water soluble forskolin (H2OF) and rolipram together had the greatest elevation in cAMP plasma levels and therefore indicated this treatment would be optimal for screening CreLuc founders for expression of the transgene in vivo.

Figure 6:
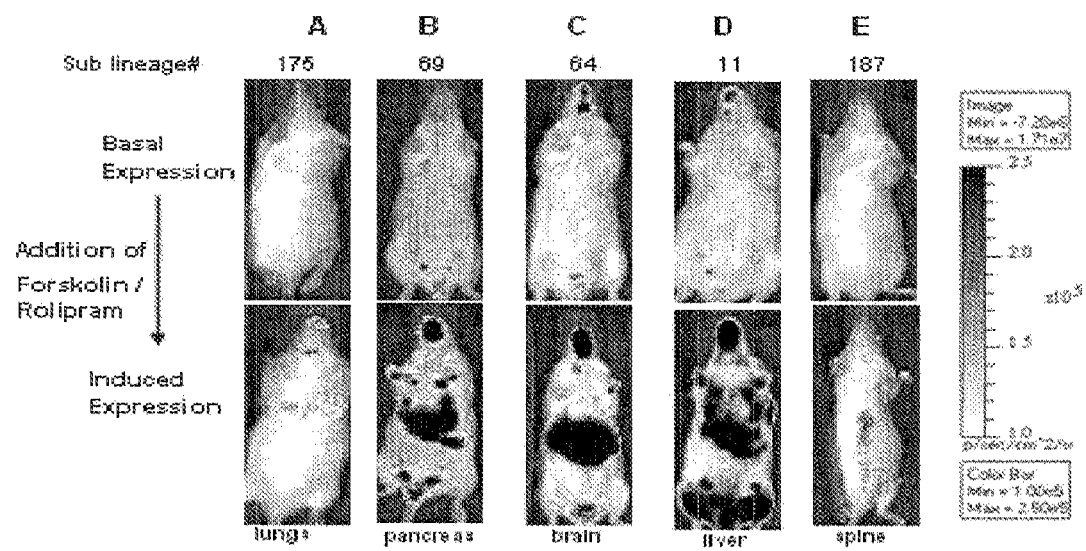
FIG. 6 shows the results of the initial founder induction and line selection for the CreLuc reporter mouse model. Multiple transgenic lines were screened for luciferase induction with forskolin and rolipram in vivo and then tissues were isolated and assayed for luciferase enzymes. Transgenic mice were bioimaged pre-dosing (basal expression levels), then the same mouse was dosed i.p. with 10 mg/kg rolipram and 5 mg/kg water soluble forskolin and bioimaged 4 hours post-dosing (induced expression). A (subline #90): forskolin/rolipram administration increased basal expression of CreLuc reporter transgene in the lungs and other tissues; B (subline #219): induction of basal expression is mainly in the gut; C(subline #44): undetectable basal expression and reporter is induced in brain plus other tissues; D (subline #28): undetectable basal expression that is increased in thymus and liver; E (subline #187): undetectable basal expression that is induced in the brain and spinal cord. As expected for a randomly integrated transgene, there was variation between lines in basal expression, tissue distribution, and response to induction. Twenty lines were identified to have greater than 5× induction in one or more tissues. Variation in tissue profile demonstrates that single tissue (i.e. lung, liver, brain) allows imaging devoid of background tissue response while multiple tissues allows a broad compound response profile to be generated.

All founders (founders listed in Tables 5-8 and representative founders shown in FIG. 6) were tested for transgene expression by dosing the mice i.p. with a combination of 10 mg/kg rolipram (Sigma St Louis, Mo., cat#R6520) and 5 mg/kg water soluble forskolin (Calbiochem Gibbstown, N.J. cat#344273). Four hours later, the mice were bioimaged using the Xenogen IVIS Lumina system. The mice were anesthetized with isoflurane, and 250 mg/kg luciferin was injected s.c. Eight minutes after the luciferin injection, mice were imaged. Of the 39 transgene positive synthetic CreLuc transgene, 34 or 87% were expression positive. For the hybrid transgene, 55 out of 71 or 78% of the mice tested were expression positive. Expression was considered to be positive when luciferase levels of any tissue are above the background levels for the system.

Various forskolin rolipram response profiles assayed by bioimaging of different independent lines of CreLuc mice is illustrated in FIG. 6. In the uninduced state we observed either detectable basal bioimaging signals as illustrated in line 90 and 219 or no basal activity as illustrated in lines 44,28, and 187. After forskolin rolipram induction the bioimaging pattern of CreLuc reporter induction occurred in single or multiple tissues and was unique in each independent CreLuc line. Many of the CreLuc lines had one or more tissues expressing detectable luciferase bioimages in therapeutically relevant areas.

Following a bioimaging screen of CreLuc expression in founders with both basal and forskolin rolipram induction, CreLuc lines that met a filter window of 5× bioimaging induction in one or more tissues (2× in the brain) were analyzed in more detail by assaying the induced levels of luciferase enzyme in tissue extracts.

For tissue expression analysis, animals were either left untreated for a baseline signal, or were induced for 4 hours. For induction, animals were dosed i.p. with a combination of 5 mg/kg Forskolin (Calbiochem, Gibbstown, N.J. cat#344273) and 10 mg/kg Rolipram (Sigma St Louis, Mo., cat#R6520) with 1% DMSO (Sigma, St Louis, Mo., cat#D2650) in Dulbecco's PBS (Invitrogen, Carlsbad, Calif., cat#14040). Four hours later, the animals were sacrificed by CO2 and the various organs were removed and frozen on dry ice. For the luciferase assay, the Luciferase Assay System (Promega, Madison, Wis., cat#E1500) was used. The tissues were homogenized in 1 ml of Cell Culture Lysis Buffer (Promega, Madison, Wis., cat#E1531), incubated on ice for 5 minutes, and then spun in a centrifuge for 5 minutes. 20 µl the supernatant was used in the assay as per manufacturers instructions. Protein concentrations of the samples were measured with the DC protein assay kit (BioRad, Hercules, Calif., cat#500-0111). Data is shown in Tables 5-8 and is presented as fold induction (induced RLU/ug protein divided by basal RLU/ug protein). RLU induced is the RLU/ug protein of the induced tissue sample.

TABLE 5

Luciferase Tissue Expression in Brain, Spleen and Kidney

| | Tissue | | | | | |
|---|---|---|---|---|---|---|
| | Brain | | Spleen | | Kidney | |
| Line | Fold Induction | RLU Induced | Fold Induction | RLU Induced | Fold Induction | RLU Induced |
| 561-24 | 1.6 | 1.55 | 66.6 | 71.3 | 2 | 60.9 |
| 561-44 | 1.8 | 1.2 | 7.3 | 98.7 | 0.2 | 5.0 |
| 561-90 | 4.5 | 1.0 | 20.6 | 12.1 | 21.5 | 132.5 |
| 562-11 | 3.9 | 0.6 | 11.1 | 4.7 | 17.4 | 1.4 |
| 562-16 | 0.9 | 2.7 | 18.2 | 5.4 | 147.5 | 82.0 |
| 562-31 | 1.0 | 48.9 | 3.0 | 3.1 | 3.0 | 119.3 |
| 562-33 | 1.0 | 3.3 | 1.0 | 2.1 | 80.6 | 53.8 |
| 562-64 | 1.0 | 3.7 | 39.5 | 565.2 | 45.9 | 47.7 |
| 562-69 | 2.5 | 1.7 | 52.2 | 44.8 | 30.6 | 36.1 |
| 562-175 | 2.1 | 81.3 | 0.5 | 0.4 | 3.6 | 12.9 |
| 562-180 | 1.2 | 0.2 | 38.9 | 6.9 | 131.9 | 23.8 |
| 562-184 | 1.0 | 2.5 | 11.0 | 26.0 | 6.0 | 71.2 |
| 562-187 | 3.1 | 3.0 | 9.6 | 6.0 | 17.7 | 4.2 |
| 562-219 | 2.0 | 4.8 | 2.0 | 3.8 | 2.0 | 103.0 |
| 562-229 | 1.4 | 3.1 | 76.1 | 111.9 | 302.6 | 154.3 |

TABLE 6

Luciferase Tissue Expression in Liver, Thymus and Pancreas

| | Tissue | | | | | |
|---|---|---|---|---|---|---|
| | Liver | | Thymus | | Pancreas | |
| Line | Fold Induction | RLU Induced | Fold Induction | RLU Induced | Fold Induction | RLU Induced |
| 561-24 | 29.4 | 25 | 10.6 | 93.4 | 152 | 108 |
| 561-44 | 16.2 | 3.5 | 2.3 | 3.2 | 4.5 | 2.0 |
| 561-90 | 14.5 | 19.2 | 1.3 | 11.8 | 117.8 | 78.6 |
| 562-11 | 1.5 | 0.5 | 1.5 | 3.6 | 28.7 | 26.4 |
| 562-16 | 89.9 | 12.9 | 2.7 | 9.7 | 753.7 | 442.6 |
| 562-31 | 768.0 | 132.6 | 2.0 | 11.4 | 204.0 | 199.6 |
| 562-33 | 53.6 | 40.3 | 3.0 | 4.9 | 0.6 | 0.9 |
| 562-64 | 62.8 | 104.3 | 4.5 | 505.5 | 321.7 | 900.7 |
| 562-69 | 115.7 | 108.6 | 0.6 | 18.5 | 508.7 | 197.3 |
| 562-175 | 17.9 | 2.5 | 3.2 | 3.5 | 0.4 | 0.5 |
| 562-180 | 259.7 | 21.3 | 7.3 | 4.9 | 889.0 | 130.5 |
| 562-184 | 9.0 | 7.7 | 1.0 | 16.0 | 118.0 | 76.7 |
| 562-187 | 18.7 | 105.3 | 4.9 | 23.6 | 496.8 | 155.6 |
| 562-219 | 1.0 | 2.2 | 1.0 | 3.1 | 15.0 | 20.3 |
| 562-229 | 337.7 | 206.0 | 33.5 | 157.7 | 258.0 | 503.1 |

TABLE 7

Luciferase Tissue Expression in Heart, Lungs and Spinal Cord

| | Tissue | | | | | |
|---|---|---|---|---|---|---|
| | Heart | | Lungs | | Spinal Cord | |
| Line | Fold Induction | RLU Induced | Fold Induction | RLU Induced | Fold Induction | RLU Induced |
| 561-24 | 2.1 | 2.4 | 6.2 | 10.9 | 1.1 | 14.5 |
| 561-44 | 2.4 | 0.7 | 0.6 | 1.9 | 1.2 | 8.7 |
| 561-90 | 3.0 | 1.5 | 6.8 | 7.7 | | |
| 562-11 | 11.1 | 2.9 | 2.5 | 7.4 | | |
| 562-16 | 1.1 | 1.9 | 3.2 | 7.3 | | |
| 562-31 | 4.0 | 2.2 | 26.0 | 17.4 | | |
| 562-33 | 2.1 | 1.9 | 8.1 | 10.0 | | |
| 562-64 | 3.9 | 8.4 | 3.2 | 36.7 | | |
| 562-69 | 0.6 | 0.7 | 0.5 | 1.1 | | |
| 562-175 | 1.4 | 0.6 | 12.5 | 228.0 | | |
| 562-180 | 1.5 | 0.6 | 1.8 | 0.9 | | |
| 562-184 | 1.0 | 0.6 | 1.0 | 2.1 | | |
| 562-187 | 1.3 | 1.4 | 0.4 | 5.0 | 0.9 | 2.9 |
| 562-219 | 2.0 | 3.6 | 27.0 | 318.4 | | |
| 562-229 | 5.2 | 7.4 | 17.3 | 40.8 | 0.3 | 7.6 |

TABLE 8

Luciferase Tissue Expression in Skin and Intestine

| | Tissue | | | |
|---|---|---|---|---|
| | Skin | | Intestine | |
| Line | Fold Induction | RLU Induced | Fold Induction | RLU Induced |
| 561-24 | 11.1 | 59 | 2.6 | 16 |
| 561-44 | | | | |
| 561-90 | | | | |
| 562-11 | 4.5 | 77.2 | | |
| 562-16 | 7 | 114 | 0.2 | 7.7 |
| 562-31 | 1 | 3.2 | 34 | 80.5 |
| 562-33 | 27 | 142 | 35 | 31.2 |
| 562-64 | 1.1 | 69 | 10.6 | 49.9 |
| 562-69 | 1.3 | 37.7 | 0.5 | 1.1 |
| 562-175 | 0.3 | 15.7 | 0 | 1.4 |
| 562-180 | 1 | 14.4 | | |
| 562-184 | 1 | 6.6 | 1 | |
| 562-187 | | | | |
| 562-219 | 4 | 51 | 6 | 4.2 |
| 562-229 | 12.1 | 144 | 1.5 | 43.3 |

This detailed level of CreLuc expression in each line allowed the selection of optimal lines with the highest expression levels in target tissues and the selection of lines with unique single or multiple patterns of expression. The enzyme assay also insured that CreLuc expression was clearly associated with a particular tissue, In general, as designed in the transgene we observed luciferase expression in nearly all tissues across the majority of the lines. The top 3-5 lines from key pharmaceutically relevant target tissues (brain, pancreas, lung, spleen) were selected for further reference compound response profiling using GPCR ligands.

VI. Analysis of the Effects of Insulator Elements on Expression Levels

In Table 9, the influence of adding insulator elements is compared across 11 different transgenes and including 225 independent transgenic lines. The production of functional transgenic lines ranges typically from 10-30% (historical data taken from our laboratory). As can be seen in Table 9, 10 of 11 transgenes and 190 lines obtained expression levels at the high end of this range (mean number of functional lines is 37 or 32.7%) due to the inclusion of the hGH minigene or functional enhancer. Significantly, the inclusion of insulator elements more than doubled this expression frequency and for 112 lines 78% express a functional reporter. The sample sizes for both comparisons and the diversity of the transgenes are large enough to overcome normal biological variation due to random integration of transgenes in the genome.

Generating transgenic bioimaging reporter lines is a low frequency, high attrition rate process. A large number of independent founder lines (50-100) are needed to obtain lines with the desired detection level for the reporter and to have the reporter expressed in a wide selection of target tissues appropriate for drug candidate screening. Typically 5% or less of lines are sufficient for drug screening applications and therefore the transgene containing the reporter has to include many elements to maximize the expression in each transgenic line generated. The insulator elements coupled to other expression enhancers (hGH minigene) has been demonstrated to yield a majority of transgenic lines that express the transgene and are key to finding transgenic lines with an expression pattern that is applicable to drug discovery (especially for various GPCR signaling pathways to detect a reduction in signal upon ligand to receptor binding).

TABLE 9

Comparison of the frequency of generating functional transgenic lines generated with either the hGH minigene and insulator elements

| | | | Founder Lines | | | |
|---|---|---|---|---|---|---|
| Transgene | Promoter | Functional Enhancer | Total # | # Positive | % Positive | Insulator |
| CD11ArtTA x tetEGFP ** | CD11A/ tet p | hGH minigene | 10 | 5 | 50% | none |
| CD11ArtTA X tetIL13 ** | CD11A/ tet p | hGH minigene | 9 | 3 | 33% | none |
| CC10rtTA x tetEGFP ** | CC10/ tet p | hGH minigene | 11 | 7 | 63% | none |
| hCXCR5-CD11a | CD11a | hGH minigene | 10 | 5 | 50% | none |
| hCXCR5-CD11b | CD11b | hGH minigene | 16 | 5 | 50% | none |
| MBP luci | MBP | hGH minigene | 35 | 6 | 17% | none |
| GP1 CRE | GP1 | hGH minigene | 7 | 2 | 29% | none |
| GP1 GFP | GP1 | hGH minigene | 7 | 4 | 57% | none |
| PF4 GFP | PF4 | hGH minigene | 8 | 0 | 0 | none |
| Totals | | | 113 | 37 | Ave. = 32.7% | |
| CreLuc Synthetic | HSV TK + 6X CRE | hGH minigene | 39 | 33 | 85% | yes * |
| CreLuc hybrid | HSV TK + 6X CRE | hGH minigene | 73 | 55 | 75% | yes * |
| Totals | | | 112 | 88 | Ave. = 78% | |

* beta globin/IFN,
** binary model

Legend: CD11 ArtTA, CD11a promoter expressing the reverse activator for tetracycline transactivator; TetEGFP is the tetracycline promoter expressing the EGFP reporter; TetIL13 is the tetracycline promoter expressing IL13; CC10rtTA; the CC10 lung specific promoter expressing the reverse activator for the tetracycline transactivator; hCXCR5- CD11a or b is the human CXCR5 promoter expressing the CD11a or CD11b coding cDNA; MBP luci is the myelin basic protein (MBP) promoter expressing luciferase (luci); GP1 and PF4- GFP; GP1 and PF4 are platelet specific promoters expressing the GFP reporter.

Deposit of Material:

Preparation of Mouse Embryonic Fibroblasts: Day 12 embryos were removed from pregnant females. The embryos were dissected out of the uterus in a 10 cm dish containing phosphate-buffered saline (PBS) (Invitrogen, Carlsbad, Calif., cat#14040). They were then transferred to a new dish of PBS. The embryos were teased apart with forceps and the heart and liver were removed. The tissue pieces were then incubated in 2-3 mls of cold 0.25% trypsin (Invitrogen, Carlsbad, Calif., cat#25200) overnight at 4° C. The next day, most of the trypsin was aspirated off and the tissue pellet was incubated for 30 minutes at 37° C. 2-3 ml of media, DMEM (Invitrogen, Carlsbad, Calif., cat#11965), 5% heat inactivated FBS (Invitrogen, Carlsbad, Calif., cat#16140), 1% pen strep (Invitrogen, Carlsbad, Calif., cat#15140) was added and pipetted up and down to break up the remaining clumps of tissue. The cell suspension was then plated onto one T75 tissue culture flasks. Cells were cultured for 3 passages and then frozen down in 1 ml vials, 1-2 million cells per vial, in freezing media, 15% heat inactivated FBS (Invitrogen, Carlsbad, Calif., cat#16140), 5% DMSO (Sigma, St Louis, Mo., cat#D2650), DMEM (Invitrogen, Carlsbad, Calif., cat#11965).

The following materials have been deposited with the American Type Culture Collection, 10801 University Blvd., Manassas, Va. 20110-2209, USA (ATCC):

TABLE 10

Deposit of Material

| Line | ATCC Deposit # | Identification Reference by Depositer |
|---|---|---|
| 562-11 | PTA-10536 | Mouse embryonic fibroblast:FVB/Creluc11 |
| 562-187 | PTA-10537 | Mouse embryonic fibroblast:FVB/Creluc187 |
| 562-229 | PTA-10538 | Mouse embryonic fibroblast:FVB/Creluc229 |

The deposit was made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between sanofi-aventis US Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto.

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

VII. In Vivo and Ex Vivo Screening Assays

Figure 7:
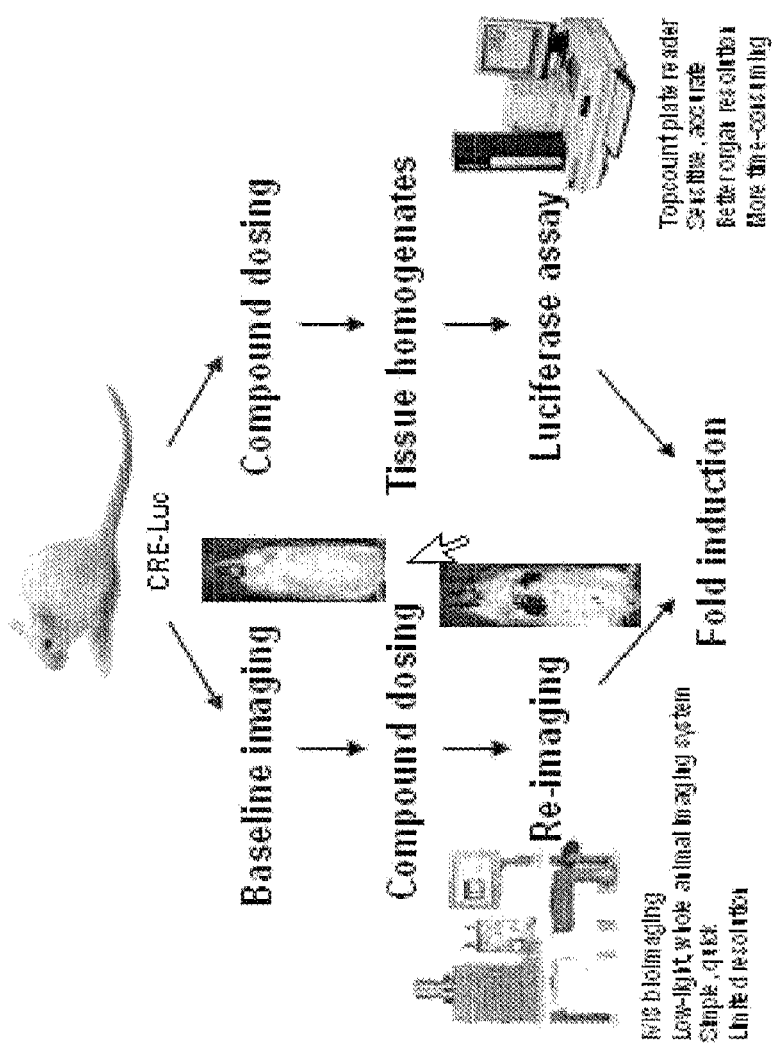
FIG. 7 shows a general schematic of CreLuc screening assays in vivo or ex vivo.

FIG. 7 shows embodiments of the invention by representing the flow of CreLuc screening assays either in vivo or ex vivo. For in vivo assays, the animals are dosed with luciferin only and then bioimaged on an IVIS bioimager to get baseline signal. The animals are then dosed with compound, and then bioimaged again at a set timepoint to examine the effects of the compound on the luciferase signal. Data can be analyzed as the fold induction of the induced signal versus the baseline signal. For the ex vivo assays, mice are dosed with either compound or vehicle, and then at a set timepoint, tissues are harvested and frozen. The tissues can then be homogenized and a luciferase assay such as Promega Luciferase assay system (Promega cat #E1500) run on the tissue extracts and the assay read on a luminometer such as the Topcount. Data can be analyzed as the relative light units per µg protein, comparing vehicle versus compound groups.

Additional aspects and details of the invention will be apparent from the following examples, which are intended to be illustrative and are not meant to limit the scope of the invention in any way.

A. Whole Brain Slices Experiments

Figure 8A:
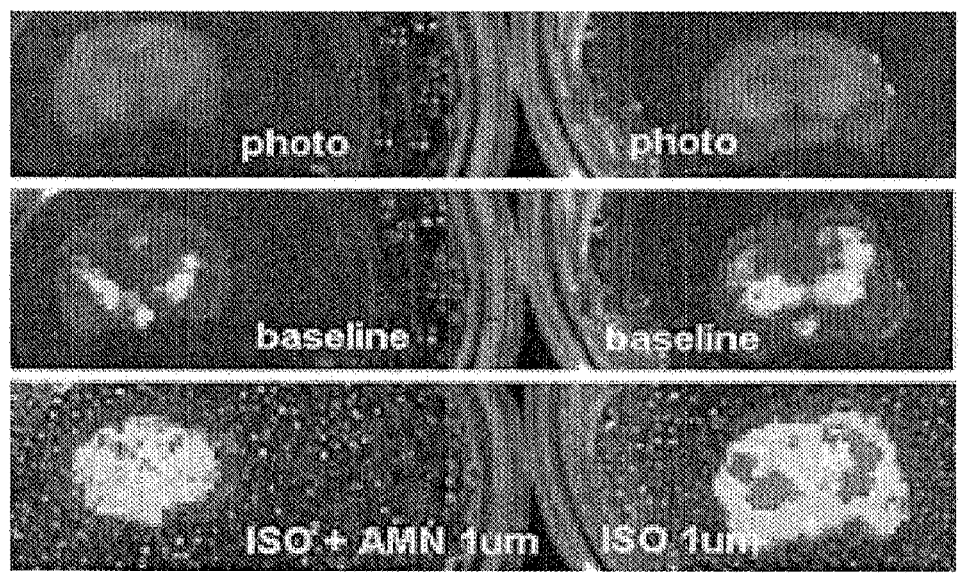
FIG. 8A shows the effects of isoproterenol (ISO) and AMN082 (AMN) on luminescence in whole brain slices from CreLuc mice (line 187).
Figure 8B:
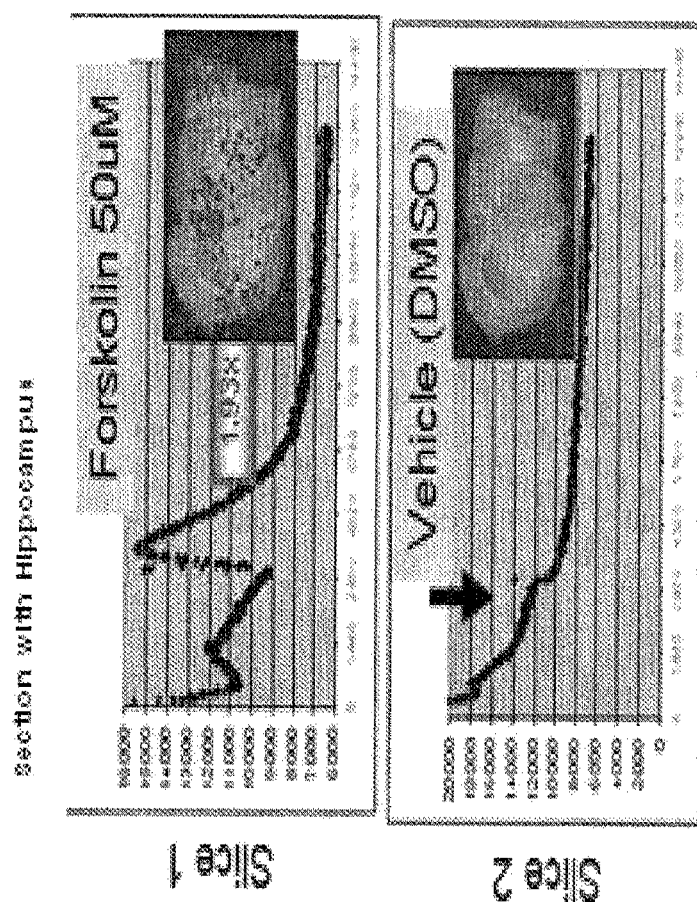
FIG. 8B shows the effects of forskolin on luminescence in whole brain slices from CreLuc mice (line 44) over time. Time is represented on the X-axis in minutes. Forskolin at 50 uM or vehicle (DMSO) was added at time=2880 marked by an arrow in the bottom panel.

Whole brain slices were used to show the effects of compounds on luminescence in CreLuc mice (FIG. 8A, 8B). In general, brains from CreLuc mice can be harvested and then either cut into slices on a microtome or various subregions can also be dissected out and then sliced on a microtome. The slices can then be incubated with different compounds such as forskolin and rolipram, or GPCR specific compounds. Luciferase levels can then be measured with an IVIS bioimager or a photomultiplier with a carousel to take quantitative timecourse measurements.

Brain slices from the hippocampal region of CreLuc mice (line #187) were incubated with 1 uM isoproterenol (Sigma, cat#5627) for 2 days. Isoproterenol (ISO) is a Gs agonist that activates the cAMP pathway (see FIG. 1 for pathway schematic) and induces luciferase expression levels in CreLuc mice. (FIG. 8A, bottom panel). Thus, isoproterenol was used to increase the luciferase signal window which allows for screening GPCR specific compounds such as Gi agonists. AMN082 (AMN, Tocris Bioscience, Cat. No. 2385) is an mGluR7 agonist and mGluR7 is a receptor that is coupled to Gi. When brain slices were treated with 1 uM ISO in combination with 1 uM AMN082, the luciferase signal was diminished in comparison to ISO treatment alone.

Compound activity can also be quantitated over time in a viable brain slice and luciferase expression can be visualized by a bioimager. In FIG. 8B, brain slices from CreLuc mice (line 44) were responsive to forskolin. Forskolin is a general activator of cAMP. Treatment of the brain slice with 50 uM forskolin (arrow marks the time of forskolin was added to the slice) caused an induction in time dependent manner compared to vehicle.

B. In Vitro Cell Culture Experiments

1. Primary Cortical Neurons

Figure 9:
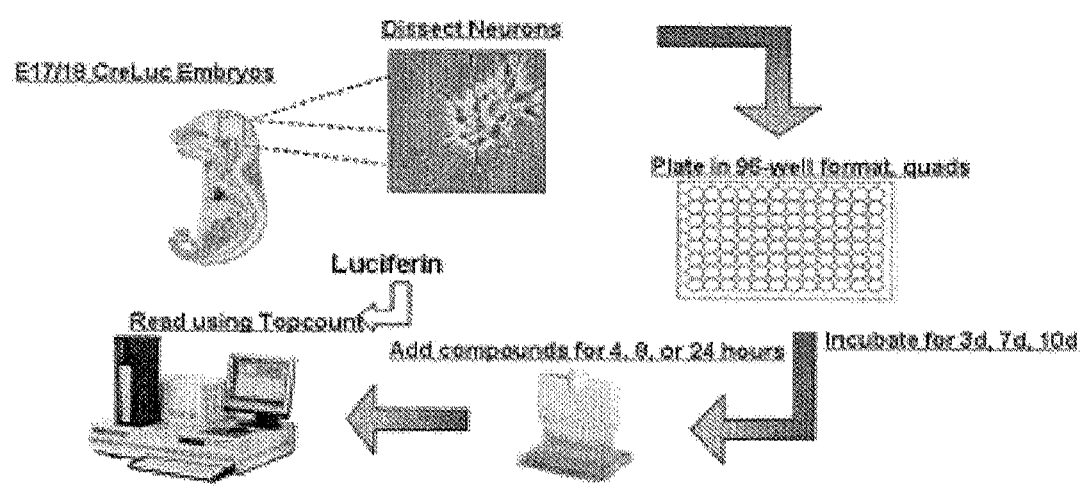
FIG. 9 shows a schematic representing the isolation and compound treatment of primary neuronal cells from the CreLuc mice.

A general schematic of the workflow for the isolation and compound treatment of primary neuronal cells from the CreLuc model is depicted in FIG. 9. Cortices or other brain subregions are removed from embryos, usually embryonic (E) day 17 or 18, but also as early as E14. The individual neurons are then isolated and plated onto 96 well assay plates. Assays are run either in triplicate or quadruplicate. The assays are run from day 3 in culture up until day 7 or day 10 in culture depending on the expression levels of the target GPCR. Compounds are added to the plates then at a set timepoint, Bright Glo (Promega, Cat #E2610) is added to the plates and the assay is then run on a TopCount or other luminometer.

a) Gs Modulation Via β Adrenergic Receptors (ADβR) and D1 Dopamine Receptors (DRD1)

Figure 24:
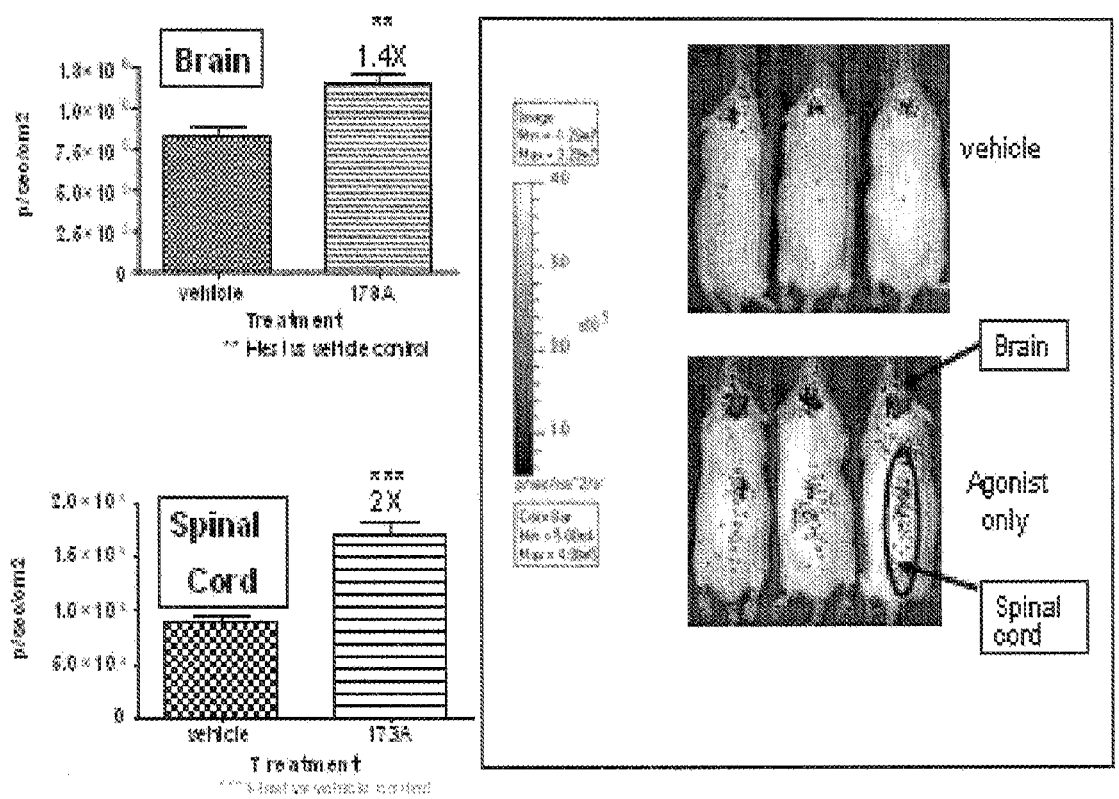
FIG. 24 shows the effects of the EP2 agonist, EX00000173A on luciferase expression in the brain and spinal cord of CreLuc mice. Mice (line 187) were injected i.p. with either vehicle (5% DMSO, 0.05% tween 80, PBS) or 10 mg/kg EX00000173A. Animals were bioimaged at 4 hours post doing. Data shown as photons per second per cm2.

Primary cell cultures from the CreLuc mice may be used to screen compounds that are capable of modulating Gs coupled receptors. Neurons were isolated from the cortices of line 187 E18 embryos. Line 187 has been shown to have inducible levels of luciferase in both the brain and spinal cord by whole tissue luciferase assays (see text below; FIG. 24). The assay was run in triplicates on day three in culture. Forskolin was used at 5 µM, rolipram at 10 µM and the Gs agonists, ADβR-isoproterenol; and Dopamine-SKF82958 (MFG, Cat #C130) at 10 µM. At 4 hours, Bright Glo was added and the assays run on a Topcount. Forskolin is a general activator of cAMP. Rolipram does not activate cAMP, instead, rolipram blocks the breakdown of cAMP, thereby stabilizing the cAMP levels. Forskoline and rolipram act synergistically to increase luciferase expression. An induction of over 100 fold was observed with a combination of forskolin and rolipram. Increased luci levels were seen with ADβR agonist isoproterenol (11 fold) vs. DMSO control. While the D1 DR agonist, SKF82958, did not significantly increase luciferase levels, a 2-fold induction was observed when SKF82958 was administered in combination with rolipram when compared to rolipram alone. Thus, line 187 is a useful model for screening compounds to determine if the compound is able to modulate Gs coupled receptors.

b) Gq Modulation Via Prokineticin 2 Receptor (PROK2R)

Primary cell cultures from the CreLuc mice may be used to screen compounds that are capable of modulating Gs coupled receptors. The PROK2R is Gq coupled, therefore, prokineticin 2 (PROK2) which is an agonist for the PROK2R was used to see whether CreLuc mice would be responsive to Gq modulation. Gq bypasses cAMP but utilizes the PLC pathway to activate CREB (see pathway schematic of FIG. 1). Primary cortical neurons were harvested from line 187 (which was shown to have inducible luciferase in brain and spinal cord—see text below and FIG. 24) on E18. The assay was run on day 3 in culture for 4 hours, or 8 hours. The PROK2 peptide (Peprotech, Cat#100-46) is added as an aqueous solution at 1 nM and 100 nM. Bright Glo was used for the luciferase signal, and the assay was run on a TopCount luminometer. Highly significant increases in luciferase levels vs. the media only control are observed at both timepoints, for both concentrations of PROK2. Thus, the CreLuc mice can be used to screen for compounds that modulate Gq coupled receptors.

The effects of PROK2 peptide on luciferase expression in primary cortical neurons from different CreLuc lines was examined. Primary cortical neurons were harvested from four different CreLuc lines at E18. Lines were selected based on earlier experiments which determined inducible luciferase levels in whole brain extracts (data not shown). The assays were run in triplicate at day three in culture with either 1 nM or 100 nM PROK2 peptide at two timepoints, 4 hours and 24 hours. BrightGlo was used for the assay and read on a TopCount. Statistically significant increases in luciferase levels were observed at both timepoints and at both concentrations for lines 219 and 175. Even though all lines responded to the PROK2 ligand to some degree, differences in luciferase expression levels may be due to differences in transgene integration.

c) Gi Modulation Via mGluR7 Receptors

Figure 13A:
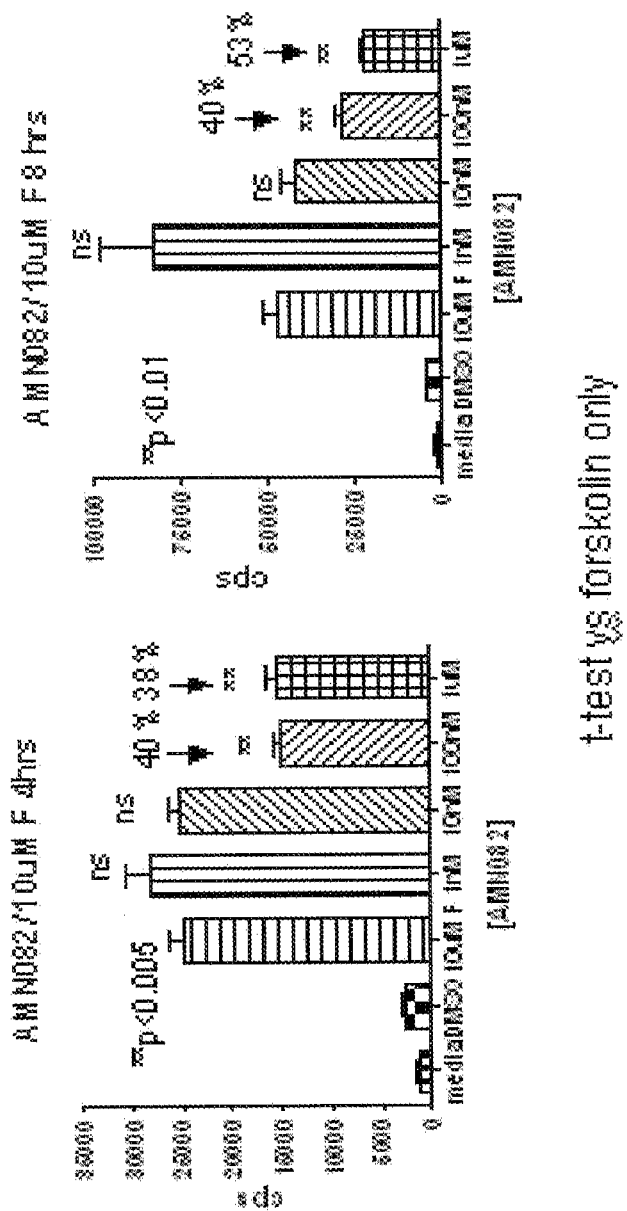
FIG. 13A shows the effects of the mGluR7 agonist, AMN082 on luciferase expression in primary cortical neurons. Cortical neurons were harvested from E18 embryos (line 187). The assay was run at day 3 in culture. Forskolin was used at 10 $\mu$M. The agonist, AMN082 was used in combination with forskolin at 1 nM, 10 nM, 100 nM and 1 $\mu$M. The assay was read on a TopCount with Bright Glo (Promega) at 4 hours, and 8 hours. Data is shown as counts per second (cps)
Figure 13B:
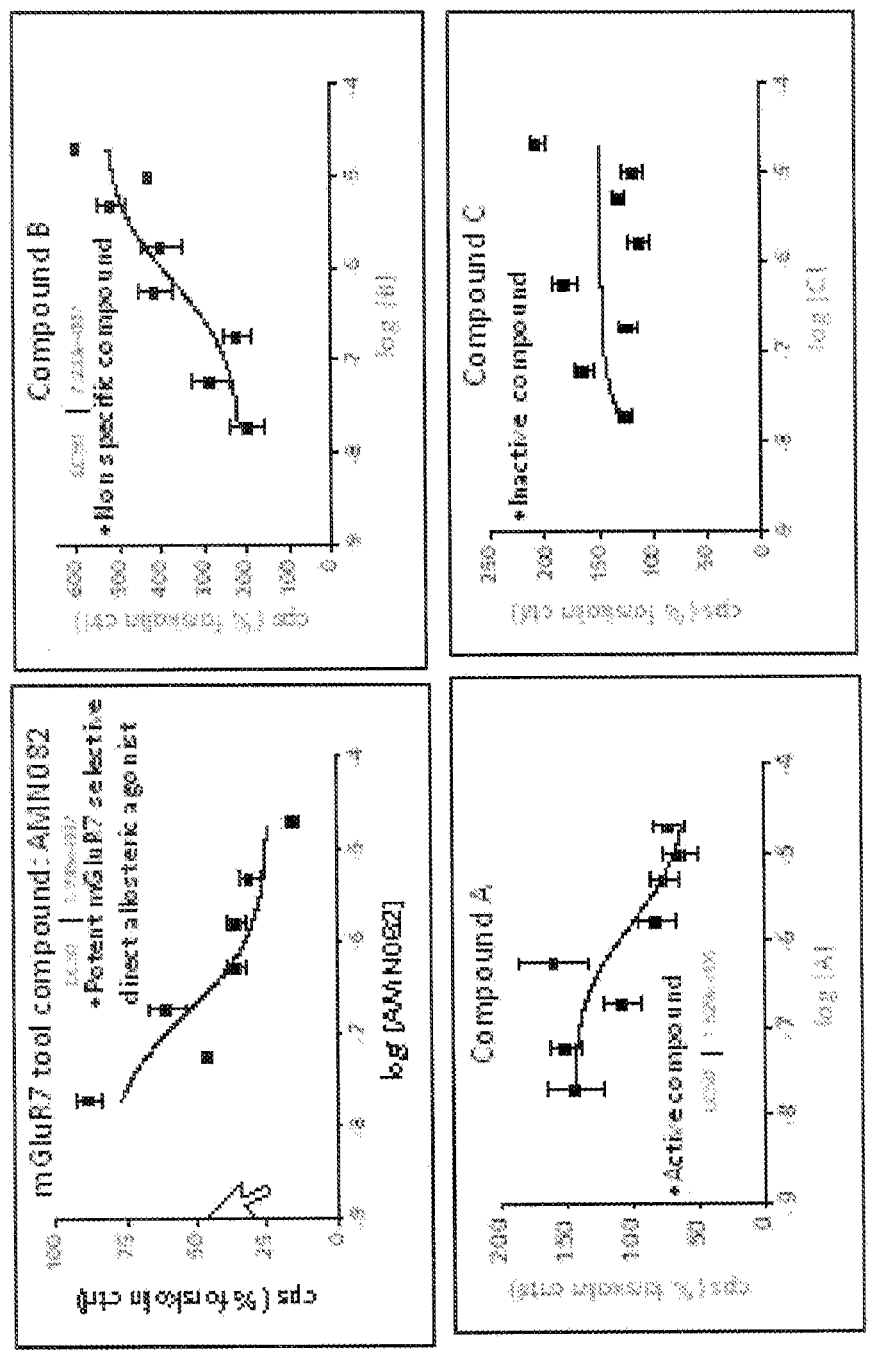
FIG. 13B shows the results of screening unknown compounds for the ability to modulate Gi activity in primary cortical neurons. Cortical neurons were harvested from E18 embryos (line 187). The assay was run at day 3 in culture. Forskolin was used at 10 $\mu$M. AMN082 or unknown compounds A, B or C was tested in combination with forskolin at different concentration and EC50 values were calculated. The assay was read on a TopCount with Bright Glo (Promega) at 4 hours. Data is shown as counts per second (cps)
Figure 14:
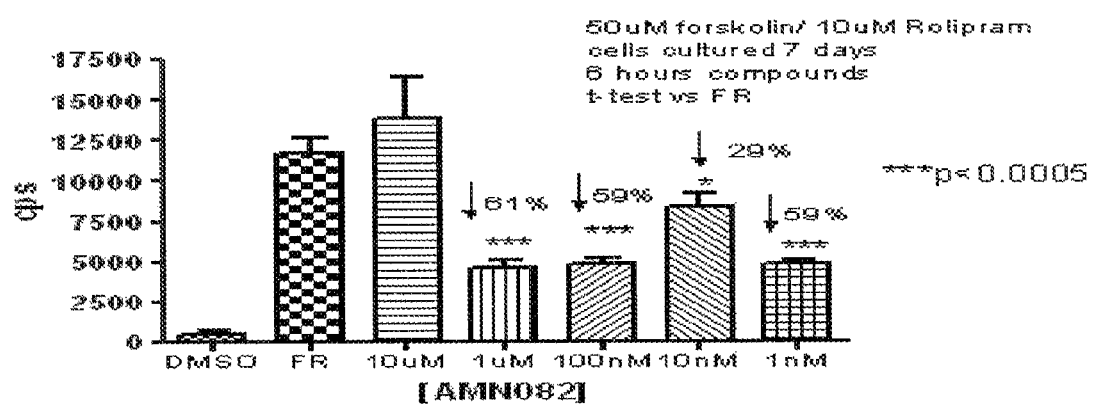
FIG. 14 shows the effects of the mGluR7 agonist, AMN082 on luciferase expression in primary cortical neurons. Primary cortical neurons were isolated from E18 embryos from line 187. The assay, in triplicates, was run at day 7 in culture for 6 hours. A concentration curve for AMN082 was run in combination with 50 $\mu$M forskolin and 10 $\mu$M rolipram. The assay was read on a TopCount luminometer with Bright Glo substrate (Promega). Data is shown as counts per second (cps)

Primary cell cultures from the CreLuc mice may be used to screen compounds that are capable of modulating Gi coupled receptors. FIG. 13A shows the effects of the mGluR7 agonist, AMN082 on luciferase expression in primary cortical neurons. Cortical neurons were harvested from E18 embryos (line 187). The assay was run at day 3 in culture. Forskolin was used at 10 µM to give a larger signal window to be used to detect Gi activity. The mGluR7 agonist, AMN082 was used in combination with forskolin at 1 nM, 10 nM, 100 nM and 1 µM. The assay was read on a TopCount with Bright Glo (Promega) at 4 hours, and 8 hours. Significant decreases in luciferase levels, versus forskolin only, are observed at 100 nM and 1 µM AMN082 for both timepoints. The CreLuc mice can be used to screen for compounds that modulate Gq coupled receptors. For example, "unknown" compounds designated "A", "B" and "C" were screened in primary cortical neuronal cultures using AMN082 as an internal control to determine if any compounds exhibited Gi modulating ability (FIG. 13B). Compound A would be considered an active compound with a calculated EC50=1.529e-06 compared to the known mGluR7 agonist AMN082 which had an EC50=1.735e-07 while compound B would be considered a non-specific compound and compound C is inactive.

Figure 15A:
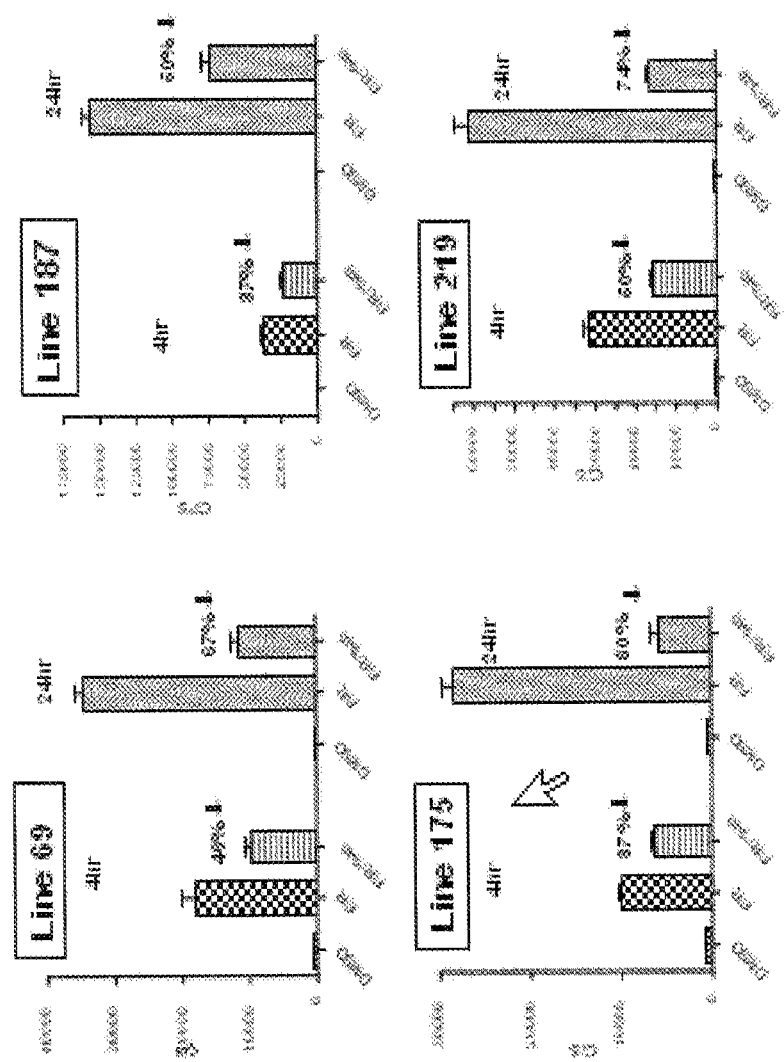
FIG. 15A shows Gi modulation of luciferase expression in primary cortical neurons from different CreLuc lines by the CB1 agonist, CP 55,940. Primary cortical neurons were harvested from four different CreLuc lines at E18. The assays were run on day three in culture. The CB1 agonist was used at 10 $\mu$M, forskolin at 5 $\mu$M and rolipram at 10 $\mu$M. Two timepoints were run, four hours and twenty-four hours. Bright Glo luciferase assay substrate was then added, and the assay read on a Topcount luminometer. Data shown is the average of the triplicates. Data is shown as counts per second (cps).

Screening compounds for the ability to modulate Gi coupled receptors using primary cell cultures from the CreLuc mice may be done in the presence of a cAMP stimulator such as forskolin as demonstrated above. However, to increase the signal window even wider, rolipram (blocks the breakdown of cAMP) was used in combination with forskolin. Primary cortical neurons were isolated from E18 embryos from line 187 which was previously determined to have inducible brain and spinal cord expression. The assay, in triplicates, was run at day 7 in culture for 6 hours. A dose curve, 10 µM down to 1 nM, for AMN082 was run in combination with 50 µM forskolin and 10 µM rolipram. The assay was read on a TopCount luminometer with Bright Glo substrate (Promega). Statistically significant decreases, p<0.0005, in luciferase levels (59-61% vs. forskolin and rolipram controls) are seen at 1 µM, 100 nM and 1 nM. Gi modulation of luciferase expression in primary cortical neurons from different CreLuc lines by the CB1 agonist, CP 55,940 was performed in the presence of forskolin and rolipram (FIG. 15). Primary cortical neurons were harvested from lines 69, 187, 175 and 219 at E18. All lines used were previously determined to have inducible luciferase expression levels in whole brain tissue extracts (data not shown). The assays were run on day three in culture. The CB1 agonist was used at 10 µM, forskolin at 5 µM and rolipram at 10 µM. Two timepoints were run, four hours and twenty-four hours. Bright Glo luciferase assay substrate was then added, and the assay read on a Topcount luminometer. The assay was run in triplicate. Data shown is the average of the triplicates. Data is shown as counts per second (cps). Decreased signals in luciferase are observed in all four lines at both timepoints with the addition of the CB1 agonist. Slight differences in response levels may be due to transgene integration, but all lines were responsive to Gi modulation and would be amendable to screening compounds for Gi activity.

Figure 15B:
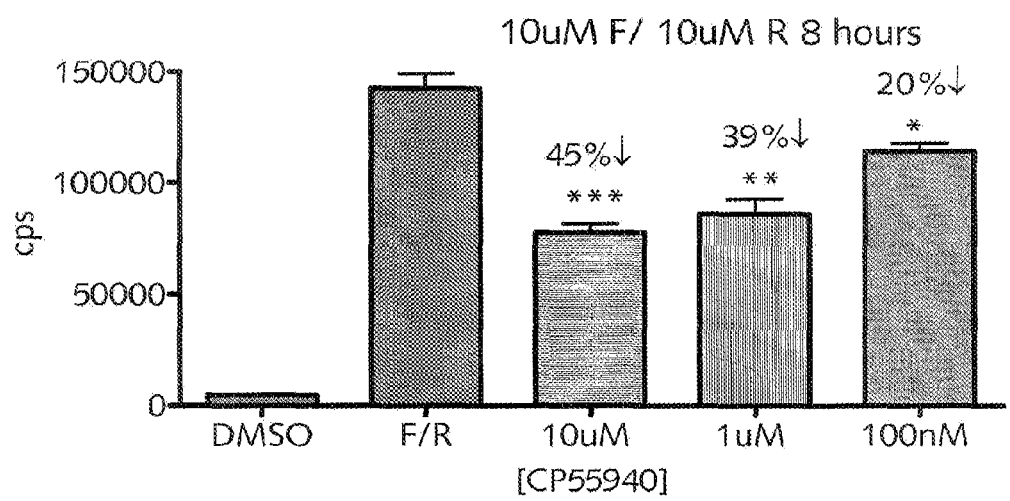
FIG. 15B shows Gi modulation of luciferase in primary cortical neurons from CreLuc mice by the CB1 agonist, CP 55,940. Cortical neurons were isolated from E18 embryos (line 187). The assay was run on day 3 in culture. Forskolin (F) and rolipram (R) were used at 10 $\mu$M. The agonist was added at concentrations of 10 $\mu$M, 1 $\mu$M and 100 nM. The assay was read on a TopCount with BrightGlo (Promega) at 8 hours. Data is shown as counts per second (cps).

Gi modulation of luciferase in primary cortical neurons from CreLuc mice by the CB1 agonist, CP 55,940 was in a dose-dependent manner (FIG. 15B). Cortical neurons were isolated from E18 embryos. The assay was run on day 3 in culture. Forskolin and rolipram were used at 10 µM. The agonist was added at concentrations of 10 µM, 1 µM and 100 nM. The assay was read on a TopCount with BrightGlo (Promega) at 8 hours. Significant decreases in luciferase levels, (agonist plus forskolin and rolipram versus forskolin and rolipram alone) are observed at all 3 concentrations.

2. Primary Striatal Neurons

Figure 10:
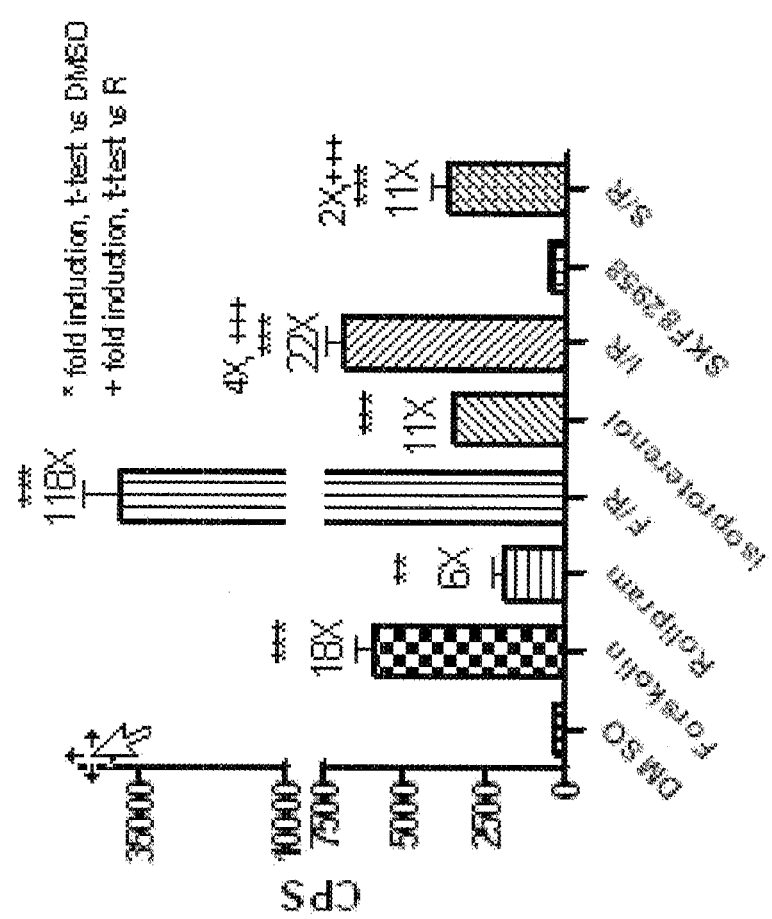
FIG. 10 shows Gs modulation via β-adrenergic receptor (ADβR) activation and D1 dopamine receptor (DRD1) activation. Neurons were isolated from the cortices of line 187 E18 embryos. On day three in culture, test compounds were added Forskolin 5 $\mu$M (F), rolipram at 10 $\mu$M (R), forskoline and rolipram in combination (F/R) isoproterenol at 10 $\mu$M, isoproterenol and rolipram in combination (I/R); SKF82958 at 10 $\mu$M, and SKF82958 and rolipram in combination (S/R). Data is shown as counts per second (cps)
Figure 11:
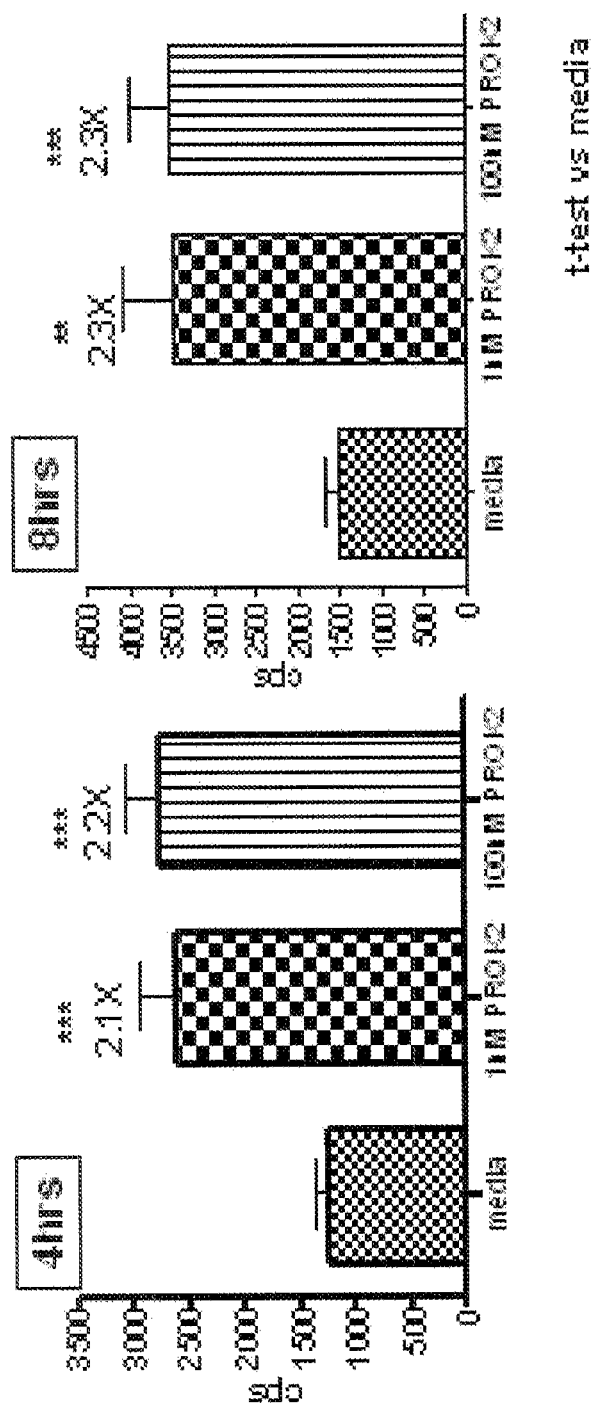
FIG. 11 shows the effects of prokineticin 2 (PROK2) peptide on luciferase expression in primary cortical neurons. Primary cortical neurons were harvested from line 187 (inducible luciferase in brain and spinal cord) on E18. The assay was run on day 3 in culture for 4 hours or 8 hours. The PROK2 peptide is added as an aqueous solution at 1 nM and 100 nM. Data is shown as counts per second (cps)
Figure 12:
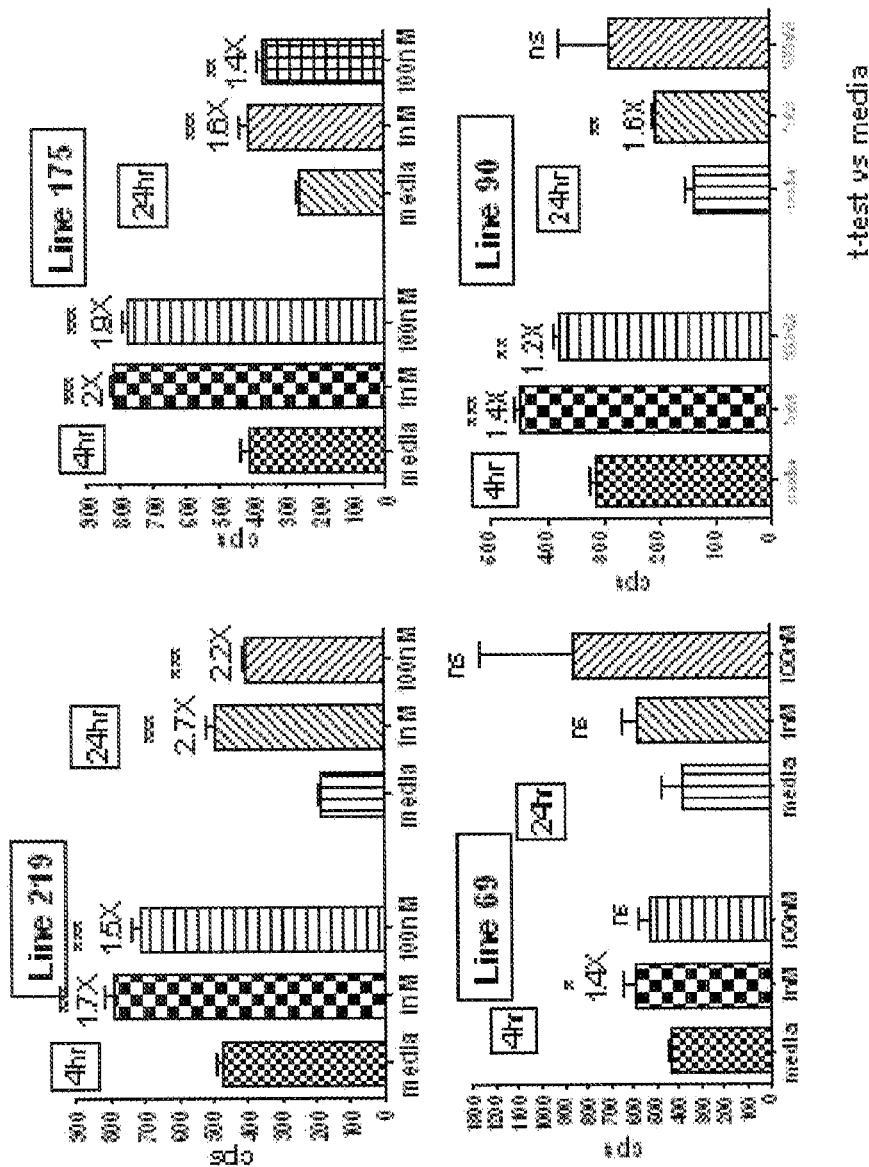
FIG. 12 shows the effects of prokineticin 2 (PROK2) peptide on luciferase expression in primary cortical neurons from different CreLuc lines. Primary cortical neurons were harvested from four different CreLuc lines at E18. The assays were run in triplicate at day three in culture with either 1 nM or 100 nM PROK2 peptide at two timepoints, 4 hours and 24 hours. BrightGlo was used for the assay and read on a TopCount. Data is shown as counts per second (cps)
Figure 16:
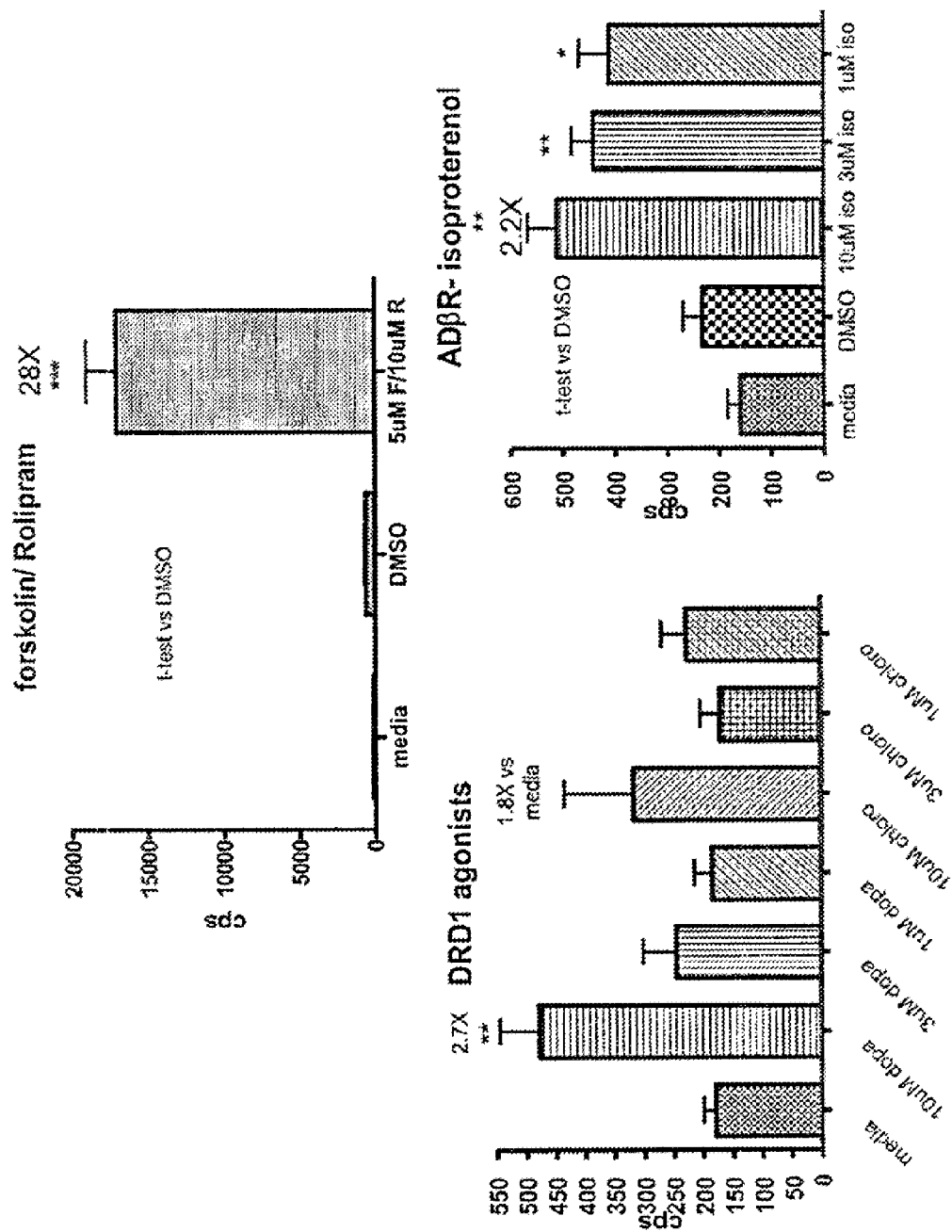
FIG. 16 shows induced luciferase expression in CreLuc striatal neurons by forskolin and rolipram, and Gs agonists DRD1 and ADβR. Striatum neurons were isolated from E14 embryos (line 187). The assays were run at day 4 in culture. Forskolin (F) was used at 5 $\mu$M, rolipram (R) at 10 $\mu$M. The Gs agonists isoproterenol (iso), dopamine (dopa) and SKF82958 (chloro) were used at 10 $\mu$M, 3 $\mu$M and 1 $\mu$M. The assay was read at 5 hours with a TopCount luminometer and Bright Glo luciferase reagent (Promega). Data is shown as counts per second (cps).
Figure 17:
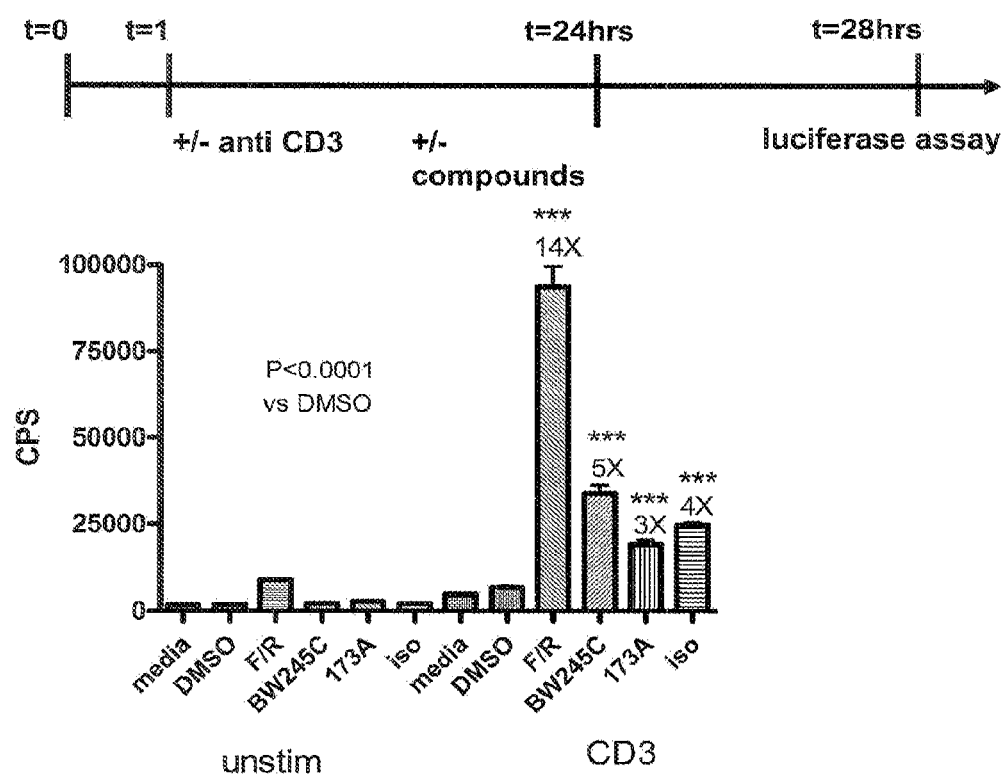
FIG. 17 shows the effects of general cAMP inducers such as forskolin (F) and rolipram (R), as well as Gs agonists on luciferase expression in whole splenocyte preps isolated from CreLuc mice. Line 64 splenocytes were stimulated for 24 hours with anti-CD3 antibody (CD), the other half were untreated (unstim). At 24 hours, compounds were added to the plates for an additional 4 hours. The co-treatment of forskolin and rolipram (F/R) was 5 uM forskolin and 10 um rolipram. The Gs agonists used are: EX00000173A (173A) as an EP2 agonist, BW245C as a DP1 agonist and isoproterenol as an ADβR agonist. All Gs agonists were used at 10 uM. The assay is run as triplicates. After 4 hours, 100 ul of BrightGlo was added and the assay was read on a TopCount luminometer. Data is shown as counts per second (cps).

Any cell culture derived from the CreLuc mice may be used to screen compounds for the ability to modulate GPCRs. Luciferase expression was induced in CreLuc striatal neurons by forskolin and rolipram, and Gs agonists for DRD1 and ADβR (FIG. 16). Striatum neurons were isolated from E14 embryos (line 187). The assays were run at day 4 in culture. Forskolin was used at 5 µM, rolipram at 10 µM. The Gs agonists (isoproterenol is an agonist at ADRβ, dopamine and SKF82958 are agonists at D1DR) were used at 10 µM, 3 µM and 1 µM. The assay was read at 5 hours with a TopCount luminometer and Bright Glo luciferase reagent (Promega). A highly significant increase of 28 fold is observed in cells treated with the forskolin and rolipram combination. Significant increases are also observed with 10 µM dopamine, 2.7 fold, and all 3 concentrations of isoproterenol. Thus, the transgene is functional in striatal as well cortical neurons (see FIG. 10).

3. Whole Splenocytes

Whole splenocyte preps isolated from CreLuc mice (line 64) were used to show the effects of general cAMP inducers such as forskolin and rolipram, as well as Gs agonists on luciferase expression (FIG. 16). Spleens were harvested from the animals in 1×HBSS (Invitrogen, Carlsbad, Calif., cat#14025). The cells were then isolated by mechanically disrupting the spleen capsule using the end of a 5 ml syringe in 5 mls of D-PBS (Invitrogen, Carlsbad, Calif., cat#14190). The cell suspension was then passed through a 70 um strainer into a 50 ml conical tube. The cells were then spun down at 800 rpm, then resuspended and incubated for 6 minutes at room temperature in 5 ml of 1× Pharm Lyse solution (BD BioSciences, cat#555899). Cells were then washed by adding 28 mls of media consisting of RPMI 1640 (Invitrogen, Carlsbad, Calif., cat#11875), 10% FCS (Invitrogen, Carlsbad, Calif., cat#16000), 1% pen/strep (Invitrogen, Carlsbad, Calif., cat#15070) and 0.1% β-mercaptoethanol (Invitrogen, Carlsbad, Calif., cat#21985). Cells were diluted to $2\times10^6$/ml, and 100 ul of the cells were plated per well in a 96 well white opaque plate. Half of the cells were stimulated for 24 hours with anti-CD3 antibody (BD Pharmingen, cat#553058), the other half were untreated. At 24 hours, compounds were added to the plates for an additional 4 hours. The general inducers include rolipram (Sigma R6520), forskolin (Sigma F6886). The Gs agonists used are: EX00000173A (173A; in house synthesized) is an agonist at the Gs coupled prostaglandin E2 (EP2) receptor; BW245C (Sigma B9305) is an agonist at the Gs coupled prostaglandin D2 receptor 1 (DP1) and isoproterenol (Sigma 15627) is an agonist at the Gs coupled β-adrenergic receptor (ADβR). The assay was run in triplicate. After 4 hours, 100 µl of BrightGlo (Promega, Madison, Wis., cat#E2610) and the assay was read on a TopCount luminometer. An increase of 14 fold versus DMSO is observed in CD3 stimulated cells in the presence of rolipram and forskolin. Statistically significant increases (by t-test) are also observed with all three of the Gs agonists versus the DMSO only control. This experiment shows that the transgene is functional in whole splenocyte populations. The preparation used in the experiment was a whole splenocyte preparation which is a mixed population of cells. Experiments described below look at luciferase expression levels in subpopulations such as T cells and B cells.

4. Isolated T Cells

Figure 18:
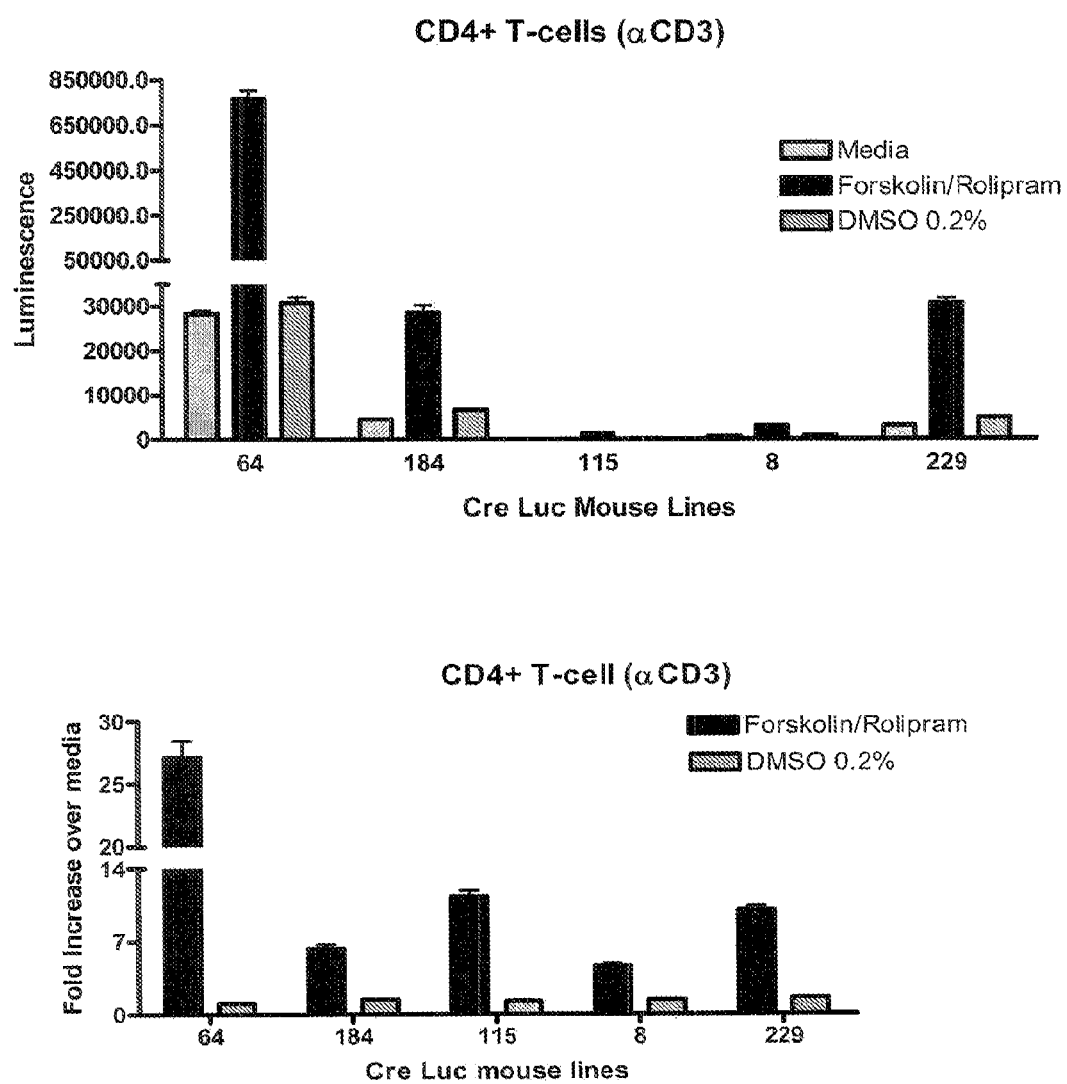
FIG. 18 shows the effects of general cAMP activation by rolipram and forskolin in T cells isolated from five different sublines of CreLuc mice. The cells were stimulated with anti CD3 antibodies (1 ug/ml). After 18 hours, 10 $\mu$M rolipram and 5 $\mu$M forskolin were added to the plates for an additional 4 hours. BrightGlo was added and the assay was read on the TopCount. Data is shown as luminescence (counts per second) in the top panel, and as fold increase over media only controls in the bottom panel.

The effects of general cAMP activation by rolipram and forskolin in T cells isolated from five different sublines of CreLuc mice was studied (FIG. 18). Whole splenocyte populations were prepared by mechanical disruption as described above. CD4+ cells were then isolated using MACS Magnetic Separation with Positive Selection Column (Miltenyi Biotec cat#130-049-201). The cells, $1.5\times10^5$ per well, were then plated on 96 well white opaque plates and then stimulated with anti CD3 antibodies (BD Pharmingen cat#553058). After 18 hours, 10 µM rolipram (Sigma R6520) and 5 µM forskolin (Sigma F6886) were added to the plates for an additional 4 hours. BrightGlo (Promega, Madison, Wis., cat#E2610) was added and the assay was read on the TopCount. Data is shown as luminescence (counts per second), and as fold increase over media only controls. Increases in expression of luciferase were observed in all lines tested with line 64 giving the highest levels of induction demonstrating that the cAMP pathway activated by general modulators in the CreLuc mice.

Figure 19:
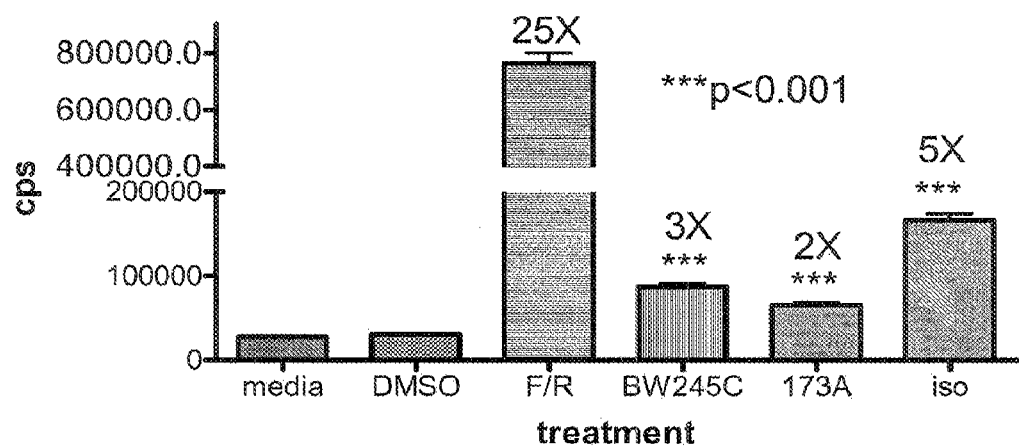
FIG. 19 shows the effects of Gs agonists on luciferase levels in anti CD3 stimulated CD4+ T cells isolated from CreLuc mice (line 64). The cells, $1.5 \times 10^5$ per well, were plated on 96 well white opaque plates and then stimulated with anti CD3 antibodies (1 ug/ml). After 24 hours, compounds were added for an additional 4 hours. Gs agonists BW245C, EX00000173A (1734A) and isoproterenol (iso) were all used at 10 $\mu$M. Forskolin (F) was added at 5 uM and rolipram (R) at 10 uM. BrightGlo was added and the assay was read on the TopCount. Data is shown as counts per second (cps).

The effects of different Gs agonists on luciferase levels in anti CD3 stimulated CD4+ T cells isolated from CreLuc mice (line 64) was studied (FIG. 19). Whole splenocyte populations were prepared by mechanical disruption. CD4+ cells were then isolated by MACS Magnetic Separation with Positive Selection (Miltenyi Biotec cat#130-049-201). The cells, $1.5 \times 10^5$ per well, were then plated on 96 well white opaque plates and then stimulated with anti CD3 antibodies (BD Pharmingen cat#553058). After 24 hours, compounds were added for an additional 4 hours. Gs agonists for DP (BW245C), EP2 (EX00000173A) and ADβR (isoproterenol) were all used at 10 µM. Forskolin 5 µM, and rolipram 10 µM. BrightGlo (Promega, Madison, Wis., cat#E2610) was added and the assay was read on the TopCount. A 25-fold increase is observed in cells treated with forskolin and rolipram. Highly significant increases are observed with all three Gs agonists, 3-fold for BW245C, 2-fold for 173A, and 5 fold for isoproterenol. The transgene was responsive to specific Gs agonists as well as general modulators of the cAMP pathway.

5. Isolated B Cells

Figure 20:
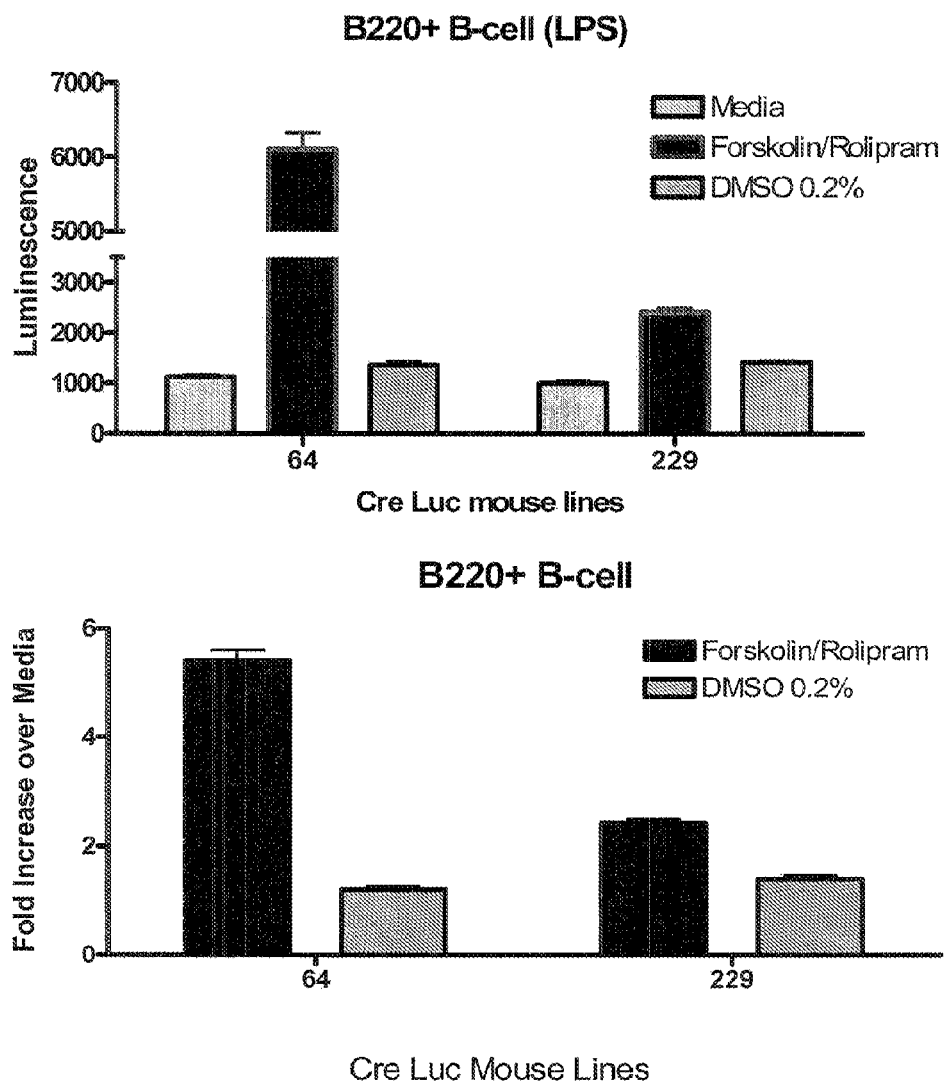
FIG. 20 shows the effects of general cAMP activation by rolipram and forskolin in B cells isolated from two different sublines of CreLuc mice. Cells were plated $2.0 \times 10^5$ per well on 96 well white opaque plates and stimulated with 10 ng/ml lipopolysaccaride (LPS). After 18 hours, 10 $\mu$M rolipram and 5 $\mu$M forskolin were added to the plates for an additional 4 hours. BrightGlo was added and the assay was read on the TopCount. Data is shown as luminescence (counts per second), and as fold increase over media only controls.
Figure 21:
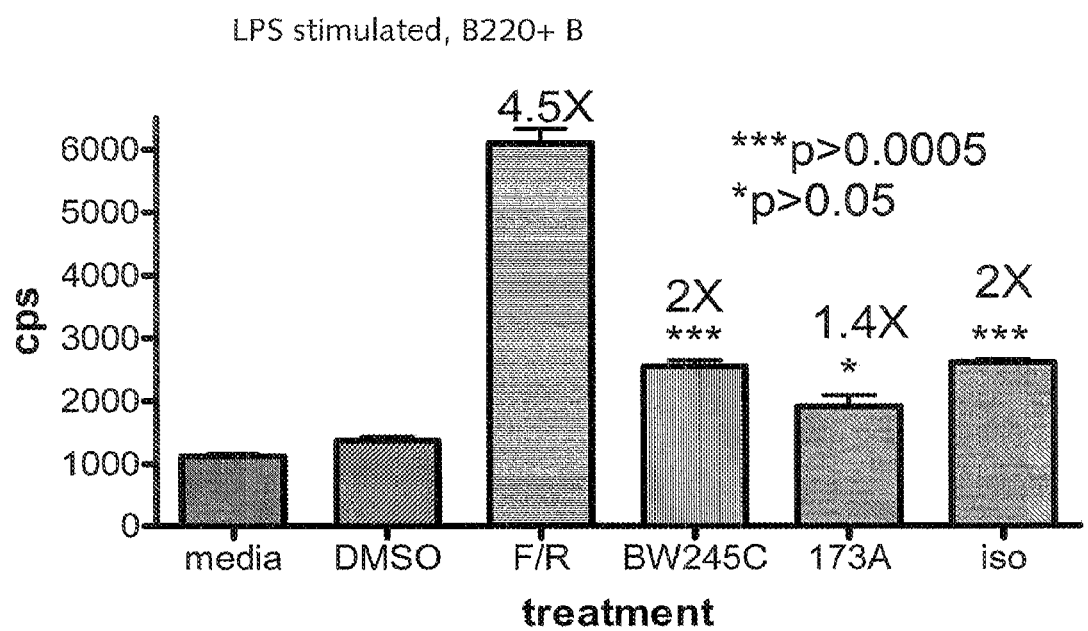
FIG. 21 shows the effects of Gs agonists on luciferase levels in LPS stimulated B220+ B cells isolated from CreLuc mice. The cells were plated, 2.0×10$^5$ per well on 96 well white opaque plates and then stimulated with 10 ng/ml lipopolysaccaride (LPS). After 24 hours, compounds were added for an additional 4 hours. Gs agonists BW245C, EX00000173A (1734A) and isoproterenol (iso) were all used at 10 µM. Forskolin (F) was added at 5 uM and rolipram (R) at 10 uM. BrightGlo (Promega, Madison, Wis., cat#E2610) was added and the assay was read on the TopCount. Data is shown as counts per second (cps).

The effects of general cAMP activation by rolipram and forskolin in B cells isolated from two different sublines of CreLuc mice was examined (FIG. 20). Whole splenocyte populations were prepared by mechanical disruption as described above. B220+ cells were then isolated using MACS Magnetic Separation with Positive Selection Column (Miltenyi Biotec, cat#130-049-501). The cells were then plated, $2.0 \times 10^5$ per well on 96 well white opaque plates and then stimulated with 10 ng/ml lipopolysaccaride (LPS) (Sigma L-2630). After 18 hours, 10 µM rolipram (Sigma R6520) and 5 µM forskolin (Sigma F6886) were added to the plates for an additional 4 hours. BrightGlo (Promega, Madison, Wis., cat#E2610) was added and the assay was read on the TopCount. Data is shown as luminescence (counts per second), and as fold increase over media only controls. Increases in luciferase expression are observed in line 64 but not line 229.

6. Microglia

Figure 22:
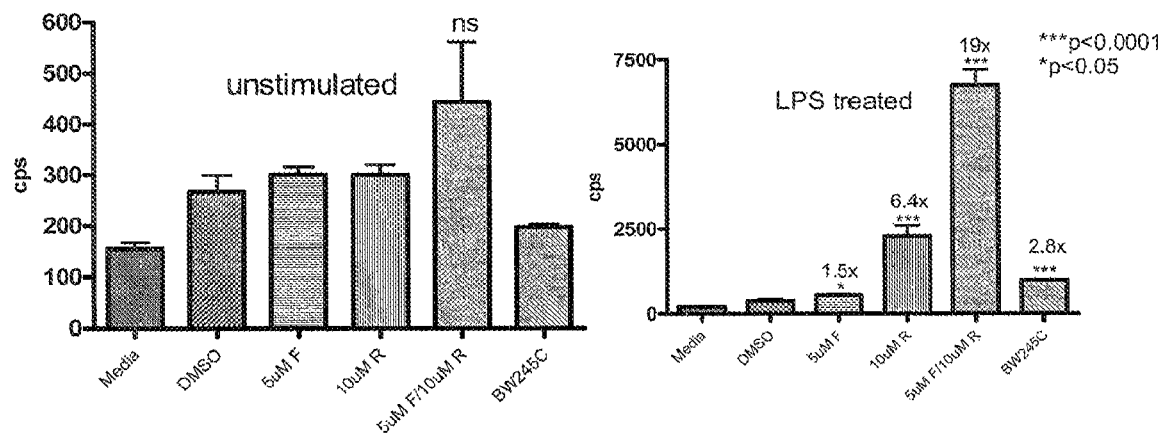
FIG. 22 shows the Induced luciferase expression in isolated microglia (line 64) by the general cAMP activators, forskolin (F) and rolipram (R), and an agonist for the DP receptor, BW245C. Primary microglia were isolated from the cortices from P2 mice and plated in 96 well format on Poly-D-Lysine-coated plates. Cells were either left untreated or stimulated for 2 hours with 100 ng/ml LPS. Compounds were then added for an additional 4 hours before the Bright Glo assay was run. The compounds used were 5 µM forskolin, 10 µM rolipram or the combination of the two, or the Gs agonist for the DP1 receptor, BW245C at 10 µM. Data is shown as counts per second (cps).

Induction of luciferase expression in microglia isolated from CreLuc mice by the general cAMP activators, forskolin and rolipram, and an agonist for the DP receptor, BW245C was examined (FIG. 22). Primary microglia were isolated from the cortices from P2 mice (line 64) in media consisting of DMEM (GIBCO Cat#11995), 10% FBS (GIBCO Cat#16140) and 1% Penicillin-Streptomycin 100× (GIBCO Cat#15140). The cells were plated in 96 well format on Poly-D-Lysine-coated plates. Cells were either left untreated or stimulated for 2 hours with 100 ng/ml LPS. Compounds were then added for an additional 4 hours before the Bright Glo assay was run. The compounds used were 5 µM forskolin, 10 µM rolipram or the combination of the two, or the Gs agonist for the DP1 receptor, BW245C at 10 µM. In unstimulated conditions, microglia are unresponsive to general cAMP modulators and the specific Gs agonist for the DP receptor. However, when microglia were stimulated with LPS, the cells became responsive to forskolin and BW245C.

7. Mouse Embryonic Fibroblasts

Figure 33:
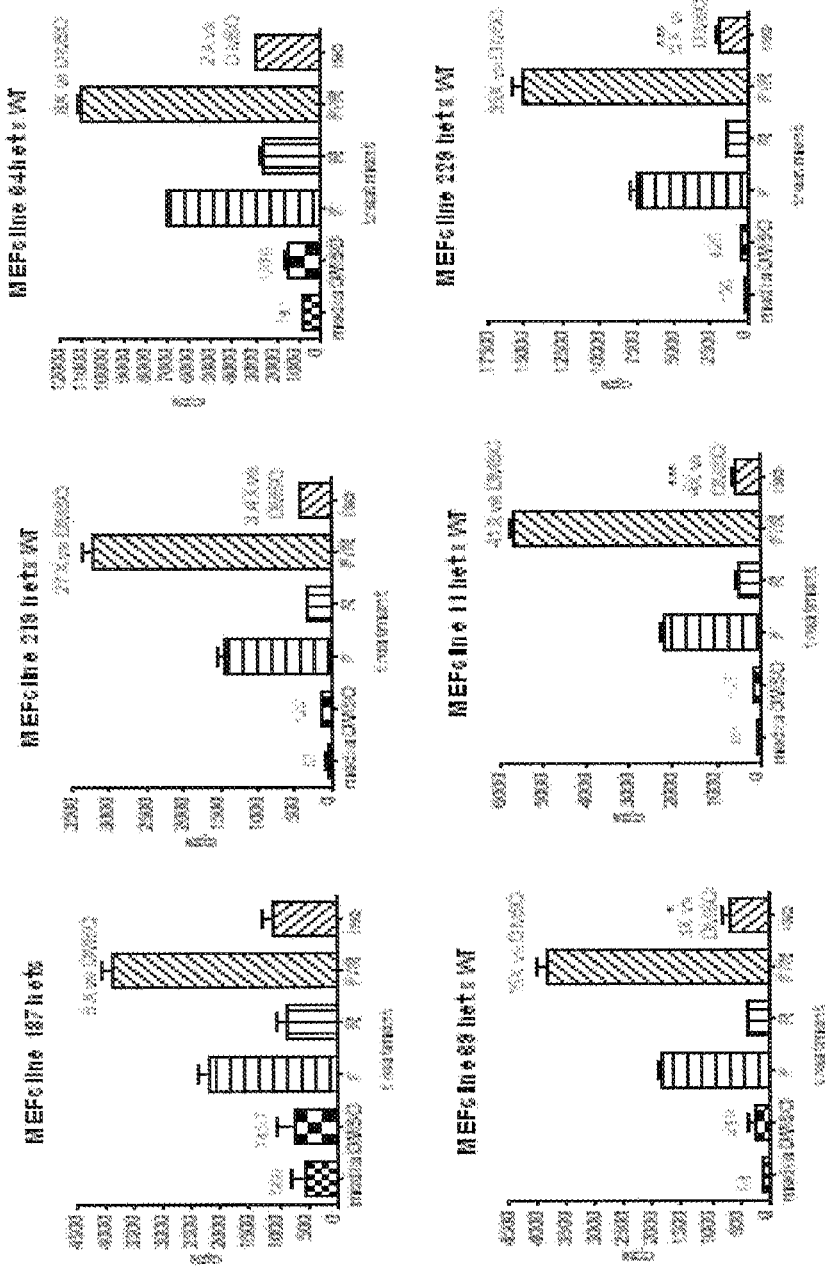
FIG. 33 shows the effects of forskolin, rolipram and isoproterenol on luciferase expression in mouse embryonic fibroblasts. Mouse embryonic fibroblasts were cultured from E12 embryos from six independent CreLuc lines and plated at 20,000 cells per well. Compounds tested include 10 µM forskolin (F), 5 µM rolipram (R) and 10 µM isoproterenol (iso). Data is shown as counts per second (cps).

The effects of forskolin, rolipram and isoproterenol on luciferase expression in mouse embryonic fibroblasts was investigated (FIG. 33). Mouse embryonic fibroblasts were cultured from E12 embryos from six independent CreLuc lines. Cells were plated at 20,000 cells per well. Compounds tested include 10 µM forskolin, 5 µM rolipram and 10 µM isoproterenol (ADβR agonist). Significant increases were observed in all lines in response to the combination of forskolin and rolipram. Significant increases were also observed in three of the lines in response to isoproterenol.

7. Cardiomyocytes

Figure 35:
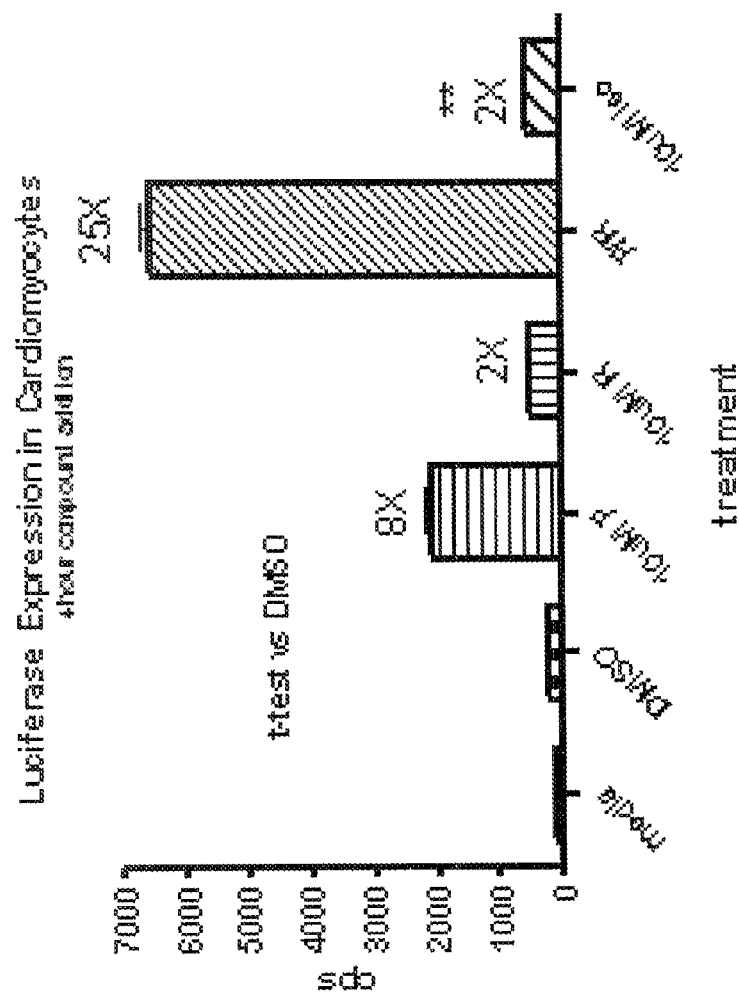
FIG. 35 shows the effects of forskolin and rolipram and isoproterenol on luciferase levels in cardiomyocytes. Cardiomyocytes were isolated from P3 pups (line 229). The cells were cultured in a 96 well plate. Compounds tested include 10 µM forskolin (F), 5 µM rolipram (R) and 10 µM isoproterenol (iso). Data is shown as counts per second (cps).

The effects of forskolin and rolipram and isoproterenol on luciferase levels in cardiomyocytes was studied (FIG. 35). Cardiomyocytes were isolated from P3 pups from line 229. The cells were cultured in a 96 well plate. Compounds tested include 10 µM forskolin, 5 µM rolipram and 10 µM isoproterenol (ADβR agonist). Significant increase in luciferase levels were observed with the combination of rolipram and forskolin (25 fold) and a significant increase was also observed with the agonist isoproterenol (2 fold).

B. In Vivo and Ex Vivo Experiments

1. Effects of General cAMP Modulators

Figure 23:
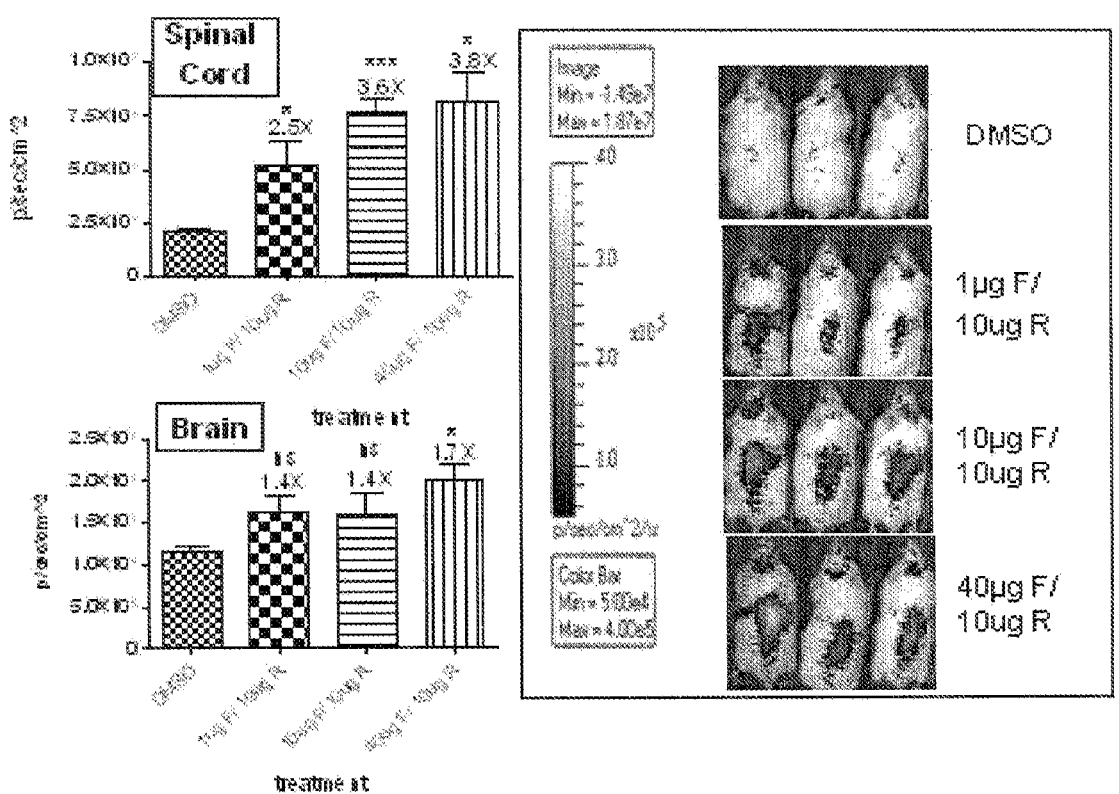
FIG. 23 shows the effects of intrathecally injected forskolin (F) and rolipram (R) on the induction of luciferase expression in the brain and spinal cord of CreLuc mice (line 187). N=3-4 mice per group, 3 month old males. Group A: DMSO control, Group B: 1 ug forskolin/bug rolipram, Group C: bug forskolin/10 ug rolipram, Group D: 40 ug forskolin/bug rolipram. The animals were dosed via intrathecal injection, lumbar region, and volume of 5 µl per mouse. They were imaged at 4 hours post dosing. The data for both spinal cord and brain is shown as the average peak radiance, photons per second per cm2.

The effects of intrathecally injected forskolin and rolipram on the induction of luciferase expression was studied in the brain and spinal cord of line 187 CreLuc mice (FIG. 23). The line of mice chosen was previously determined to have expression of the transgene in both brain and spinal cord (data not shown). The line of mice selected for this assay (line187) has inducible levels of luciferase in both the brain and spinal cord. N=3-4 mice per group, four treatment groups, 3 month old males. Group A: DMSO control, Group B: 1 µg forskolin/10 µg rolipram, Group C: 10 µg forskolin/10 µg rolipram, Group D: 40 µg forskolin/10 µg rolipram. The animals were dosed via intrathecal injection, lumbar region, and volume of 5 µl per mouse. They were imaged at 4 hours post dosing. The data for both spinal cord and brain is shown as the average peak radiance, photons per second per cm2. Statistically significant increase is observed in the spinal cord, a significant increase in luciferase signal in brain is only seen in the highest concentration of forskolin. When general modulators or cAMP are injected into the spinal cord, there is a localized increased expression of the transgene in the spinal cord with a lower response observed in the brain.

2. Effects of Gs Agonists

The effects of the EP2 agonist, EX00000173A on luciferase expression in the brain and spinal cord of CreLuc mice was studied (FIG. 24). Male mice, 5 months old, from line 187, n=5, were injected i.p. with either vehicle (5% DMSO, 0.05% tween 80, PBS) or 10 mg/kg EX00000173A (in house synthesis). Animals were bioimaged at 4 hours post doing. Data shown is the average of the 5 mice for both brain and spinal cord, as photons per second per cm2. Statistically significant increases are seen with agonist treatment in both the brain and spinal cord. Thus, a Gs agonist administered i.p. activated the transgene.

Figure 25:
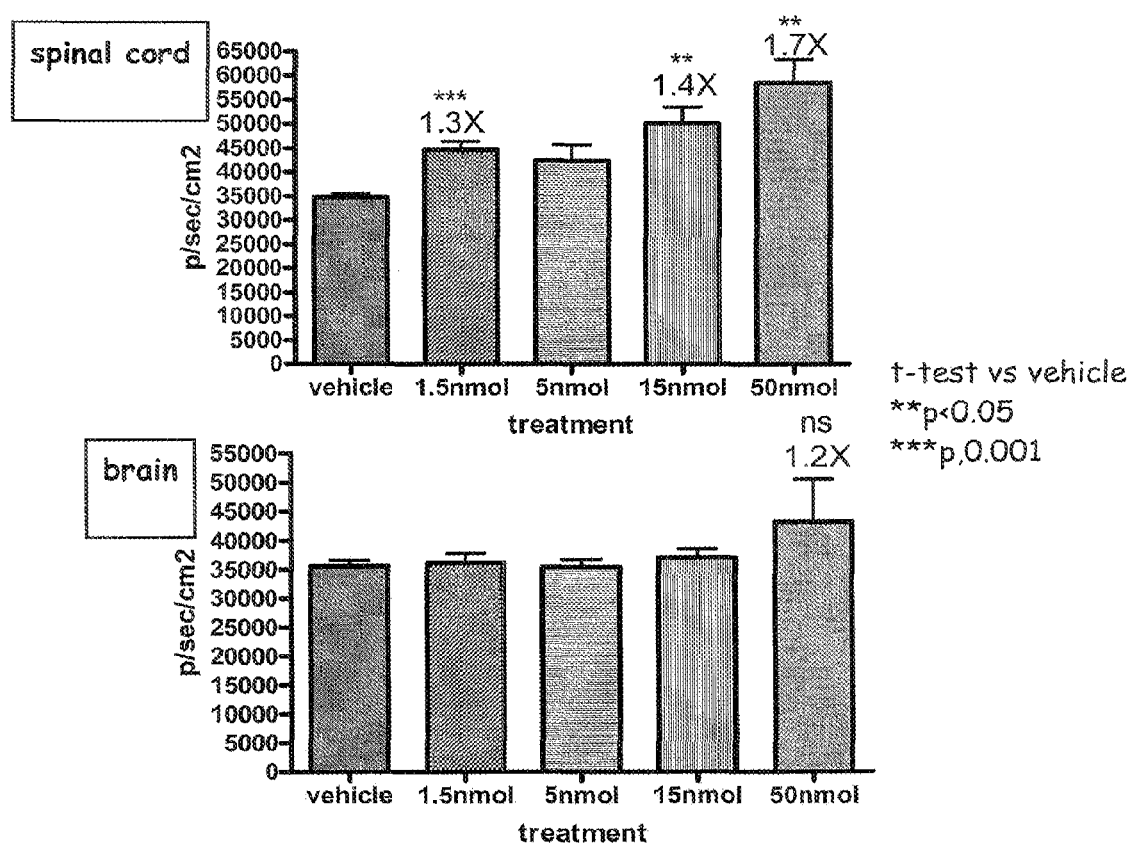
FIG. 25 shows the effects of the EP2 agonist, EX00000173A on luciferase expression in CreLuc mice. Mice were dosed with either vehicle control or varying doses of the EP2 agonist EX0000173A. Mice were dosed by intrathecal injection (5 µl per mouse) and were bioimaged 4 hours later on the IVIS bioimager. Data is shown as the mean of the five mice, average peak radiance, photons per second per cm$^2$.

Further, the effects of the EP2 agonist, EX00000173A on luciferase expression in CreLuc mice was dose-responsive (FIG. 25). Line 187 was selected because this line has high inducible expression in both brain and spinal cord. The assay consists of five groups of six week old mice, with an n=5. Mice were dosed with either vehicle control (D-PBS; Dulbeccos phosphate buffered saline, Invitrogen, cat#14040) or varying doses of the EP2 agonist EX0000173A (in house synthesis) 1.5 nmol, 5 nmol, 15 nmol and 50 nmol. Mice were dosed by intrathecal injection (5 µl per mouse) and were bioimaged 4 hours later on the IVIS bioimager. Data for both the brain and spinal cord is shown as the mean of the five mice, average peak radiance, photons per second per cm$^2$. Statistically significant (t-test) increases with agonist treatment are observed at three concentrations in the spinal cord, but not in the brain. An increase (not significant) in the brain is only observed at the highest concentration as expected with an intrathecal injection.

Figure 27A:
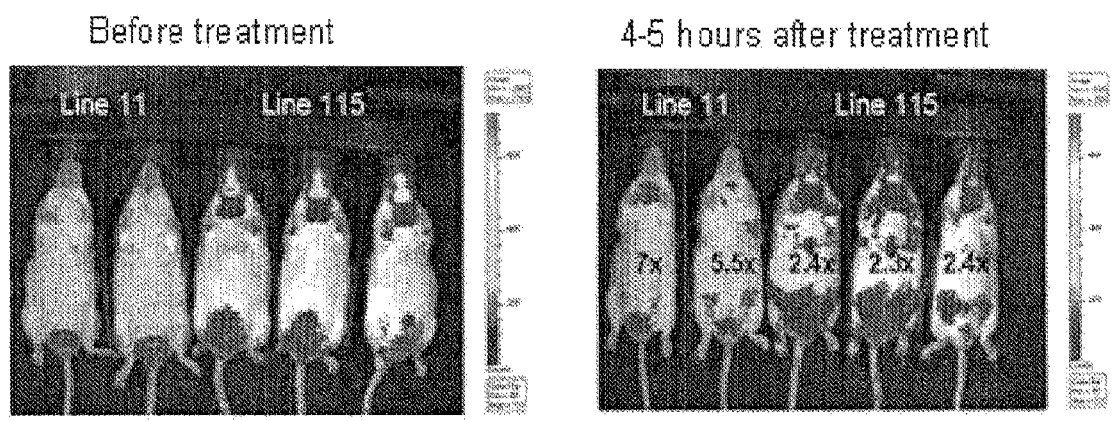
FIG. 27A shows induction of luciferase by the Adrb3 agonist CL316,243 (1 mg/kg, ip) in lines 11 (n=2) and 115 (n=3) of CRE-Luc mice. BLIs were taken before and 4-5 hours after treatment. Luciferase activities in tissue homogenates is shown below the pictures.
Figure 27B:
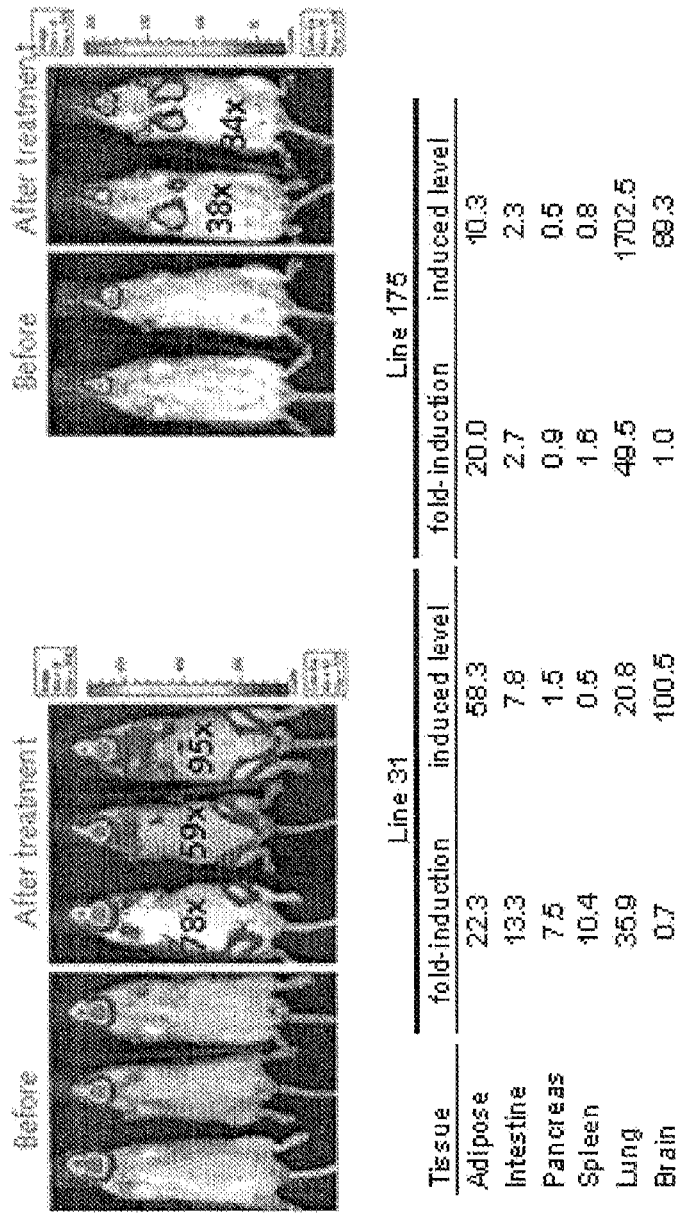
FIG. 27B shows induction of luciferase by the Adrb3 agonist CL316,243 (1 mg/kg, ip) in lines 31 (n=2) and 175 (n=3) of CRE-Luc mice. BLIs were taken before and 4-5 hours after treatment. Luciferase activities in tissue homogenates is shown below the pictures.

FIG. 26 shows induction of luciferase in different tissues by the adrenoceptor beta3 (Adrb3) agonist, CL316,243 (1 mg/kg, ip) in CRE-Luc mice. The luciferase assay was performed in tissue homogenates. Among 12 independent transgenic lines screened, 7 lines showed greater than 10 fold of induction in the adipose tissue and lung. 4 lines showed visible induction via bioimaging (see FIGS. 27A and 27B).

3. Specific Effects of the Gs Agonist AVE0010

Figure 28:
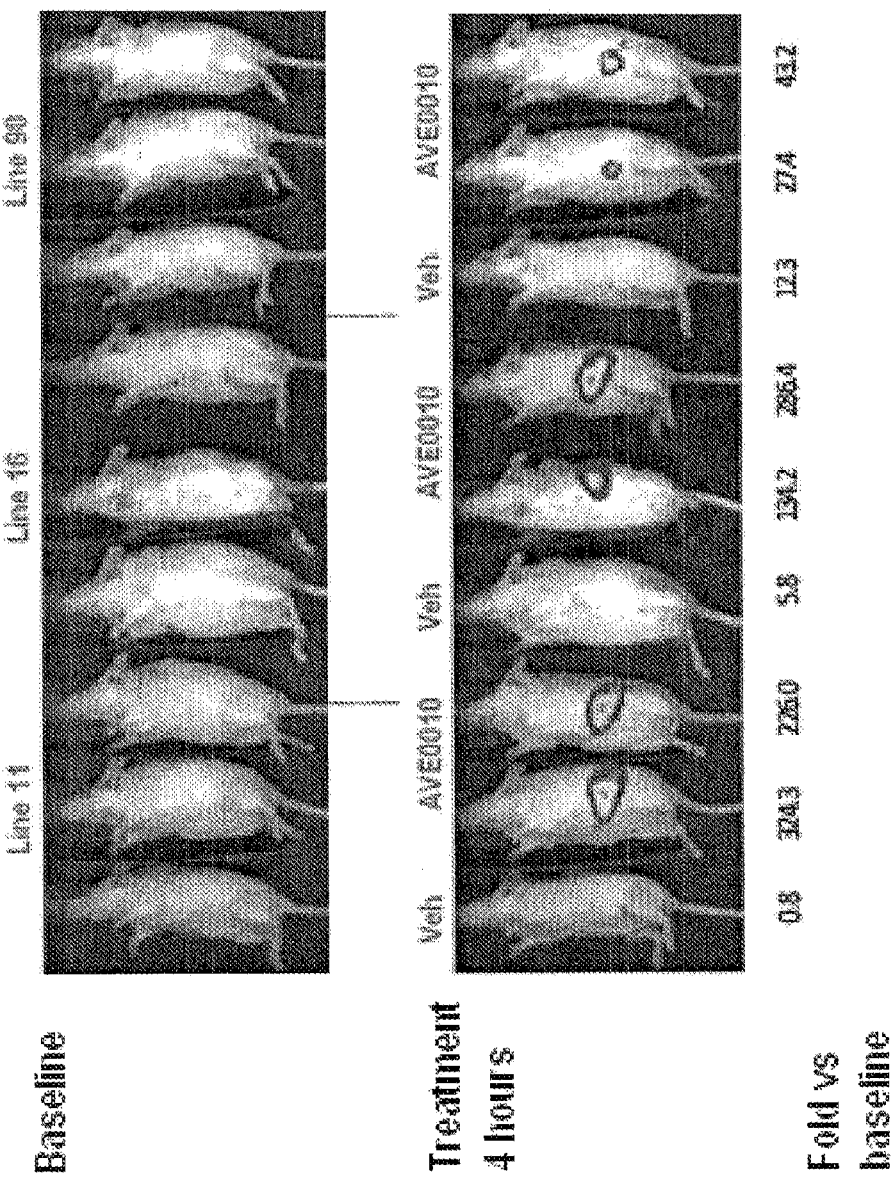
FIG. 28 shows induction of luciferase reporter by the glucagon-like peptide 1 receptor (GLP-1R) agonist, AVE0010, in three independent lines of CRE-Luc mice. Baseline images were acquired on day 1. On day 2, mice were treated with AVE0010 (0.1 mg/kg, sc) and imaged after 4 hours. Fold induction over baseline at indicated at the bottom.
Figure 29:
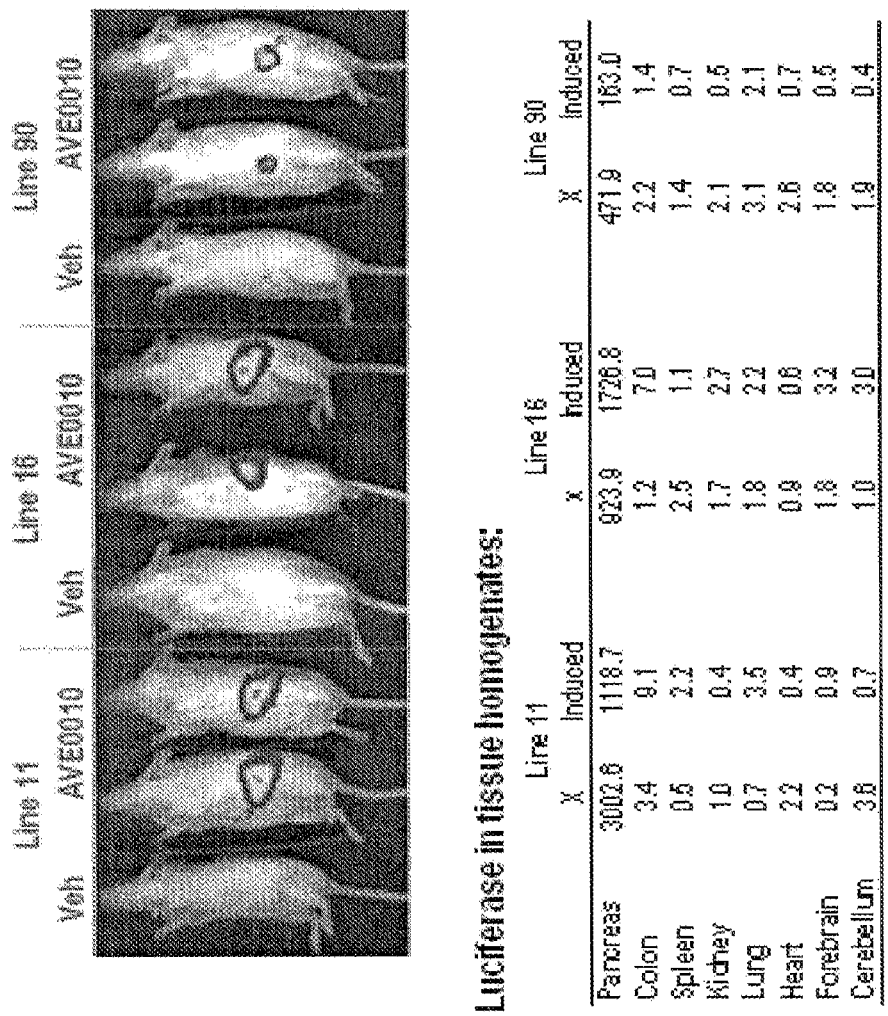
FIG. 29 shows induction of luciferase reporter by the glucagon-like peptide 1 receptor (GLP-1R) agonist, AVE0010, in three independent lines of CRE-Luc mice. Mice were treated with AVE0010 (0.1 mg/kg, sc) for 4 hours. Luciferase activities in 8 different tissues were measured.

Transgene activation co-localizes with tissue specific receptor activation as exemplified by the induction of luciferase reporter by the glucagon-like peptide 1 receptor (GLP-1R) agonist, AVE0010, which was studied in three independent lines of CRE-Luc mice (FIG. 28). The GLP-1R is Gs coupled. Baseline images were acquired on day 1. On day 2, mice were treated with AVE0010 (0.1 mg/kg, sc) and imaged after 4 hours. Folds of induction over baseline were indicated at the bottom. As expected since the GLP-1R receptor is mainly expressed in pancreatic tissue, there was a strong induction of transgene activation observed in the pancreas. Luciferase activities in 8 different tissues were measured for lines 11, 16 and 90 (FIG. 29) following treatment with AVE0010 (0.1 mg/kg, s.c.) for 4 hours. The luciferase activity in tissue homogenates confirmed the pancreas-specific induction of luciferase. The activity of AVE0010 is limited to the pancreas even though GLP-1R is found in different tissue types.

Figure 30:
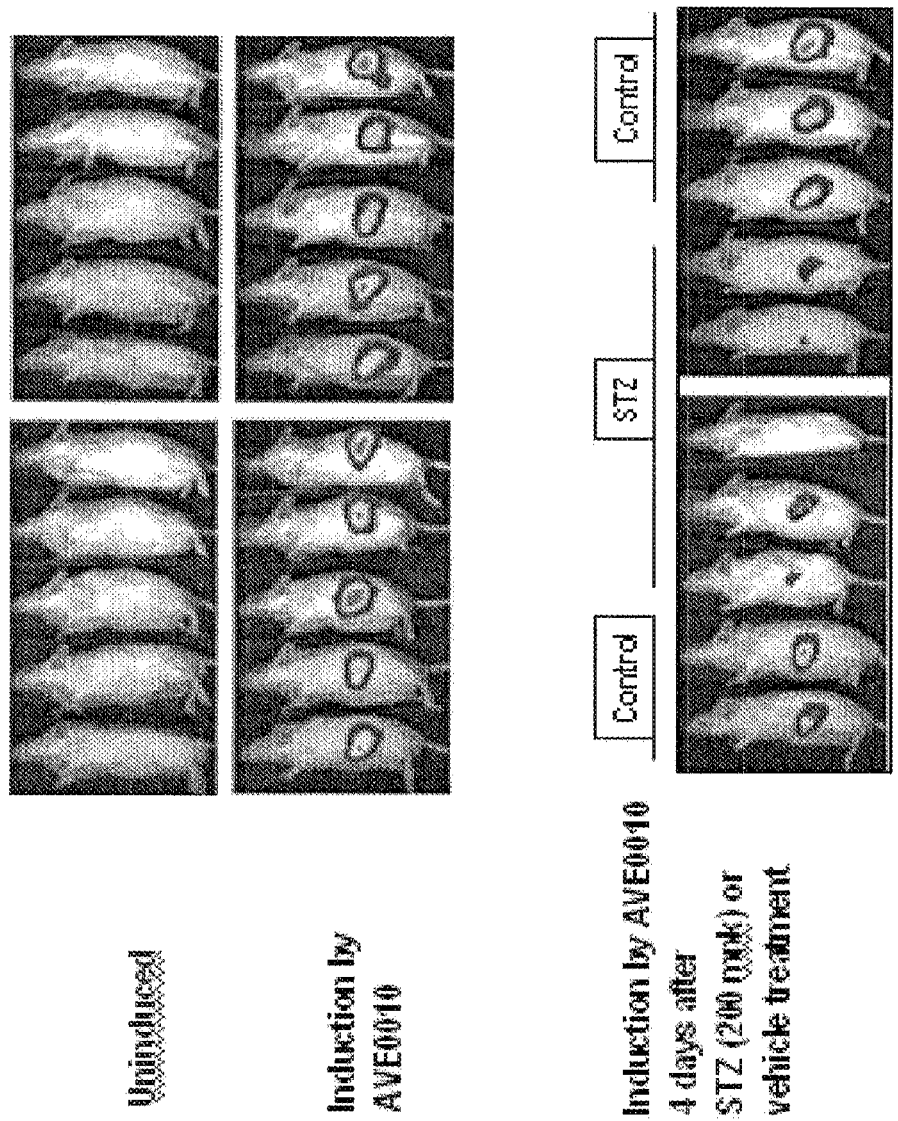
FIG. 30 shows the effects of the beta-cell toxin streptozotocin (STZ) on the induction of CRE-Luc by AVE0010. Male CRE-luc mice (line 11) were imaged before ("uninduced"; top panel) and after AVE0010 was given at 0.1 mg/kg, sc ("induction by AVE0010", middle panel). All mice were responsive to AVE0010 (middle panel). Then, the animals were treated with vehicle (control) or STZ (200 mpk, ip). Four days later, they were imaged again after AVE0010 treatment (bottom panel).

The induction of Cre-Luc by AVE0010 is likely beta-cell mediated. The effects of the beta-cell toxin streptozotocin (STZ) on the induction of CRE-Luc by AVE0010 was investigated (FIG. 30). Male CRE-luc mice (line 11) were imaged before and after AVE0010 (0.1 mg/kg, sc) treatment. The data indicated that all mice were responsive to AVE0010 (see middle panel of FIG. 30). Then, the animals were treated with vehicle or STZ (200 mpk, ip). Four days later, they were imaged again after AVE0010 treatment. Compared to vehicle group, the STZ group had decreased luciferase induction.

Figure 31:
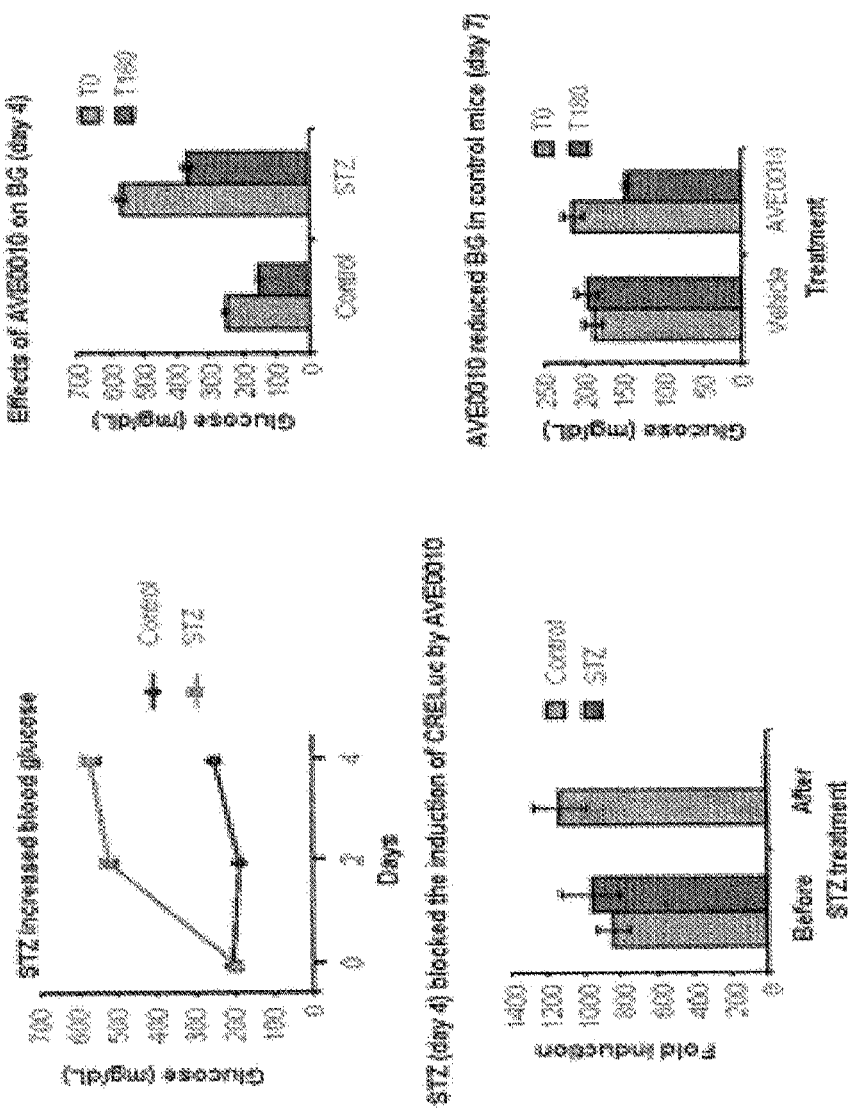
FIG. 31 shows that the induction of CRE-Luc by AVE0010 is likely beta-cell-specific. Animals were treated as described in FIG. 30. Blood glucose levels were measured by tail vein nicking on unfasted mice. Glucose levels were read on a Bayer glucometer. Glucose levels are shown as mg glucose/ml. Fold induction is the luciferase bioimaging levels of AVE10 dosing versus the baseline signals. Blood glucose levels (BG) were increased by STZ (upper left panel). Non-fasting BG levels were reduced by AVE0010 (0.1 mg/kg, sc). BLI data shown in FIG. 30 were quantified.

The induction of CRE-Luc by AVE0010 is likely beta-cell-specific (FIG. 31). Animals were treated as described in FIG. 30. Blood glucose levels were measured by tail vein nicking on unfasted mice. Glucose levels were read on a Bayer glucometer. Glucose levels are shown as mg glucose/ml. Fold induction is the luciferase bioimaging levels of AVE10 dosing versus the baseline signals. Blood glucose levels (BG) were increased by STZ (upper left panel). Non-fasting BG levels were reduced by AVE0010 (0.1 mg/kg, sc). BLI data shown in FIG. 30 were quantified.

4. Bone Marrow Engraftments

Figure 32:
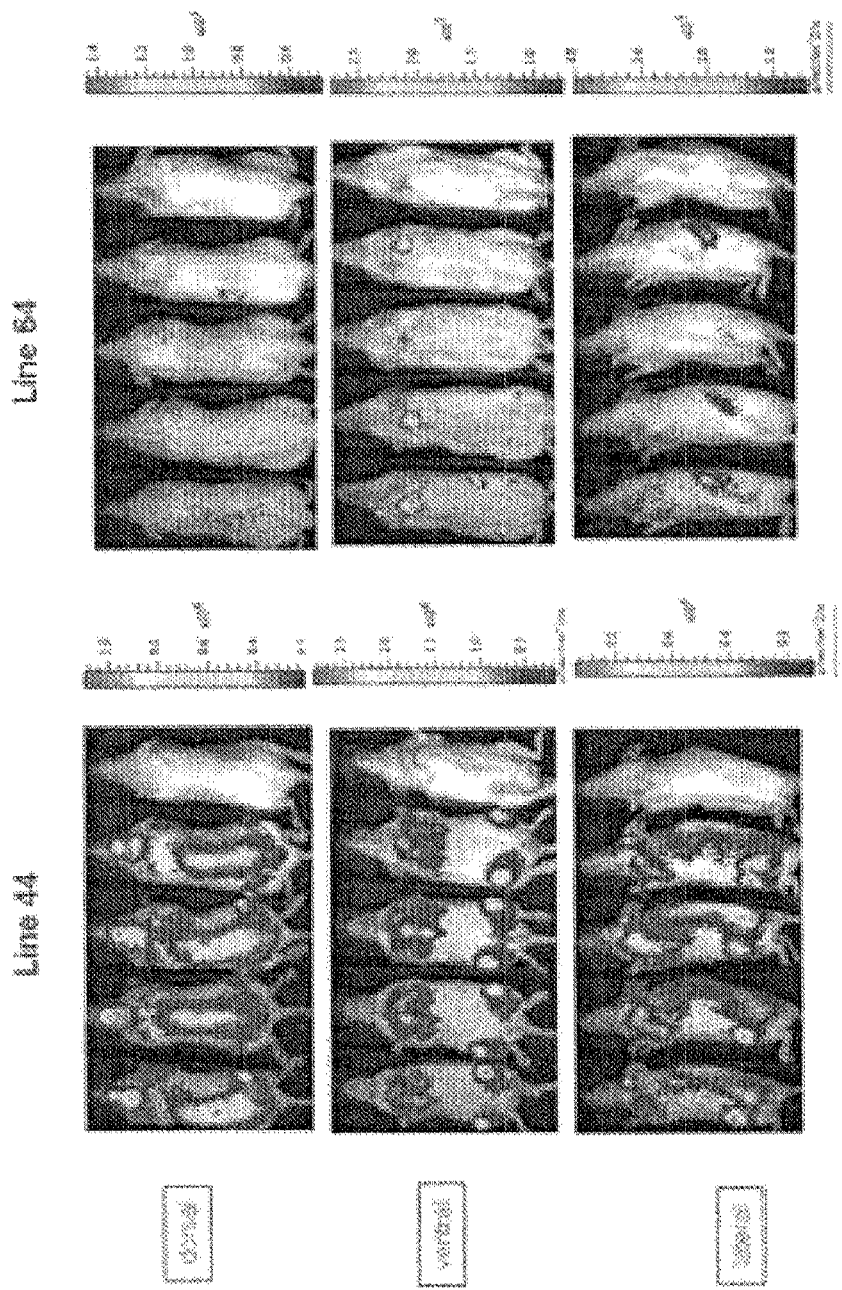
FIG. 32 shows CreLuc bone marrow engraftments into NOD scid gamma (NSG) mice. Bone marrow cells were harvested from lines 44 heterozygotes and line 64 homozygotes. The cells were then engrafted via tail vein injections of cells into irradiated NSG mice at 1 million or 5 million cells per mouse. For line 44: mouse 1 and 2 received 5 million cells, mouse 3 and 4 received 1 million cells; for line 64: mouse 1 received 5 million cells, mouse 2, 3, and 4 received 1 million cells. (4 NSG mice per CreLuc line). The animals were bioimaged at 4 weeks (data not shown) and then again at 8 weeks (data shown). Prior to imaging, the line 64 mice were induced for 5 hours with 5 mg/kg forskolin and 10 mg/kg rolipram.

CreLuc bone marrow engraftments were performed using NOD scid gamma (NSG) mice (FIG. 32). NSD mice are immunocompromised mice lacking mature T and B cells, functional natural killer cells and are deficient in cytokine signaling allowing for engraftment of hematopoietic cells. Bone marrow cells were harvested from lines 44 heterozygotes (having high basal luciferase levels; data not shown) and line 64 homozygotes (having inducible luciferase levels). The cells were then engrafted via tail vein injections of cells into irradiated NSG mice at 1 million or 5 million. For line 44, mouse 1 and 2 received 5 million cells while mouse 3 and 4 received 1 million cells. For line 64, mouse 1 received 5 million cells, mouse 2, 3, and 4 received 1 million cells per mouse. (4 NSG mice per CreLuc line). The animals were bioimaged at 4 weeks (data not shown) and then again at 8 weeks. Prior to imaging, the line 64 mice were induced for 5 hours with 5 mg/kg forskolin and 10 mg/kg rolipram. Bioimaging pictures are shown for the 8 week timepoint. The luciferase levels in the NSG mice engrafted with line 44 bone marrow cells mimics the image seen with the CreLuc line 44 (data not shown), with expression observed in the joints, spinal cord, head, and breastbone. Inducible luciferase expression is observed in the spleens of the NSG mice engrafted with line 64 bone marrow cells.

4. Animal Models

Figure 34:
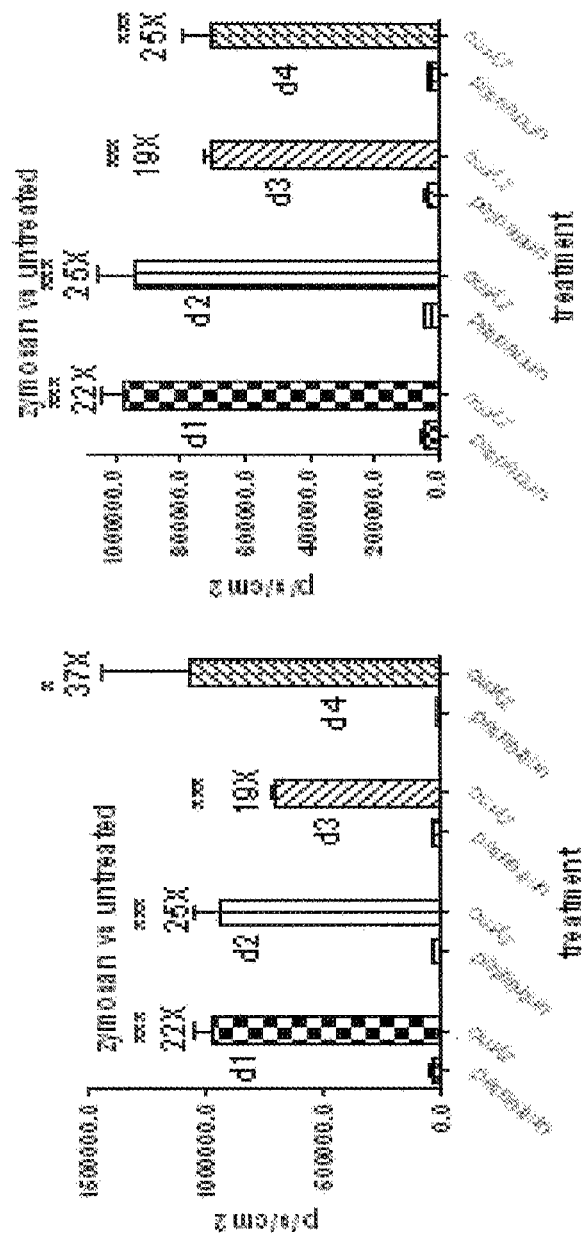
FIG. 34 show the effects of zymosan treatment on luciferase levels in CreLuc mice (line 187). Animals in the treated group were injected s.c in both rear paws with zymosan (zymo) to induce a pain response. The animals were then bioimaged daily for 4 days (denoted as d1, d2, d3 and d4).

The CreLuc mice can be used to study animal models of disease or aspects of disease states. Furthermore, the CreLuc mice can be used to screen for compounds that are able to modulate the disease or aspects of the disease that was induced in the CreLuc mice. For example, the effects of zymosan treatment on luciferase levels in CreLuc line 187 was studied (FIG. 34). CreLuc mice (line 187) in the treated group were injected s.c in both rear paws with zymosan to induce a pain response. The animals were then bioimaged daily for 4 days. Statistically significant Increases in luciferase expression are observed in the paws of the animals, in response to zymosan at all time points. Zymosan is a yeast cell wall component that strongly activates an inflammatory response. Thus, the CreLuc mice are a tool in which the inflammatory response can be monitored over time in the same animal. Also, the zymosan treated animals can be used a screening tool to assess the abilities of test compounds to reverse or exacerbate the inflammatory induced by zymosan.

The invention claimed is:

1. A transgenic non-human animal having a genome comprising:
   a transgene construct comprising, in the 5' to 3' direction, a first insulator element, a response element, a promoter, a bioluminescent reporter, a human growth hormone (hGH) functional element, and a second insulator element, wherein the first insulator element and the second insulator element are different, and
   wherein the response element is a cyclin AMP response element (CRE) comprising the nucleic acid sequence of either SEQ ID NO: 6 or 11.

2. The transgenic non-human animal of claim 1, wherein the first insulator element is selected from the group consisting of a matrix attachment region (MAR), a DNase I-hypersensitive site (HS4), and an inverted terminal repeat (ITR).

3. The transgenic non-human animal of claim 1, wherein the second insulator element is selected from the group consisting of a matrix attachment region (MAR), a DNase I-hypersensitive site (HS4), and an inverted terminal repeat (ITR).

4. The transgenic non-human animal of claim 1, wherein the promoter is a herpes simplex virus thymidine kinase minimal promoter (HSV TK min).

5. The transgenic non-human animal of claim 1, wherein the bioluminescent reporter is selected from the group consisting of luciferase, chloramphenicol acetyltransferase (CAT), beta-galactosidase, secreted alkaline phosphatase (SEAP), human growth hormone (HGH), and green fluorescent protein (GFP).

6. The transgenic non-human animal of claim 1, wherein the transgene construct comprises the nucleic acid sequence of SEQ ID NO: 18.

7. The transgenic non-human animal of claim 1, wherein the transgene construct comprises the nucleic acid sequence of SEQ ID NO: 19.

8. A cell isolated from the transgenic non-human animal of claim 1.

9. A tissue slice isolated from the transgenic non-human animal of claim 1.

10. A transgenic non-human animal having a genome comprising:
   a transgene construct comprising, in the 5' to 3' direction, a first insulator element, a response element, a promoter, a bioluminescent reporter, a human growth hormone (hGH) functional element, and a second insulator element,
   wherein the first insulator element is a matrix attachment region (MAR), the response element is a cAMP response element (CRE) that is repeated six times, the promoter is a herpes simplex virus thymidine kinase minimal promoter (HSV TK min), the bioluminescent reporter is luciferase, the human growth hormone (hGH) functional element is a hGH gene with a poly A tail, and the second insulator element is a matrix attachment region (MAR) that is different from the first insulator element.

11. The transgenic non-human animal of claim 10, wherein the response element is a cyclic AMP response element (CRE) comprising the nucleic acid sequence of SEQ ID NO: 11.

12. A transgenic non-human animal having a genome comprising a transgene construct comprising a transgene construct comprising the nucleic acid sequence of either SEQ ID NO: 18 or 19.

13. The transgenic non-human animal of claim 12, wherein the transgene construct comprises the nucleic acid sequence of SEQ ID NO: 18.

14. The transgenic non-human animal of claim 12, wherein the transgene construct comprises the nucleic acid sequence of SEQ ID NO: 19.

15. A transgenic non-human animal having a genome comprising a transgene construct comprising a transgene construct comprising the nucleic acid sequence of either SEQ ID NO: 6 or 11.

16. The transgenic non-human animal of claim 15, wherein the transgene construct comprises the nucleic acid sequence of SEQ ID NO: 6.

17. The transgenic non-human animal of claim 15, wherein the transgene construct comprises the nucleic acid sequence of SEQ ID NO: 11.

* * * * *

UNITED STATES PATENT AND TRADEMARK OFFICE
CERTIFICATE OF CORRECTION

| | | |
|---|---|---|
| PATENT NO. | : 8,981,179 B2 | Page 1 of 1 |
| APPLICATION NO. | : 13/516077 | |
| DATED | : March 17, 2015 | |
| INVENTOR(S) | : Holly Dressler et al. | |

It is certified that error appears in the above-identified patent and that said Letters Patent is hereby corrected as shown below:

In the Specification

In column 2, lines 48-52, delete "It is useful........interpretation." and insert the same on Col. 2, Line 49 as a new paragraph.

In column 3, line 44, delete "Pharmacol" and insert -- Pharmacol. --, therefor.

In column 5, lines 31-32, delete "Biotechnol" and insert -- Biotechnol. --, therefor.

In column 13, line 20, delete "(UR);" and insert -- (I/R); --, therefor.

In column 15, line 29, delete "forskolin/bug" and insert -- forskolin/10 ug --, therefor.

In column 15, line 29, delete "bug" and insert -- 10 ug --, therefor.

In column 15, line 30, delete "forskolin/bug" and insert -- forskolin/10 ug --, therefor.

In column 22, line 16, delete "IVIS™" and insert -- IVIS® --, therefor.

In column 43, lines 19-39, after "nM." delete "Gi modulation.......activity." and insert the same on Col. 43, Line 20 as a new paragraph.

In column 44, line 6, delete "1×HBSS" and insert -- 1× HBSS --, therefor.

In the Claims

In column 69, line 23, in claim 1, delete "cyclin AMP response element (CRE)" and insert -- cyclic AMP response element (CRE) -- in place of the deleted language.

In column 70, lines 35-36, in claim 12, after "construct" delete "comprising a transgene construct".

In column 70, lines 45-46, in claim 15, after "construct" delete "comprising a transgene construct".

Signed and Sealed this
Eighteenth Day of August, 2015

Michelle K. Lee
*Director of the United States Patent and Trademark Office*